(12) United States Patent
Sakya et al.

(10) Patent No.: US 6,900,230 B2
(45) Date of Patent: May 31, 2005

(54) HETEROCYCLO-ALKYLSULFONYL PYRAZOLES AS ANTI-INFLAMMATORY/ANALGESIC AGENTS

(75) Inventors: Subas M. Sakya, East Lyme, CT (US); Bryson Rast, Mystic, CT (US)

(73) Assignee: Pfizer Inc., Groton, CT (US)

( * ) Notice: Subject to any disclaimer, the term of this patent is extended or adjusted under 35 U.S.C. 154(b) by 0 days.

(21) Appl. No.: 10/189,074

(22) Filed: Jul. 2, 2002

(65) Prior Publication Data

US 2003/0119836 A1 Jun. 26, 2003

Related U.S. Application Data

(60) Provisional application No. 60/303,169, filed on Jul. 5, 2001.

(51) Int. Cl.[7] .................... C07D 401/04; A61K 31/501; A61K 31/53
(52) U.S. Cl. .................. 514/341; 546/275.4; 546/276.1
(58) Field of Search .......................... 546/275.4, 276.1; 514/341

(56) References Cited

FOREIGN PATENT DOCUMENTS

| EP | 0418845 | 8/1995 | ......... C07D/231/14 |
|---|---|---|---|
| EP | 1099695 | 5/2001 | ......... C07D/249/08 |
| EP | 1104758 | 6/2001 | ......... C07D/401/04 |
| EP | 1104759 | 6/2001 | ......... C07D/405/14 |
| EP | 0554829 | 5/2002 | ......... C07D/231/12 |
| WO | WO 9500501 | 1/1995 | ......... C07D/277/02 |
| WO | WO 9515315 | 6/1995 | ......... C07D/231/12 |
| WO | WO 9515316 | 6/1995 | ......... C07D/231/12 |
| WO | WO 9515317 | 6/1995 | ......... C07D/231/12 |
| WO | WO 9515318 | 6/1995 | ......... C07D/231/12 |
| WO | WO 9603387 | 2/1996 | ......... C07D/233/54 |
| WO | WO 9603392 | 2/1996 | ......... C07D/277/26 |
| WO | WO 9608482 | 3/1996 | ......... C07D/307/58 |
| WO | WO 9619469 | 6/1996 | ......... C07D/307/58 |
| WO | WO 9619864 | 6/1996 | ............. H03F/1/32 |
| WO | WO 9636623 | 11/1996 | ......... C07D/307/60 |
| WO | WO 9711704 | 4/1997 | ......... A61K/31/635 |
| WO | WO 9713755 | 4/1997 | ......... C07D/231/12 |
| WO | WO 9714691 | 4/1997 | ......... C07D/307/58 |
| WO | WO 9716435 | 5/1997 | ......... C07D/307/32 |
| WO | WO 0140216 | 6/2001 | ......... C07D/401/04 |

OTHER PUBLICATIONS

Simone, Oncology: Introduction, Cecil Textbook Of Medicine, 20th Edition, vol. 1, pp. 1004–1010, 1996.*
Layzer, Degenerative Diseases of the Nervous System, Cecil Textbook of Medicine, 20th Edition, vol. 2, pp. 2050–2057, 1996.*

Damasio, Alzheimer's Disease and Related Dementias, Cecil Textbook of Medicine, 20th Edition, vol. 2, pp. 1992–1996, 1996.*

Freston, PubMed Abstract (Am J Med 107(6A):78S–88S; Discussion 89S), Dec. 1999.*

Naesdal et al., PubMed Abstract (Eur J Gastroenterol Hepatol, 13(12):1401–6), Dec. 2001.*

Vane J. R., et al., *Inducible isoforms of cyclooxygenase and nitric–oxide synthase in inflammation*, Proc. Natl. Acad. Sci. USA, vo 91, pp. 2046–2050, Mar. 1994.

Penning, T. D., et al., *Synthesis and Biological Evaluation of the 1,5–diarylpyrazole Class of Cyclooxygenas–2 Inhibitors: Identification of 4–[5–(4–methylphenyl)–3–(trifluoromethyl)–1H–pyrazol–1–yl]benzenesulfonamide (SC–58635, Celecoxib), J. Med. Chem.*, 1997, 40, pp. 1347–1365.

Tsuji, K., et al., *Studies on Anti–inflammatory Agents. IV. Synthesis and Pharmacological Properties of 1,5–Diarylpyrazoles and Related Derivatives, Chem. Pharm. Bull.*, 45(6), pp. 987–995, 1997.

* cited by examiner

*Primary Examiner*—Deepak Rao
(74) *Attorney, Agent, or Firm*—Peter C. Richardson; Thomas A. Wootton; Mary J. Hosley

(57) ABSTRACT

The present invention relates to compounds of the formula

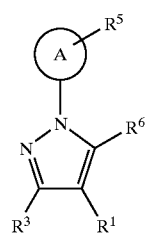

I wherein $R^1$, $R^3$, $R^5$, $R^6$, and A are defined as in the specification, to pharmaceutical compositions containing them and to their medicinal use. The compounds of the invention are useful in the treatment of inflammation and other inflammation associated disorders, such as osteoarthritis, rheumatoid arthritis, colon cancer and Alzheimer's disease, in mammals (preferably humans, dogs, cats and livestock).

24 Claims, No Drawings

HETEROCYCLO-ALKYLSULFONYL PYRAZOLES AS ANTI-INFLAMMATORY/ANALGESIC AGENTS

CROSS-REFERENCE TO RELATED APPLICATION

This application claims priority of U.S. provisional application Ser. No. 60/303,169, filed Jul. 5, 2001.

BACKGROUND OF THE INVENTION

This invention relates to heterocyclo-alkylsulfonyl pyrazoles, methods of treatment and pharmaceutical compositions for the treatment of cyclooxygenase mediated diseases, such as arthritis, neurodegeneration and colon cancer, in mammals, preferably humans, dogs, cats or livestock.

Nonsteroidal anti-inflammatory drugs (NSAIDs) are widely used in treating pain and the signs and symptoms of arthritis because of their analgesic and anti-inflammatory activity. Common NSAIDs work by blocking the activity of cyclooxygenase (COX), an enzyme that converts arachidonic acid into prostanoids. Two forms of COX are now known, a constitutive isoform (COX-1) and an inducible isoform (COX-2) of which expression is upregulated at sites of inflammation (Vane, J. R.; Mitchell, et. al., *Proc. Natl. Acad. Sci. USA*, 1994, 91, 2046). COX-1 appears to play a physiological role and to be responsible for gastrointestinal and renal protection. On the other hand, COX-2 appears to play a pathological role and is believed to be the predominant isoform present in inflammation conditions. The therapeutic use of conventional NSAIDs is, however, limited due to drug associated side effects, including life threatening ulceration and renal toxicity.

COX is also known as prostaglandin G/H synthase (PGHS). Prostaglandins, especially prostaglandin $E_2$ ($PGE_2$), a predominant eicosanoid detected in inflammation conditions, are mediators of pain, fever and other symptoms associated with inflammation. A pathological role for prostaglandins has been implicated in a number of human diseases including rheumatoid arthritis, osteoarthritis, pyrexia, asthma, bone resorption, cardiovascular diseases, dysmenorrhea, premature labour, nephritis, nephrosis, atherosclerosis, hypotension, shock, pain, cancer and Alzheimer. Compounds that selectively inhibit the biosynthesis of prostaglandins by intervention of the induction phase of the inducible enzyme COX-2 and/or by intervention of the activity of the enzyme COX-2 on arachidonic acid would provide alternate therapy to the use of NSAIDs or corticosteriods in that such compounds would exert anti-inflammatory effects without the adverse side effects associated with COX-1 inhibition.

A variety of sulfonylbenzene compounds which inhibit COX have been disclosed in patent publications (WO 97/11704, WO 97/16435, WO 97/14691, WO 96/19469, WO 96/36623, WO 96/03392, WO 96/03387, WO 96/19469, WO 96/08482, WO 95/00501, WO 95/15315, WO 95/15316, WO 95/15317, WO 95/15318, WO 97/13755, EP 0799523, EP 418845, EP 554829 and EP 1099695).

SUMMARY OF THE INVENTION

The present invention relates to compounds of the formula

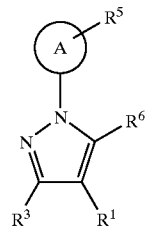

I wherein

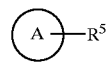

is a heterocycle selected from the group consisting of

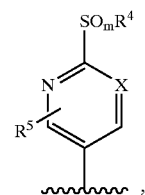

A1

A2

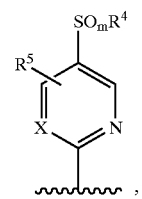

A3

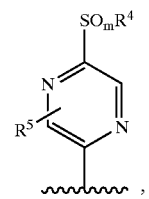

A4

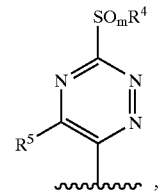

A5

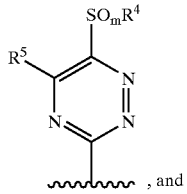

, and

-continued

A6

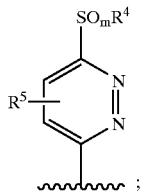

m is 0, 1 or 2, preferably m is 2;

X is $CR^7$ or N, preferably $CR^7$ wherein $R^7$ is hydrogen;

$R^1$ is hydrogen, halo, $(C_1-C_6)$alkyl, $(C_2-C_6)$alkenyl, $(C_2-C_6)$alkynyl, $(C_3-C_7)$carbocyclyl, $(C_1-C_6)$alkoxy, $(C_1-C_6)$alkylcarbonyl, formyl, formamidyl, cyano, nitro, hydroxycarbonyl, $(C_1C_6)$alkoxycarbonyl, $(C_2-C_9)$heteroarylcarbonyl, amino, N—$(C_1-C_6)$alkylamino, N,N—$[(C_1-C_6)$alkyl$]_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—$[(C_1-C_6)$alkyl$]_2$amido, N—$(C_6-C_{10})$arylamido, N—$(C_1-C_6)$alkyl-N—$(C_6-C_{10})$arylamido, N—$(C_1-C_6)$alkoxyamido, $(C_6-C_{10})$aryl, $(C_6-C_{10})$aryloxy, $(C_2-C_9)$heteroaryl, $(C_2-C_9)$heteroaryloxy, $(C_1-C_6)$alkylthio, $(C_6-C_{10})$arylthio, $(C_2-C_9)$heteroarylthio, $(C_1-C_6)$alkyl-S(=O)—, $(C_1-C_6)$alkyl-SO$_2$—, or $(C_1-C_6)$alkylcarbonyl-N($R^2$)—;

wherein each of said $R^1$ $(C_1-C_6)$alkyl group wherever they occur may optionally be substituted with one to three substituents independently selected from the group consisting of halo, hydroxy, $(C_2-C_6)$alkenyl, $(C_2-C_6)$alkynyl, $(C_3-C_7)$carbocyclyl, $(C_1-C_6)$alkoxy, carbonyl, formyl, formamidyl, $(C_1-C_6)$alkylcarbonyl, cyano, mercapto, nitro, hydroxycarbonyl, $(C_1-C_6)$alkoxycarbonyl, amino, N—$(C_1-C_6)$alkylamino, N,N—$[(C_1-C_6)$alkyl$]_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—$[(C_1-C_6)$alkyl$]_2$amido, N—$(C_6-C_{10})$arylamido, N—$(C_1-C_6)$alkyl-N—$(C_6-C_{10})$arylamido, $(C_1-C_6)$alkoxyamido, $(C_6-C_{10})$aryl, $(C_6-C_{10})$aryloxy, $(C_2-C_9)$heteroaryl, $(C_2-C_9)$heteroaryloxy, $(C_2-C_9)$heteroarylcarbonyl, $(C_1-C_6)$alkylthio, $(C_1-C_6)$alkyl-S(=O)—, $(C_1-C_6)$alkyl-SO$_2$—, $(C_1-C_6)$alkylcarbonyl-N($R^2$)—, and $(C_1-C_6)$alkylcarbonyloxy;

$R^2$ is hydrogen or $(C_1-C_6)$alkyl;

$R^3$ is $(C_1-C_6)$alkylthio, $(C_3-C_7)$carbocyclylthio, $C_6-C_{10}$)arylthio, $(C_2-C_9)$heteroarylthio, $(C_1-C_6)$alkyl-S(=O)—, $(C_6-C_{10})$aryl-S(=O)—, $(C_2-C_9)$heteroaryl-S(=O)—, $(C_1-C_6)$alkyl-SO$_2$-, $(C_6-C_{10})$aryl-SO$_2$—, $(C_2-C_9)$heteroaryl-SO$_2$—, $(C_1-C_6)$alkyl-SO$_2$-amino, $(C_3-C_7)$carbocyclyl-SO$_2$-amino, $(C_6-C_{10})$aryl-SO$_2$-amino, $(C_2-C_9)$heteroaryl-SO$_2$-amino, amino-SO$_2$—, N—$(C_1-C_6)$alkylamino-SO$_2$—, N,N—$[(C_1-C_6)$alkyl$]_2$amino-SO$_2$—, N—$(C_3-C_7)$carbocyclylamino-SO$_2$—, N—$(C_6-C_{10})$arylamino-SO$_2$—, N—$(C_1-C_6)$alkyl-N—$(C_6-C_{10})$arylamino-SO$_2$—, N—$(C_2-C_9)$heteroarylamino-SO$_2$—, amino, N—$(C_1-C_6)$alkylamino, N,N—$[(C_1-C_6)$alkyl$]_2$amino, N—$(C_3-C_7)$carbocyclylamino, N—$(C_6-C_{10})$arylamino, N—$(C_1-C_6)$alkyl-N—$(C_6-C_{10})$arylamino, or N—$(C_2-C_9)$heteroarylamino;

wherein each of said $R^3$ $(C_1-C_6)$alkyl group wherever they occur may optionally be substituted with one to three substituents independently selected from the group consisting of halo, hydroxy, $(C_2-C_6)$alkenyl, $(C_2-C_6)$alkynyl, $(C_3-C_7)$carbocyclyl, $(C_1-C_6)$alkoxy, carbonyl, formyl, formamidyl, $(C_1-C_6)$alkylcarbonyl, cyano, mercapto, nitro, hydroxycarbonyl, $(C_1-C_6)$alkoxycarbonyl, amino, N—$(C_1-C_6)$alkylamino, N,N—$[(C_1-C_6)$alkyl$]_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—$[(C_1-C_6)$alkyl$]_2$amido, N—$(C_6-C_{10})$arylamido, N—$(C_1-C_6)$alkyl-N—$(C_6-C_{10})$arylamido, $(C_1-C_6)$alkoxyamido, $(C_6-C_{10})$aryl, $(C_6-C_{10})$aryloxy, $(C_2-C_9)$heteroaryl, $(C_2-C_9)$heteroaryloxy, $(C_2-C_9)$heteroarylcarbonyl, $(C_1-C_6)$alkylthio, $(C_1-C_6)$alkyl-S(=O)—, $(C_1-C_6)$alkyl-SO$_2$—, $(C_1-C_6)$alkylcarbonyl-N($R^2$)—, and $(C_1-C_6)$alkylcarbonyloxy;

$R^4$ is $(C_1-C_6)$alkyl optionally substituted by hydroxy or one to three halo atoms, such as fluoro atoms;

$R^5$ is hydrogen, halo, hydroxy, mercapto, $(C_1-C_6)$alkyl, $(C_1-C_6)$alkoxy optionally substituted with one to three halo (such as fluoro) atoms, $(C_2-C_6)$alkenyl, $(C_2-C_6)$alkynyl, $(C_3-C_7)$carbocyclyl, cyano, formyl, $(C_1-C_6)$alkylcarbonyl, $(C_1-C_6)$alkylcarbonyloxy, hydroxycarbonyl, $(C_1-C_6)$alkoxycarbonyl, amino, N—$(C_1-C_6)$alkylamino, N,N—$[(C_1-C_6)$alkyl$]_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—$[(C_1-C_6)$alkyl$]_2$amido, N—$(C_6-C_{10})$arylamido, N—$(C_1-C_6)$alkyl-N—$(C_6-C_{10})$arylamido, N—$(C_1-C_6)$alkoxyamido, or $(C_1-C_6)$alkylthio;

wherein each of said $R^5$ $(C_1-C_6)$alkyl group wherever they occur may optionally be substituted with one to three substituents independently selected from the group consisting of halo, hydroxy, $(C_2-C_6)$alkenyl, $(C_2-C_6)$alkynyl, $(C_3-C_7)$carbocyclyl, $(C_1-C_6)$alkoxy, carbonyl, formyl, formamidyl, $(C_1-C_6)$alkylcarbonyl, cyano, mercapto, nitro, hydroxycarbonyl, $(C_1-C_6)$alkoxycarbonyl, amino, N—$(C_1-C_6)$alkylamino, N,N—$[(C_1-C_6)$alkyl$]_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—$[(C_1-C_6)$alkyl$]_2$amido, N—$(C_8-C_{10})$arylamido, N—$(C_1-C_6)$alkyl-N—$(C_6-C_{10})$arylamido, $(C_1-C_6)$alkoxyamido, $(C_6-C_{10})$aryl, $(C_6-C_{10})$aryloxy, $(C_2-C_9)$heteroaryl, $(C_2-C_9)$heteroaryloxy, $(C_2-C_9)$heteroarylcarbonyl, $(C_1-C_6)$alkylthio, $(C_1-C_6)$alkyl-S(=O)—, $(C_1-C_6)$alkyl-SO$_2$—, $(C_1-C_6)$alkylcarbonyl-N($R^2$)—, and $(C_1-C_6)$alkylcarbonyloxy;

$R^6$ is selected from the group consisting of:

(a) phenyl optionally substituted by one to three, preferably one, substituents independently selected from the group consisting of halo (preferably fluoro), hydroxy, cyano, mercapto, hydroxycarbonyl, nitro, $(C_1-C_6)$alkyl (preferably methyl), $(C_2-C_6)$alkenyl, $(C_2-C_6)$alkynyl, $(C_3-C_7)$carbocyclyl, $(C_1-C_6)$alkoxy, —OCF$_3$, $(C_1-C_6)$alkylthio, $(C_1-C_6)$alkyl-S(=O)—, $(C_1-C_6)$alkyl-SO$_2$—, amino, N—$(C_1-C_6)$alkylamino, N,N—$[(C_1-C_6)$alkyl$]_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—$[(C_1-C_6)$alkyl$]_2$amido, N—$(C_6-C_{10})$arylamido, N—$(C_1-C_6)$alkyl-N—$(C_6-C_{10})$arylamido, N—$(C_1-C_6)$alkoxyamido, $(C_1-C_6)$alkylcarbonyloxy, $(C_1-C_6)$alkylcarbonyl-N($R^2$)—, formyl, $(C_1-C_6)$alkylcarbonyl, $(C_1-C_6)$alkoxycarbonyl, $(C_6-C_{10})$aryl and $(C_2-C_9)$heterocyclyl; preferably halo, most preferably one fluoro atom, or $(C_1-C_6)$alkyl, most preferably methyl;

(b) phenyl fused to a saturated, partially saturated or aromatic (5- to 7-membered)-carbocyclic ring;

wherein either of said phenyl or said fused saturated, partially saturated or aromatic (5- to 7-membered)- carbocyclic ring is optionally substituted by one to two substituents per ring, wherein said substituents are independently selected from the group consisting of halo, hydroxy, cyano, mercapto, hydroxycarbonyl, nitro, $(C_1–C_6)$alkyl, $(C_2–C_6)$alkenyl, $(C_2–C_6)$alkynyl, $(C_3–C_7)$carbocyclyl, $(C_1–C_6)$alkoxy, —$OCF_3$, $(C_1–C_6)$alkylthio, $(C_1–C_6)$alkyl-S(═O)—, $(C_1–C_6)$alkyl-$SO_2$—, amino, N—$(C_1–C_6)$alkylamino, N,N—$[(C_1–C_6)$alkyl$]_2$amino, N—$(C_3–C_7)$carbocyclylamino, N—$(C_6–C_{10})$arylamino, N—$(C_1–C_6)$alkyl-N—$(C_6–C_{10})$arylamino, N—$(C_2–C_9)$heteroarylamino, amido, N—$(C_1–C_6)$alkylamido, N,N—$[(C_1–C_6)$alkyl$]_2$amido, N—$(C_6–C_{10})$arylamido, N—$(C_1–C_6)$alkyl-N—$(C_6–C_{10})$arylamido, N—$(C_1–C_6)$alkoxyamido, $(C_1–C_6)$alkylcarbonyloxy, $(C_1–C_6)$alkylcarbonyl-N($R^2$)—, formyl, $(C_1–C_6)$alkylcarbonyl, $(C_1–C_6)$alkoxycarbonyl, $(C_6–C_{10})$aryl and $(C_2–C_9)$heterocyclyl;

(c) phenyl fused to a saturated, partially saturated or aromatic (5- to 6-membered)-heterocyclyl containing one to two ring heteroatoms independently selected from the group consisting of —N═, —$NR^2$—, —S— and —O—;

wherein either of said phenyl or said fused saturated, partially saturated or aromatic (5- to 6-membered)-heterocyclyl is optionally substituted with one to two substituents per ring;

wherein said substituents are independently selected from the group consisting of halo, hydroxy, cyano, mercapto, hydroxycarbonyl, nitro, $(C_1–C_6)$alkyl, $(C_2–C_6)$alkenyl, $(C_2–C_6)$alkynyl, $(C_3–C_7)$carbocyclyl, $(C_1–C_6)$alkoxy, —$OCF_3$, $(C_1–C_6)$alkylthio, $(C_1–C_6)$alkyl-S(═O)—, $(C_1–C_6)$alkyl-$SO_2$—, amino, N—$(C_1–C_6)$alkylamino, N,N—$[(C_1–C_6)$alkyl$]_2$amino, N—$(C_3–C_7)$carbocyclylamino, N—$(C_6–C_{10})$arylamino, N—$(C_1–C_6)$alkyl-N—$(C_6–C_{10})$arylamino, N—$(C_2–C_9)$heteroarylamino, amido, N—$(C_1–C_6)$alkylamido, N,N—$[(C_1–C_6)$alkyl$]_2$amido, N—$(C_6–C_{10})$arylamido, N—$(C_1–C_6)$alkyl-N—$(C_6–C_{10})$arylamido, N—$(C_1–C_6)$alkoxyamido, $(C_1–C_6)$alkylcarbonyloxy, $(C_1–C_6)$alkylcarbonyl-N($R^2$)—, formyl, $(C_1–C_6)$alkylcarbonyl, $(C_1–C_6)$alkoxycarbonyl, $(C_6–C_{10})$aryl and $(C_2–C_9)$heterocyclyl;

(d) (3- to 7-membered)-carbocyclic optionally containing one or two double bonds, preferably the (3- to 7-membered)-carbocyclic contains no double bonds;

wherein said (3- to 7-membered)-carbocyclic may also be optionally substituted by one to three substituents independently selected from the group consisting of halo, hydroxy, cyano, mercapto, hydroxycarbonyl, nitro, $(C_1–C_6)$alkyl, $(C_2–C_6)$alkenyl, $(C_2–C_6)$alkynyl, $(C_3–C_7)$carbocyclyl, $(C_1–C_6)$alkoxy, —$OCF_3$, $(C_1–C_6)$alkylthio, $(C_1–C_6)$alkyl-S(═O)—, $(C_1–C_6)$alkyl-$SO_2$—, amino, N—$(C_1–C_6)$alkylamino, N,N—$[(C_1–C_6)$alkyl$]_2$amino, N—$(C_3–C_7)$carbocyclylamino, N—$(C_6–C_{10})$arylamino, N—$(C_1–C_6)$alkyl-N—$(C_6–C_{10})$arylamino, N—$(C_2–C_9)$heteroarylamino, amido, N—$(C_1–C_6)$alkylamido, N,N—$[(C_1–C_6)$alkyl$]_2$amido, N—$(C_6–C_{10})$arylamido, N—$(C_1–C_6)$alkyl-N—$(C_6–C_{10})$arylamido, N—$(C_1–C_6)$alkoxyamido, $(C_1–C_6)$alkylcarbonyloxy, $(C_1–C_6)$alkylcarbonyl-N($R^2$)—, formyl, $(C_1–C_6)$alkylcarbonyl, $(C_1–C_6)$alkoxycarbonyl, $(C_6–C_{10})$aryl and $(C_2–C_9)$heterocyclyl;

(e) (5- to 7-membered)-carbocyclic fused to a saturated, partially saturated or aromatic (5- to 7-membered)-carbocyclic ring;

wherein said (5- to 7-membered)-carbocyclic may optionally contain one or two double bonds;

wherein either of said (5- to 7-membered)-carbocyclic or said fused saturated, partially saturated or aromatic (5- to 7-membered)-carbocyclic ring is optionally substituted by one to two substituents per ring, wherein said substituents are independently selected from the group consisting of halo, hydroxy, cyano, mercapto, hydroxycarbonyl, nitro, $(C_1–C_6)$alkyl, $(C_2–C_6)$alkenyl, $(C_2–C_6)$alkynyl, $(C_3–C_7)$carbocyclyl, $(C_1–C_6)$alkoxy, —$OCF_3$, $(C_1–C_6)$alkylthio, $(C_1–C_6)$alkyl-S(═O)—, $(C_1–C_6)$alkyl-$SO_2$—, amino, N—$(C_1–C_6)$alkylamino, N,N—$[(C_1–C_6)$alkyl$]_2$amino, N—$(C_3–C_7)$carbocyclylamino, N—$(C_6–C_{10})$arylamino, N—$(C_1–C_6)$alkyl-N—$(C_6–C_{10})$arylamino, N—$(C_2–C_9)$heteroarylamino, amido, N—$(C_1–C_6)$alkylamido, N,N—$[(C_1–C_6)$alkyl$]_2$amido, N—$(C_6–C_{10})$arylamido, N—$(C_1–C_6)$alkyl-N—$(C_6–C_{10})$arylamido, N—$(C_1–C_6)$alkoxyamido, $(C_1–C_6)$alkylcarbonyloxy, $(C_1–C_6)$alkylcarbonyl-N($R^2$)—, formyl, $(C_1–C_6)$alkylcarbonyl, $(C_1C_6)$alkoxycarbonyl, $(C_6–C_{10})$aryl and $(C_2–C_9)$heterocyclyl;

(f) (5- to 7-membered)-carbocyclic fused to a saturated, partially saturated or aromatic (5- to 6-membered)-heterocyclyl containing one to two ring heteroatoms independently selected from the group consisting of —N═, —$NR^2$—, —S— and —O—;

wherein said (5- to 7-membered)-carbocyclic may optionally contain one or two double bonds;

wherein either of said (5- to 7-membered)-carbocyclic or said fused saturated, partially saturated or aromatic (5- to 6-membered)-heterocyclyl is optionally substituted with one to two substituents per ring;

wherein said substituents are independently selected from the group consisting of halo, hydroxy, cyano, mercapto, hydroxycarbonyl, nitro, $(C_1–C_6)$alkyl, $(C_2–C_6)$alkenyl, $(C_2–C_6)$alkynyl, $(C_3–C_7)$carbocyclyl, $(C_1–C_6)$alkoxy, —$OCF_3$, $(C_1–C_6)$alkylthio, $(C_1–C_6)$alkyl-S(═O)—, $(C_1–C_6)$alkyl-$SO_2$—, amino, N—$(C_1–C_6)$alkylamino, N,N—$[(C_1–C_6)$alkyl$]_2$amino, N—$(C_3–C_7)$carbocyclylamino, N—$(C_6–C_{10})$arylamino, N—$(C_1–C_6)$alkyl-N—$(C_6–C_{10})$arylamino, N—$(C_2–C_9)$heteroarylamino, amido, N—$(C_1–C_6)$alkylamido, N,N—$[(C_1–C_6)$alkyl$]_2$amido, N—$(C_6–C_{10})$arylamido, N—$(C_1–C_6)$alkyl-N—$(C_6–C_{10})$arylamido, N—$(C_1–C_6)$alkoxyamido, $(C_1–C_6)$alkylcarbonyloxy, $(C_1–C_6)$alkylcarbonyl-N($R^2$)—, formyl, $(C_1–C_6)$alkylcarbonyl, $(C_1–C_6)$alkoxycarbonyl, $(C_6–C_{10})$aryl and $(C_2–C_9)$heterocyclyl;

(g) saturated, partially saturated or aromatic, preferably aromatic, (5- to 6-membered)-heterocyclyl containing one to four, preferably one, ring heteroatom(s) independently selected from the groups consisting of —N═, —$NR_2$—, —O—, and —S—, preferably selected from the group consisting of —O—, and —S—;

wherein said (5- to 6-membered)-heterocyclyl is optionally substituted by one to three substituents independently selected from the group consisting of halo, hydroxy, cyano, mercapto, hydroxycarbonyl, nitro, $(C_1–C_6)$alkyl, $(C_2–C_6)$alkenyl, $(C_2–C_6)$alkynyl, $(C_3–C_7)$carbocyclyl, $(C_1–C_6)$alkoxy, —$OCF_3$, $(C_1–C_6)$alkylthio, $(C_1–C_6)$alkyl-S(═O)—, $(C_1–C_6)$alkyl-$SO_2$—, amino, N—$(C_1–C_6)$alkylamino, N,N—$[(C_1–C_6)$alkyl$]_2$amino, N—$(C_3–C_7)$carbocyclylamino, N—$(C_6–C_{10})$arylamino, N—$(C_1–C_6)$alkyl-N—$(C_6–C_{10})$arylamino, N—$(C_2–C_9)$heteroarylamino, amido, N—$(C_1–C_6)$alkylamido, N,N—$[(C_1–C_6)$alkyl$]_2$amido, N—$(C_6–C_{10})$arylamido, N—$(C_1–C_6)$alkyl-N—$(C_6–C_{10})$arylamido, N—$(C_1–C_6)$alkoxyamido, $(C_1–C_6)$alkylcarbonyloxy, $(C_1–C_6)$alkylcarbonyl-N($R^2$)—, formyl, $(C_1–C_6)$alkylcarbonyl, $(C_1–C_6)$alkoxycarbonyl, $(C_6–C_{10})$aryl and $(C_2–C_9)$heterocyclyl; preferably said (5- to 6-membered)-heterocyclyl is unsubstituted;

(h) saturated, partially saturated or aromatic (5- to 6-membered)-heterocyclyl containing one to two ring heteroatoms independently selected from the group consisting of —N=, —NR$^2$—, —S— and —O—;

wherein said saturated, partially saturated or aromatic (5- to 6-membered)-heterocyclyl is fused to a saturated, partially saturated or aromatic (5- to 7-membered)-carbocyclic ring;

wherein either of said saturated, partially saturated or aromatic (5- to 6-membered)-heterocyclyl ring or said fused saturated, partially saturated or aromatic (5- to 7-membered)-carbocyclic ring is optionally substituted by one to two substituents per ring;

wherein said substituents are independently selected from the group consisting of halo, hydroxy, cyano, mercapto, hydroxycarbonyl, nitro, $(C_1-C_6)$alkyl, $(C_2-C_6)$alkenyl, $(C_2-C_6)$alkynyl, $(C_3-C_7)$carbocyclyl, $(C_1-C_6)$alkoxy, —OCF$_3$, $(C_1-C_6)$alkylthio, $(C_1-C_6)$alkyl-S(=O)—, $(C_1-C_6)$alkyl-SO$_2$—, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_6-C_{10})$arylamido, N—$(C_1-C_6)$alkyl-N—$(C_6-C_{10})$arylamido, N—$(C_1-C_6)$alkoxyamido, $(C_1-C_6)$alkylcarbonyloxy, $(C_1-C_6)$alkylcarbonyl-N(R$^2$)—, formyl, $(C_1-C_6)$alkylcarbonyl, $(C_1-C_6)$alkoxycarbonyl, $(C_6-C_{10})$aryl and $(C_2-C_9)$heterocyclyl; and (i) saturated, partially saturated or aromatic (5- to 6-membered)-heterocyclyl containing one to two ring heteroatoms independently selected from the group consisting of —N=, —NR$^2$—, —S—, and —O—;

wherein said saturated, partially saturated or aromatic (5- to 6-membered)-heterocyclyl is fused to a saturated, partially saturated or aromatic (5- to 6-membered)-heterocyclyl containing one to two ring heteroatoms independently selected from the group consisting of —N=, —NR$^2$—, —S— and —O—;

wherein either of said saturated, partially saturated or aromatic (5- to 6-membered)-heterocyclyl or said fused saturated, partially saturated or aromatic (5- to 6-membered)-heterocyclyl is optionally substituted with one to twosubstituents per ring;

wherein said substituents are independently selected from the group consisting of halo, hydroxy, cyano, mercapto, hydroxycarbonyl, nitro, $(C_1-C_6)$alkyl, $(C_2-C_6)$alkenyl, $(C_2-C_6)$alkynyl, $(C_3-C_7)$carbocyclyl, $(C_1-C_6)$alkoxy, —OCF$_3$, $(C_1-C_6)$alkylthio, $(C_1-C_6)$alkyl-S(=O)—, $(C_1-C_6)$alkyl-SO$_2$—, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_6-C_{10})$arylamido, N—$(C_1-C_6)$alkyl-N—$(C_6-C_{10})$arylamido, N—$(C_1-C_6)$alkoxyamido, $(C_1-C_6)$alkylcarbonyloxy, $(C_1-C_6)$alkylcarbonyl-N(R$^2$)—, formyl, $(C_1-C_6)$alkylcarbonyl, $(C_1-C_6)$alkoxycarbonyl, $(C_6-C_{10})$aryl and $(C_2-C_9)$heterocyclyl;

wherein each of said R$^1$ (a), (b), (c), (d), (e), (f), (g), (h), or (i) $(C_1-C_6)$alkyl group wherever they occur may optionally be substituted with one to three substituents independently selected from the group consisting of halo, hydroxy, $(C_2-C_6)$alkenyl, $(C_2-C_6)$alkynyl, $(C_3-C_7)$carbocyclyl, $(C_1-C_6)$alkoxy, carbonyl, formyl, formamidyl, $(C_1-C_6)$alkylcarbonyl, cyano, mercapto, nitro, hydroxycarbonyl, $(C_1-C_6)$alkoxycarbonyl, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N—$(C_{10})$arylamido, $(C_1-C_6)$alkoxyamido, $(C_6-C_{10})$aryl, $(C_6-C_{10})$aryloxy, $(C_2-C_9)$heteroaryl, $(C_2C_9)$heteroaryloxy, $(C_2-C_9)$heteroarylcarbonyl, $(C_1-C_6)$alkylthio, $(C_1-C_6)$alkyl-S(=O)—, $(C_1C_6)$alkyl-SO$_2$—, $(C_1-C_6)$alkylcarbonyl-N(R$^2$)—, and $(C_1-C_6)$alkylcarbonyloxy;

R$^7$ is hydrogen, halo, hydroxy, mercapto, $(C_1-C_6)$alkyl, $(C_1-C_6)$alkoxy, optionally substituted with one to three halogen atoms, $(C_2-C_6)$alkenyl, $(C_2-C_6)$alkynyl, $(C_3-C_7)$carbocyclyl, cyano, formyl, $(C_1-C_6)$alkylcarbonyl, $(C_1-C_6)$alkylcarbonyloxy, hydroxycarbonyl, $(C_1-C_6)$alkoxycarbonyl, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N—$(C_6-C_{10})$arylamido, N—$(C_1-C_6)$alkoxyamido, nitro, or $(C_1-C_6)$alkylthio;

wherein each of said R$^7$ $(C_1-C_6)$alkyl group wherever they occur may optionally be substituted with one to three substituents independently selected from the group consisting of halo, hydroxy, $(C_2-C_6)$alkenyl, $(C_2-C_6)$alkynyl, $(C_3-C_7)$carbocyclyl, $(C_1-C_6)$alkoxy, carbonyl, formyl, formamidyl, $(C_1-C_6)$alkylcarbonyl, cyano, mercapto, nitro, hydroxycarbonyl, $(C_1-C_6)$alkoxycarbonyl, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N—$(C_6-C_{10})$arylamido, $(C_1-C_6)$alkoxyamido, $(C_6-C_{10})$aryl, $(C_6-C_{10})$aryloxy, $(C_2-C_9)$heteroaryl, $(C_2-C_9)$heteroaryloxy, $(C_2-C_9)$heteroarylcarbonyl, $(C_1-C_6)$alkylthio, $(C_1-C_6)$alkyl-S(=O)—, $(C_1-C_6)$alkyl-SO$_2$—, $(C_1-C_6)$alkylcarbonyl-N(R$^2$)—, and $(C_1-C_6)$alkylcarbonyloxy;

and the pharmaceutically acceptable salts thereof.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, para-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine (meglumine), and the lower alkanolammonium and other base salts of pharmaceutically acceptable organic amines.

The compounds of this invention include all stereoisomers (e.g., cis and trans isomers) and all optical isomers of compounds of the formula I (e.g., R and S enantiomers), as well as racemic, diastereomeric and other mixtures of such isomers.

The compounds of the invention also exist in different tautomeric forms. This invention relates to all tautomers of formula I.

The compounds of this invention may contain olefin-like double bonds. When such bonds are present, the compounds of the invention exist as cis and trans configurations and as mixtures thereof.

Unless otherwise indicated, the alkyl, referred to herein, as well as the alkyl moieties of other groups referred to herein (e.g., alkoxy), may be linear or branched (such as methyl, ethyl, n-propyl, isopropyl, n-butyl, iso-butyl, secondary-butyl, tertiary-butyl).

Unless otherwise indicated, halo includes fluoro, chloro, bromo or iodo.

As used herein, the term "alkenyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, or 2-butenyl.

As used herein, the term "alkynyl" is used herein to mean straight or branched hydrocarbon chain radicals of 2 to 6 carbon atoms having one triple bond including, but not limited to, ethynyl, propynyl, or butynyl.

As used herein, the term "alkoxy" refers to O-alkyl groups, wherein alkyl is as defined above.

As used herein, the term "alkoxycarbonyl" refers to an alkoxy radical as described above connected to a carbonyl group (>C=O), which, in turn, serves as the point of attachment.

As used herein, the term "carbocyclyl" refers to a mono or bicyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds.

As used herein, the term "amido" refers to aminocarbonyl- or carbamoyl- or $NH_2$—(C=O)— moiety.

As used herein the term "aryl" means aromatic radicals such as phenyl, naphthyl, tetrahydronaphthyl, or indanyl.

As used herein the term "heteroaryl" refers to aromatic groups containing one or more heteroatoms (O, S, or N). A multicyclic group containing one or more heteroatoms wherein at least one ring of the group is aromatic is a s"heteroaryl" group. The heteroaryl groups of this invention can also include ring systems substituted with one or more oxo moieties. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

The term "heterocyclic" as used herein refers to a cyclic group containing 2–9 carbon atoms and 1–4 hetero atoms selected from N, O, or S. Examples of such rings include furyl, thienyl, pyrrolyl, pyrazolyl, imidazolyl, triazolyl, tetrazolyl, isoxazolyl, oxazolyl, thiazolyl, isothiazolyl, oxadiazolyl, oxatriazolyl, pyridyl, pyridazinyl, pyrimidinyl, pyrazinyl, triazinyl, and the like. Examples of said monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholine, 1,2-tetrahydrothiazin-2-yl, 1,3-tetrahydrothiazin-3-yl, tetrahydrothiadiazine, morpholine, 1,2-tetrahydrodiazin-2-yl, 1,3-tetrahydrodiazin-1-yl, 1,4-oxazin-2-yl, 1,2,5-oxathiazin-4-yl and the like; optionally substituted by 1 to 3 suitable substituents as defined below such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

The term "phenyl fused to a saturated, partially saturated or aromatic (5- to 7-membered)-carbocyclic ring", as used herein, unless otherwise indicated, means a bicyclic group having a first phenyl ring covalently bound to the pyrazole nucleus and wherein said first ring is fused to a second ring comprising a 5 to 7 membered carbocycle, wherein the 5 to 7 members include the carbon atoms common to both rings. Examples of such rings include tetralin-5-yl, tetralin-6-yl, 2,3-dihydro-inden-4-yl, 2,3-dihydro-inden-5-yl, inden-4-yl, inden-5-yl, 7,8-dihydro-naphthalen-1-yl, 7,8-dihydro-naphthalen-2-yl, 5,6-dihydro-naphthalen-1-yl, 5,6-dihydro-naphthalen-2-yl, 5,8-dihydro-naphthalen-1-yl, 5,8-dihydro-naphthalen-2-yl, naphthalen-1-yl, naphthalen-2-yl, 5-(6,7,8,9-tetrahydro-5H-benzocyclohepten-1-yl)-, 5-(8,9-dihydro-7H-benzocyclohepten-1-yl)-, 5-(6,7-dihydro-5H-benzocyclohepten-1-yl)-, 5-(7H-benzocyclohepten-1-yl)-, 5-(5H-benzocyclohepten-1-yl)-, 5-(9H-benzocyclohepten-1-yl)-, 5-(6,7,8,9-tetrahydro-5H-benzocyclohepten-2-yl)-, 5-(6,7-dihydro-5H-benzocyclohepten-2-yl)-, 5-(8,9-dihydro-7H-benzocyclohepten-2-yl)-, 5-(5H-benzocyclohepten-2-yl)-, 5-(9H-benzocyclohepten-2-yl )-, or 5-(7H-benzocyclohepten-2-yl )-.

The term "phenyl fused to a saturated, partially saturated or aromatic (5- to 6-membered)-heterocyclic ring", as used herein, unless otherwise indicated, means a bicyclic group having a first phenyl ring covalently bound to the pyrazole nucleus and wherein said first ring is fused to a second ring comprising a (5- to 6-membered)-heterocyclic ring, wherein the 5 to 6 members include the carbon atoms common to both rings. Said second ring comprises a saturated, partially saturated or aromatic (5- to 6-membered)-heterocyclic ring. Examples of such rings include quinolin-5-yl, quinolin-6-yl, quinolin-7-yl, quinolin-8-yl, isoquinolin-5-yl, isoquinolin-6-yl, isoquinolin-7-yl, isoquinolin-8-yl, quinazolin-5-yl, quinazolin-6-yl, quinazolin-7-yl, quinazolin-8-yl, cinnolin-5-yl, cinnolin-6-yl, cinnolin-7-yl, cinnolin-8-yl, 4H-1,4-benzoxazin-5-yl, 4H-1,4-benzoxazin-6-yl, 4H-1,4-benzoxazin-7-yl, 4H-1,4-benzoxazin-8-yl, 4H-1,4-benzthiazin-5-yl, 4H-1,4-benzthiazin-6-yl, 4H-1,4-benzthiazin-7-yl, 4H-1,4-benzthiazin-8-yl, 1,4H-1,4-benzdiazin-5-yl, 1,4H-1,4-benzdiazin-6-yl, 1,4H-1,4-benzdiazin-7-yl, 1,4H-1,4-benzdiazin-8-yl, indol-4-yl, indol-5-yl, indol-6-yl, indol-7-yl, benzo(b)thiophen-4yl, benzo(b)thiophen-5-yl, benzo(b)thiophen-6-yl, benzo(b)thiophen-7-yl, benzofuran-4-yl, benzofuran-5-yl, benzofuran-6-yl, benzofuran-7-yl, benzisoxazol-4-yl, benzisoxazol-5-yl, benzisoxazol-6-yl, benzisoxazol-7-yl, benzoxazol-4-yl, benzoxazol-4-yl, benzoxazol-5-yl, benzoxazol-6-yl and benzoxazol-7-yl. Preferred fused phenylheteroaryl rings include quinolinyl, isoquinolinyl, indolyl, benzo(b)thiophenyl, or benzofuranyl.

The term "(3- to 7-membered)-carbocyclic", as used herein, unless otherwise indicated, means a monocyclic group containing 3 to 7 carbon atoms and optionally containing 1 or 2 double bonds. Examples of such rings include cyclopropyl, cyclobutyl, cyclopentyl, cyclohexyl, cycloheptanyl, cyclopentenyl, cyclohexenyl or cycloheptenyl.

The term "(5- to 7-membered)-carbocyclic", as used herein, unless otherwise indicated, means a monocyclic group containing 5 to 7 carbon atoms and optionally containing 1 or 2 double bonds. Examples of such rings include cyclopentyl, cyclohexyl, cycloheptanyl, cyclopentenyl, cyclohexenyl or cycloheptenyl.

The term "(5- to 7-membered)-carbocyclic fused to a saturated or partially saturated (5- to 7-membered)-carbocyclic ring", as used herein, unless otherwise indicated, means a bicyclic group having a first carbocyclic ring covalently bound to the pyrazole nucleus and wherein said first ring is fused to a second ring comprising a 5 to 7 membered carbocycle, wherein the 5 to 7 members include the carbon atoms common to both rings and wherein said second ring may contain 1, 2 or 3 double bonds. Examples of such rings, wherein the fusion is so called ortho fused, include tetralin-1-yl, tetralin-2-yl, hexahydronaphthalen-1-yl, hexahydronaphthalen-2-yl, octahydronaphthalen-1-yl, octahydronaphthalen-2-yl, decalin-1-yl, decalin-2-yl, 4,5,6,7-tetrahydro-indan-4-yl, 4,5,6,7-tetrahydro-indan-5-yl, 4,5,6,7,8,9-hexahydro-indan-4-yl, 4,5,6,7,8,9-hexahydro-indan-5-yl, 4,5,6,7-tetrahydro-inden-4-yl, 4,5,6,7-tetrahydro-inden-5-yl, 4,5,6,7,8,9-hexahydro-inden-4-yl, 4,5,6,7,8,9-hexahydro-inden-5-yl, pentalan-1-yl, pentalan-2-yl , 4,5 dihydro-pentalan-1-yl, 4,5 dihydro-pentalan-2-yl, 4,5,6,7tetrahydro-pentalan-1-yl, 4,5,6,7 tetra-pentalan-2-yl, benzocycloheptan-5-yl, benzocycloheptan-6-yl and the like. Examples of such bicyclic rings that are not ortho fused include bicyclo[3.2.1]-octan-2-yl, bicyclo[3.2.1]-octan-3-yl, bicyclo [5.2.0]nonan-2-yl, bicyclo [5.2.0]nonan-3-yl, bicyclo [5.2.0]nonan-4-yl, bicyclo [4.3.2]undecan-7-yl, bicyclo [4.3.2]undecan-8-yl, bicyclo [4.3.2]undecan-9-yl, bicyclo [2.2.2]-octan-2-yl, bicyclo[2.2.2]-octan-3-yl, bicyclo[2.2.1]-heptan-2-yl, bicyclo[3.1.1]-heptan-2-yl, or borneol-2-yl.

The term "(5- to 7-membered)carbocyclic fused to a saturated, partially saturated or aromatic (5- to 6-membered)-heterocyclic", as used herein, unless otherwise indicated, means a bicyclic group having a first carbocyclic ring covalently bound to the pyrazole nucleus and wherein said first ring is fused to a second ring comprising a 5 to 6 membered heterocyclic ring, wherein said second 5 to 6 members include the atoms common to both rings. Said second ring comprises a saturated, partially saturated or aromatic (5- to 6-membered)-heterocyclic ring. Examples of said bicyclic ring systems are 5,6,7,8 tetrahydro-quinolin-5-yl, 5,6,7,8 tetrahydro-quinolin-6-yl, 5,6,7,8 tetrahydro-quinolin-7-yl, 5,6,7,8 tetrahydro-quinolin-8-yl, 5,6,7,8 tetrahydro-isoquinolin-5-yl, 5,6,7,8 tetrahydro-isoquinolin-6-yl, 5,6,7,8 tetrahydro-isoquinolin-7-yl, 5,6,7,8 tetrahydro-isoquinolin-8-yl, 5,6,7,8 tetrahydro-quinazolin-5-yl, 5,6,7,8 tetrahydro-quinazolin-6-yl, 5,6,7,8 tetrahydro-quinazolin-7-yl, 5,6,7,8 tetrahydro-quinazolin-8-yl, 5,6,7,8 tetrahydro-4H-1,4-benzoxazin-5-yl, 5,6,7,8 tetrahydro-4H-1,4-benzoxazin-6-yl, 5,6,7,8 tetrahydro-4H-1,4-benzoxazin-7-yl, 5,6,7,8 tetrahydro-4H-1,4-benzoxazin-8-yl, 5,6,7,8 tetrahydro-4H-1,4-benzthiazin-5-yl, 5,6,7,8 tetrahydro-4H-1,4-benzthiazin-6-yl, 5,6,7,8 tetrahydro-4H-1,4-benzthiazin-7-yl, 5,6,7,8 tetrahydro-4H-1,4-benzthiazin-8-yl, 5,6,7,8 tetrahydro-1,4H-1,4-benzdiazin-5-yl, 5,6,7,8 tetrahydro-1,4H-1,4-benzdiazin-6-yl, 5,6,7,8 tetrahydro-1,4H-1,4-benzdiazin-7-yl, 5,6,7,8 tetrahydro-1,4H-1,4-benzdiazin-8-yl, 4,5,6,7 tetrahydro-indol-4-yl, 4,5,6,7 tetrahydro indol-5-yl, 4,5,6,7 tetrahydro-indol-6-yl, 4,5,6,7 tetrahydro-indol-7-yl, 4,5,6,7 tetrahydro-benzo(b)thiophen-4-yl, 4,5,6,7 tetrahydro-benzo(b)thiophen-5-yl, 4,5,6,7 tetrahydro-benzo(b)thiophen-6-yl, 4,5,6,7 tetrahydro-benzo(b)thiophen-7-yl, 4,5,6,7 tetrahydro-benzofuran-4-yl, 4,5,6,7 tetrahydro-benzofuran-5-yl, 4,5,6,7 tetrahydro-benzofuran-6-yl, 4,5,6,7 tetrahydro-benzofuran-7-yl, 4,5,6,7 tetrahydro-benzisoxazol-4-yl, 4,5,6,7 tetrahydro-benzisoxazol-5-yl, 4,5,6,7 tetrahydro-benzisoxazol-6-yl, 4,5,6,7 tetrahydro-benzisoxazol-7-yl, 4,5,6,7 tetrahydro-benzoxazol-4-yl, 4,5,6,7 tetrahydro-benzoxazol-4-yl, 4,5,6,7 tetrahydro-benzoxazol-5-yl, 4,5,6,7 tetrahydro-benzoxazol-6-yl, or 4,5,6,7 tetrahydro-benzoxazol-7-yl.

The term "saturated, partially saturated or aromatic (5- to 6-membered)heterocyclic containing 1 to 4 ring heteroatoms independently selected from —N=, —NR$^2$—, —O—, or —S—", as used herein, unless otherwise indicated, means a monocyclic (5- to 6-membered)heterocyclic ring covalently bound to the pyrazole nucleus. Said ring may contain optional double bonds so as to include saturated, partially saturated or aromatic (5- to 6-membered)-heterocyclic rings. Examples of the monocyclic aromatic ring systems are furyl, thienyl, pyrrolyl, pyrazolyl, imidazolyl, triazolyl, tetrazolyl, isoxazolyl, oxazolyl, thiazolyl, isothiazolyl, oxadiazolyl, oxatriazolyl, pyridyl, pyridazinyl, pyrimidinyl, pyrazinyl, triazinyl, and the like. Examples of said monocyclic saturated or partially saturated ring systems are piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholine, 1,2-tetrahydrothiazin-2-yl, 1,3-tetrahydrothiazin-3-yl, tetrahydrothiadiazine, morpholine, 1,2-tetrahydrodiazin-2-yl, 1,3-tetrahydrodiazin-1-yl, 1,4-oxazin-2-yl, or 1,2,5-oxathiazin-4-yl.

The term "saturated, partially saturated or aromatic (5- to 6-membered)heterocyclic fused to a saturated, partially saturated or aromatic (5- to 7-membered)-carbocyclic ring", as used herein, unless otherwise indicated, means a bicyclic group having a first (5- to 6-membered)heterocyclic ring covalently bound to the pyrazole nucleus and wherein said first ring is fused to a second ring comprising a 5 to 6 membered heterocyclic ring, wherein said second 5 to 6 members include the atoms common to both rings. Said first and second rings comprise saturated, partially saturated or aromatic (5- to 6-membered)-heterocyclic rings. Examples of said bicyclic ring systems are indolidin-4-yl, indolidin-5-yl, quinolidin-5-yl, quinolidin-6-yl, quinolidin-7-yl, quinolidin-8-yl, isoquinolidin-5-yl, isoquinolidin-6-yl, isoquinolidin-7-yl, isoquinolidin-8-yl, quinazolidin-5-yl, quinazolidin-6-yl, quinazolidin-7-yl, quinazolidin-8-yl, benzofuran-2-yl, benzofuran-3-yl, isobenzofuran-1-yl, isobenzofuran-3-yl, benzothiophen-2-yl, benzothiophen-3-yl, indol-2-yl, indol-3-yl, isoindol-1-yl, isoindol-3-yl, cyclopentapyrid-2-yl, cyclopentapyrid-3-yl, benzoxazol-2-yl, or cinnolin-4-yl.

The term "saturated, partially saturated or aromatic (5- to 6-membered)heterocyclic fused to a saturated, partially saturated or aromatic (5- to 6-membered)-heterocyclic" as used herein, unless otherwise indicated, means a bicyclic heterocyclic group having a first ring covalently bound to the pyrazole nucleus and containing five to six ring atoms comprising one to two heteroatoms each independently selected from —N=, —NH—, —[N—(C$_1$–C$_4$)alkyl]-, —O— and —S—; wherein said first ring is fused to a second ring comprising a 5 to 6 membered heterocyclic ring, wherein said second 5 to 6 members include the atoms common to both rings. Said second ring comprises a saturated, partially saturated or aromatic (5- to 6-membered)-heterocyclic ring. Examples of said bicyclic ring systems are pyrano[3,4b]pyrrolyl, pyrano[3,2b]pyrrolyl, pyrano[4,3b]pyrrolyl, purin-2-yl, purin-6-yl, purin-7-yl, purin-8-yl, pteridin-2-yl, pyrido[3,4b]pyridyl, pyrido[3,2b]pyridyl, pyrido[4,3b]pyridyl, or naphthyridinyl.

An embodiment and a preferred group of compounds of the present invention includes compounds of formula 1, referred to as the IA1 group of compounds, wherein said compounds have the formula

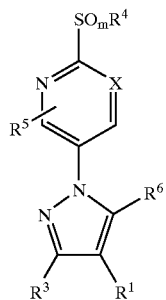

IA1 wherein X is $CR^7$ or N, preferably $CR^7$ wherein $R^7$ is hydrogen; and wherein m is preferably 2.

A preferred group of compounds of the present invention includes compounds of formula I, referred to as the IA2 group of compounds, wherein said compounds have the formula

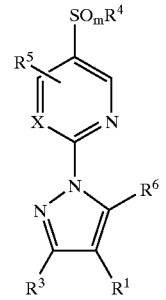

IA2 wherein X is $CR^7$ or N, wherein X is $CR^7$ or N, preferably $CR^7$ wherein $R^7$ is hydrogen hydrogen; and wherein m is preferably 2.

An embodiment of the present invention includes compounds of formula I, referred to as the IA3 group of compounds, wherein said compounds have the formula

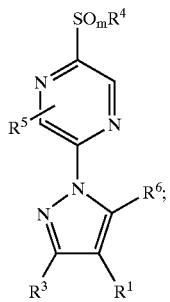

IA3 wherein $R^1$, $R^3$, $R^4$, $R^5$ and $R^6$ are as defined above hydrogen; and wherein m is preferably 2.

An embodiment of the present invention includes compounds of formula I, referred to as the IA4 group of compounds, wherein said compounds have the formula

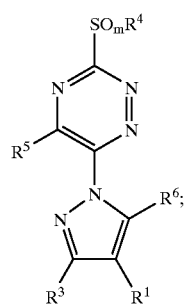

IA4 wherein $R^1$, $R^3$, $R^4$, $R^5$ and $R^6$ are as defined above hydrogen; and wherein m is preferably 2.

An embodiment of the present invention includes compounds of formula I, referred to as the IA5 group of compounds, wherein said compounds have the formula

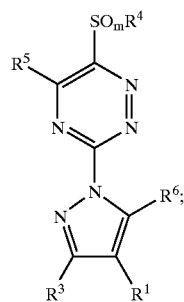

IA5 wherein $R^1$, $R^3$, $R^4$, $R^5$ and $R^6$ are as defined above hydrogen; and wherein m is preferably 2.

An embodiment of the present invention includes compounds of formula I, referred to as the IA6 group of compounds, wherein said compounds have the formula

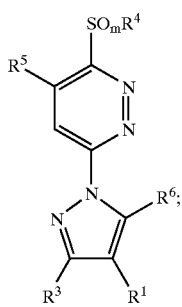

IA6 wherein $R^1$, $R^3$, $R^4$, $R^5$ and $R^6$ are as defined above hydrogen; and wherein m is preferably 2.

An embodiment and a preferred group of compounds of the present invention includes compounds of formula I, referred to as the $R^6$ (a) group of compounds, wherein $R^6$ is (a) phenyl optionally substituted by one to three, preferably one, substituents independently selected from the group consisting of halo (preferably fluoro), hydroxy, cyano, mercapto, hydroxycarbonyl, nitro, $(C_1-C_6)$alkyl (preferably methyl), $(C_2-C_6)$alkenyl, $(C_2-C_6)$alkynyl, $(C_3-C_7)$ carbocyclyl, $(C_1-C_6)$alkoxy, —$OCF_3$, $(C_1-C_6)$alkylthio, $(C_1-C_6)$alkyl-S(=O)—, $(C_1-C_6)$alkyl-$SO_2$—, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$ heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N—$(C_6-C_{10})$arylamido, N—$(C_1-C_6)$ alkoxyamido, $(C_1-C_6)$alkylcarbonyloxy, $(C_1-C_6)$ alkylcarbonyl-N($R^2$)—, formyl, $(C_1-C_6)$alkylcarbonyl, $(C_1-C_6)$alkoxycarbonyl, $(C_6-C_{10})$aryl and $(C_2-C_9)$ heterocyclyl; preferably halo, most preferably one fluoro atom, or $(C_1-C_6)$alkyl, most preferably methyl;

wherein each of said $R^6$ (a) $(C_1-C_6)$alkyl group wherever they occur may optionally be substituted with one to three substituents independently selected from the group consisting of halo, hydroxy, $(C_2-C_6)$alkenyl, $(C_2-C_6)$alkynyl, $(C_3-C_7)$carbocyclyl, $(C_1-C_6)$alkoxy, carbonyl, formyl, formamidyl, $(C_1-C_6)$alkylcarbonyl, cyano, mercapto, nitro, hydroxycarbonyl, $(C_1-C_6)$alkoxycarbonyl, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$ heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N—$(C_6-C_{10})$arylamido, $(C_1-C_6)$ alkoxyamido, $(C_6-C_{10})$aryl, $(C_6-C_{10})$aryloxy, $(C_2-C_9)$ heteroaryl, $(C_2-C_9)$heteroaryloxy, $(C_2-C_9)$ heteroarylcarbonyl, $(C_1-C_6)$alkylthio, $(C_1-C_6)$alkyl-S (=O)—, $(C_1-C_6)$alkyl-$SO_2$—, $(C_1-C_6)$alkylcarbonyl-N ($R^2$)—, and $(C_1-C_6)$alkylcarbonyloxy.

A preferred embodiment of the $R^6$ (a) group of compounds includes compounds of formula I wherein $R^6$ is phenyl optionally substituted by one to three, preferably one, substituents independently selected from the group consisting of halo, most preferably chloro, or $(C_1-C_6)$alkyl, most preferably methyl;

wherein each of said $R^6$ (a) $(C_1-C_6)$alkyl group wherever they occur may optionally be substituted with one to three substituents independently selected from the group consisting of halo, hydroxy, $(C_2-C_6)$alkenyl, $(C_2-C_6)$alkynyl, $(C_3-C_7)$carbocyclyl, $(C_1-C_6)$alkoxy, carbonyl, formyl, formamidyl, $(C_1-C_6)$alkylcarbonyl, cyano, mercapto, nitro, hydroxycarbonyl, $(C_1-C_5)$alkoxycarbonyl, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$ heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N—$(C_6-C_{10})$arylamido, $(C_1-C_6)$ alkoxyamido, $(C_6-C_{10})$aryl, $(C_6-C_{10})$aryloxy, $(C_2-C_9)$ heteroaryl, $(C_2-C_9)$heteroaryloxy, $(C_2-C_9)$ heteroarylcarbonyl, $(C_1-C_6)$alkylthio, $(C_1-C_6)$alkyl-S (=O)—, $(C_1-C_6)$alkyl-$SO_2$—, $(C_1-C_6)$alkylcarbonyl-N ($R^2$)—, and $(C_1-C_6)$alkylcarbonyloxy.

Another preferred embodiment of the $R^6$ (a) group of compounds includes compounds of formula I wherein $R^6$ is phenyl optionally substituted with one to three, preferably one, halo, preferably chloro, or one to three, preferably one, $(C_1-C_6)$alkyl, preferably methyl.

Another preferred embodiment of the $R^6$ (a) group of compounds includes compounds of formula I wherein $R^6$ is unsubstituted phenyl.

An embodiment of the present invention includes compounds of formula I, referred to as the $R^6$ (b) group of compounds, wherein $R^6$ is (b) phenyl fused to a saturated, partially saturated or aromatic (5- to 7-membered)-carbocyclic ring;

wherein either of said phenyl or said fused saturated, partially saturated or aromatic (5- to 7-membered)-carbocyclic ring is optionally substituted by one to two substituents per ring, wherein said substituents are independently selected from the group consisting of halo, hydroxy, cyano, mercapto, hydroxycarbonyl, nitro, $(C_1-C_6)$alkyl, $(C_2-C_6)$alkenyl, $(C_2-C_6)$alkynyl, $(C_3-C_7)$carbocyclyl, $(C_1-C_6)$alkoxy, —$OCF_3$, $(C_1-C_6)$alkylthio, $(C_1-C_6)$alkyl-S (=O)—, $(C_1-C_6)$alkyl-$SO_2$—, amino, N—$(C_1-C_6)$ alkylamino, N,N—[$(C_1-C_6)$alkyl]$_2$amino, N—$(C_3-C_7)$ carbocyclylamino, N—$(C_6-C_{10})$arylamino, N—$(C_1-C_6)$ alkyl-N—$(C_6-C_{10})$arylamino, N—$(C_2-C_9)$ heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N—$(C_6-C_{10})$arylamido, N—$(C_1-C_6)$ alkoxyamido, $(C_1-C_6)$alkylcarbonyloxy, $(C_1-C_6)$ alkylcarbonyl-N($R^2$)—, formyl, $(C_1-C_6)$alkylcarbonyl, $(C_1-C_6)$alkoxycarbonyl, $(C_6-C_{10})$aryl and $(C_2-C_9)$ heterocyclyl;

wherein each of said $R^6$ (b) $(C_1-C_6)$alkyl group wherever they occur may optionally be substituted with one to three substituents independently selected from the group consisting of halo, hydroxy, $(C_2-C_6)$alkenyl, $(C_2-C_6)$alkynyl, $(C_3-C_7)$carbocyclyl, $(C_1-C_6)$alkoxy, carbonyl, formyl, formamidyl, $(C_1-C_6)$alkylcarbonyl, cyano, mercapto, nitro, hydroxycarbonyl, $(C_1-C_6)$alkoxycarbonyl, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$ heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N—$(C_6-C_{10})$arylamido, $(C_1-C_6)$ alkoxyamido, $(C_6-C_{10})$aryl, $(C_6-C_{10})$aryloxy, $(C_2-C_9)$ heteroaryl, $(C_2-C_9)$heteroaryloxy, $(C_2-C_9)$ heteroarylcarbonyl, $(C_1-C_6)$alkylthio, $(C_1-C_6)$alkyl-S (=O)—, $(C_1-C_6)$alkyl-$SO_2$—, $(C_1-C_6)$alkylcarbonyl-N ($R^2$)—, and $(C_1-C_6)$alkylcarbonyloxy.

An embodiment of the present invention includes compounds of formula I, referred to as the $R^6$ (c) group of compounds, wherein $R^6$ is (c) phenyl fused to a saturated, partially saturated or aromatic (5- to 6-membered)-heterocyclyl containing one to two ring heteroatoms independently selected from the group consisting of —N=, —NR$^2$—, —S— and —O—;

wherein either of said phenyl or said fused saturated, partially saturated or aromatic (5- to 6-membered)-heterocyclyl is optionally substituted with one to two substituents per ring;

wherein said substituents are independently selected from the group consisting of halo, hydroxy, cyano, mercapto, hydroxycarbonyl, nitro, ($C_1$–$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —OCF$_3$, ($C_1$–$C_6$)alkylthio, ($C_1$–$C_6$) alkyl-S(=O)—, ($C_1$–$C_6$)alkyl-SO$_2$—, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, N—($C_1$–$C_6$)alkoxyamido, ($C_1$–$C_6$)alkylcarbonyloxy, ($C_1$–$C_6$)alkylcarbonyl-N(R$^2$)—, formyl, ($C_1$–$C_6$)alkylcarbonyl, ($C_1$–$C_6$)alkoxycarbonyl, ($C_6$–$C_{10}$)aryl and ($C_2$–$C_9$)heterocyclyl;

wherein each of said R$^6$ (c) ($C_1$–$C_6$)alkyl group wherever they occur may optionally be substituted with one to three substituents independently selected from the group consisting of halo, hydroxy, ($C_2$–$C_6$)alkenyl, ($C_2$–$C_6$)alkynyl, ($C_3$–$C_7$)carbocyclyl, ($C_1$–$C_6$)alkoxy, carbonyl, formyl, formamidyl, ($C_1$–$C_6$)alkylcarbonyl, cyano, mercapto, nitro, hydroxycarbonyl, ($C_1$–$C_6$)alkoxycarbonyl, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, ($C_1$–$C_6$)alkoxyamido, ($C_6$–$C_{10}$)aryl, ($C_6$–$C_{10}$)aryloxy, ($C_2$–$C_9$)heteroaryl, ($C_2$–$C_9$)heteroaryloxy, ($C_2$–$C_9$)heteroarylcarbonyl, ($C_1$–$C_6$)alkylthio, ($C_1$–$C_6$)alkyl-S(=O)—, ($C_1$–$C_6$)alkyl-SO$_2$—, ($C_1$–$C_6$)alkylcarbony-N(R$^2$)—, and ($C_1$–$C_6$)alkylcarbonyloxy.

An embodiment of the present invention includes compounds of formula I, referred to as the R$^6$ (d) group of compounds, wherein R$^6$ is (d) (3- to 7-membered)-carbocyclic optionally containing one or two double bonds, preferably the (3- to 7-membered)-carbocyclic contains no double bonds;

wherein said (3- to 7-membered)-carbocyclic may also be optionally substituted by one to three substituents independently selected from the group consisting of halo, hydroxy, cyano, mercapto, hydroxycarbonyl, nitro, ($C_1$–$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —OCF$_3$, ($C_1$–$C_6$)alkylthio, ($C_1$–$C_6$)alkyl-S(=O)—, ($C_1$–$C_6$)alkyl-SO$_2$—, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, N—($C_1$–$C_6$)alkoxyamido, ($C_1$–$C_6$)alkylcarbonyloxy, ($C_1$–$C_6$)alkylcarbonyl-N(R$^2$)—, formyl, ($C_1$–$C_6$)alkylcarbonyl, ($C_1$–$C_6$)alkoxycarbonyl, ($C_6$–$C_{10}$)aryl and ($C_2$–$C_9$)heterocyclyl;

wherein each of said R$^6$ (d) ($C_1$–$C_6$)alkyl group wherever they occur may optionally be substituted with one to three substituents independently selected from the group consisting of halo, hydroxy, ($C_2$–$C_6$)alkenyl, ($C_2$–$C_6$)alkynyl, ($C_3$–$C_7$)carbocyclyl, ($C_1$–$C_6$)alkoxy, carbonyl, formyl, formamidyl, ($C_1$–$C_6$)alkylcarbonyl, cyano, mercapto, nitro, hydroxycarbonyl, ($C_1$–$C_6$)alkoxycarbonyl, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, ($C_1$–$C_6$)alkoxyamido, ($C_6$–$C_{10}$)aryl, ($C_6$–$C_{10}$)aryloxy, ($C_2$–$C_9$)heteroaryl, ($C_2$–$C_9$)heteroaryloxy, ($C_2$–$C_9$)heteroarylcarbonyl, ($C_1$–$C_6$)alkylthio, ($C_1$–$C_6$)alkyl-S(=O)—, ($C_1$–$C_6$)alkyl-SO$_2$—, ($C_1$–$C_6$)alkylcarbonyl-N(R$^2$)—, and ($C_1$–$C_6$)alkylcarbonyloxy.

Another embodiment of the R$^6$ (d) group of compounds includes compounds of formula I wherein R$^6$ is cyclohexyl optionally substituted by one substituent independently selected from the group consisting of halo, such as chloro, or ($C_1$–$C_6$)alkyl, such as methyl.

An embodiment of the present invention includes compounds of formula I, referred to as the R$^6$ (e) group of compounds, wherein R$^6$ is (e) (5- to 7-membered)-carbocyclic fused to a saturated, partially saturated or aromatic (5- to 7-membered)-carbocyclic ring;

wherein said (5- to 7-membered)-carbocyclic may optionally contain one or two double bonds;

wherein either of said (5- to 7-membered)-carbocyclic or said fused saturated, partially saturated or aromatic (5- to 7-membered)-carbocyclic ring is optionally substituted by one to two substituents per ring, wherein said substituents are independently selected from the group consisting of halo, hydroxy, cyano, mercapto, hydroxycarbonyl, nitro, ($C_1$–$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —OCF$_3$, ($C_1$–$C_6$)alkylthio, ($C_1$–$C_6$)alkyl-S(=O)—, ($C_1$–$C_6$)alkyl-SO$_2$—, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, N—($C_1$–$C_6$)alkoxyamido, ($C_1$–$C_6$)alkylcarbonyloxy, ($C_1$–$C_6$)alkylcarbonyl-N(R$^2$)—, formyl, ($C_1$–$C_6$)alkylcarbonyl, ($C_1$–$C_6$)alkoxycarbonyl, ($C_6$–$C_{10}$)aryl and ($C_2$–$C_9$)heterocyclyl;

wherein each of said R$^6$ (e) ($C_1$–$C_6$)alkyl group wherever they occur may optionally be substituted with one to three substituents independently selected from the group consisting of halo, hydroxy, ($C_2$–$C_6$)alkenyl, ($C_2$–$C_6$)alkynyl, ($C_3$–$C_7$)carbocyclyl, ($C_1$–$C_6$)alkoxy, carbonyl, formyl, formamidyl, ($C_1$–$C_6$)alkylcarbonyl, cyano, mercapto, nitro, hydroxycarbonyl, ($C_1$–$C_6$)alkoxycarbonyl, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, ($C_1$–$C_6$)alkoxyamido, ($C_6$–$C_{10}$)aryl, ($C_6$–$C_{10}$)aryloxy, ($C_2$–$C_9$)heteroaryl, ($C_2$–$C_9$)heteroaryloxy, ($C_2$–$C_9$)heteroarylcarbonyl, ($C_1$–$C_6$)alkylthio, ($C_1$–$C_6$)alkyl-S(=O)—, ($C_1$–$C_6$)alkyl-SO$_2$—, ($C_1$–$C_6$)alkylcarbonyl-N(R$^2$)—, and ($C_1$–$C_6$)alkylcarbonyloxy.

An embodiment of the present invention includes compounds of formula I, referred to as the R$^6$ (f) group of compounds, wherein R$^6$ is (f) (5- to 7-membered)-carbocyclic fused to a saturated, partially saturated or aromatic (5- to 6-membered)-heterocyclyl containing one to two ring heteroatoms independently selected from the group consisting of —N=, —NR$^2$—, —S— and —O—;

wherein said (5- to 7-membered)-carbocyclic may optionally contain one or two double bonds;

wherein either of said (5- to 7-membered)-carbocyclic or said fused saturated, partially saturated or aromatic (5- to 6-membered)-heterocyclyl is optionally substituted with one to two substituents per ring;

wherein said substituents are independently selected from the group consisting of halo, hydroxy, cyano, mercapto, hydroxycarbonyl, nitro, ($C_1$-$C_6$)alkyl, ($C_2$-$C_6$)alkenyl, ($C_2$-$C_6$)alkynyl, ($C_3$-$C_7$)carbocyclyl, ($C_1$-$C_6$)alkoxy, —OCF$_3$, ($C_1$-$C_6$)alkylthio, ($C_1$-$C_6$)alkyl-S(=O)—, ($C_1$-$C_6$)alkyl-SO$_2$—, amino, N—($C_1$-$C_6$)alkylamino, N,N—[($C_1$-$C_6$)alkyl]$_2$amino, N—($C_3$-$C_7$)carbocyclylamino, N—($C_6$-$C_{10}$)arylamino, N—($C_1$-$C_6$)alkyl-N—($C_1$-$C_{10}$)arylamino, N—($C_2$-$C_9$)heteroarylamino, amido, N—($C_1$-$C_6$)alkylamido, N,N—[($C_1$-$C_6$)alkyl]$_2$amido, N—($C_6$-$C_{10}$)arylamido, N—($C_1$-$C_6$)alkyl-N—($C_6$-$C_{10}$)arylamido, N—($C_1$-$C_6$)alkoxyamido, ($C_1$-$C_6$)alkylcarbonyloxy, ($C_1$-$C_6$)alkylcarbonyl-N(R$^2$)—, formyl, ($C_1$-$C_6$)alkylcarbonyl, ($C_1$-$C_6$)alkoxycarbonyl, ($C_6$-$C_{10}$)aryl and ($C_2$-$C_9$)heterocyclyl;

wherein each of said R$^6$ (f) ($C_1$-$C_6$)alkyl group wherever they occur may optionally be substituted with one to three substituents independently selected from the group consisting of halo, hydroxy, ($C_2$-$C_6$)alkenyl, ($C_2$-$C_6$)alkynyl, ($C_3$-$C_7$)carbocyclyl, ($C_1$-$C_6$)alkoxy, carbonyl, formyl, formamidyl, ($C_1$-$C_6$)alkylcarbonyl, cyano, mercapto, nitro, hydroxycarbonyl, ($C_1$-$C_6$)alkoxycarbonyl, amino, N—($C_1$-$C_6$)alkylamino, N,N—[($C_1$-$C_6$)alkyl]$_2$amino, N—($C_3$-$C_7$)carbocyclylamino, N—($C_6$-$C_{10}$)arylamino, N—($C_1$-$C_6$)alkyl-N—($C_6$-$C_{10}$)arylamino, N—($C_2$-$C_9$)heteroarylamino, amido, N—($C_1$-$C_6$)alkylamido, N,N—[($C_1$-$C_6$)alkyl]$_2$amido, N—($C_6$-$C_{10}$)arylamido, N—($C_1$-$C_6$)alkyl-N—($C_6$-$C_{10}$)arylamido, ($C_1$-$C_6$)alkoxyamido, ($C_6$-$C_{10}$)aryl, ($C_6$-$C_{10}$)aryloxy, ($C_2$-$C_9$)heteroaryl, ($C_2$-$C_9$)heteroaryloxy, ($C_2$-$C_9$)heteroarylcarbonyl, ($C_1$-$C_6$)alkylthio, ($C_1$-$C_6$)alkyl-S(=O)—, ($C_1$-$C_6$)alkyl-SO$_2$—, ($C_1$-$C_6$)alkylcarbonyl-N(R$^2$)—, and ($C_1$-$C_6$)alkylcarbonyloxy.

An embodiment of the present invention includes compounds of formula I, referred to as the R$^6$ (g) group of compounds, wherein R$^6$ is (g) saturated, partially saturated or aromatic, preferably aromatic, (5- to 6-membered)-heterocyclyl containing one to four, preferably one, ring heteroatom(s) independently selected from the groups consisting of —N=, —NR$^2$—, —O—, and —S—, preferably selected from the group consisting of —O—, and —S—;

wherein said (5- to 6-membered)-heterocyclyl is optionally substituted by one to three substituents independently selected from the group consisting of halo, hydroxy, cyano, mercapto, hydroxycarbonyl, nitro, ($C_1$-$C_6$)alkyl, ($C_2$-$C_6$)alkenyl, ($C_2$-$C_6$)alkynyl, ($C_3$-$C_7$)carbocyclyl, ($C_1$-$C_6$)alkoxy, —OCF$_3$, ($C_1$-$C_6$)alkylthio, ($C_1$-$C_6$)alkyl-S(=O)—, ($C_1$-$C_6$) alkyl-SO$_2$—, amino, N—($C_1$-$C_6$)alkylamino, N,N—[($C_1$-$C_6$)alkyl]$_2$amino, N—($C_3$-$C_7$)carbocyclylamino, N—($C_6$-$C_{10}$)arylamino, N—($C_1$-$C_6$)alkyl-N—($C_6$-$C_{10}$)arylamino, N—($C_2$-$C_9$)heteroarylamino, amido, N—($C_1$-$C_6$)alkylamido, N,N—[($C_1$-$C_6$)alkyl]$_2$amido, N—($C_6$-$C_{10}$)arylamido, N—($C_1$-$C_6$)alkyl-N—($C_6$-$C_{10}$)arylamido, ($C_1$-$C_6$)alkoxyamido, ($C_1$-$C_6$)alkylcarbonyloxy, ($C_1$-$C_6$)alkylcarbonyl-N(R$^2$)—, formyl, ($C_1$-$C_6$)alkylcarbonyl, ($C_1$-$C_6$)alkoxycarbonyl, ($C_6$-$C_{10}$)aryl and ($C_2$-$C_9$)heterocyclyl; preferably said (5- to 6-membered)-heterocyclyl is unsubstituted;

wherein each of said R$^6$ (g) ($C_1$-$C_6$)alkyl group wherever they occur may optionally be substituted with one to three substituents independently selected from the group consisting of halo, hydroxy, ($C_2$-$C_6$)alkenyl, ($C_2$-$C_6$)alkynyl, ($C_3$-$C_7$)carbocyclyl, ($C_1$-$C_6$)alkoxy, carbonyl, formyl, formamidyl, ($C_1$-$C_6$)alkylcarbonyl, cyano, mercapto, nitro, hydroxycarbonyl, ($C_1$-$C_6$)alkoxycarbonyl, amino, N—($C_1$-$C_6$)alkylamino, N,N—[($C_1$-$C_6$)alkyl]$_2$amino, N—($C_3$-$C_7$)carbocyclylamino, N—($C_6$-$C_{10}$)arylamino, N—($C_1$-$C_6$)alkyl-N—($C_6$-$C_{10}$)arylamino, N—($C_2$-$C_9$)heteroarylamino, amido, N—($C_1$-$C_6$)alkylamido, N,N—[($C_1$-$C_6$)alkyl]$_2$amido, N—($C_6$-$C_{10}$)arylamido, N—($C_1$-$C_6$)alkyl-N—($C_6$-$C_{10}$)arylamido, ($C_1$-$C_6$)alkoxyamido, ($C_6$-$C_{10}$)aryl, ($C_6$-$C_{10}$)aryloxy, ($C_2$-$C_9$)heteroaryl, ($C_2$-$C_9$)heteroaryloxy, ($C_2$-$C_9$)heteroarylcarbonyl, ($C_1$-$C_6$)alkylthio, ($C_1$-$C_6$)alkyl-S(=O)—, ($C_1$-$C_6$)alkyl-SO$_2$—, ($C_1$-$C_6$)alkylcarbonyl-N(R$^2$)—, and ($C_1$-$C_6$)alkylcarbonyloxy.

Another embodiment of the R$^6$ (g) group of compounds includes compounds of formula I wherein R$^6$ is saturated, partially unsaturated or aromatic, preferably aromatic, (5- to 6-membered), preferably 5-membered, heterocyclyl containing one to four preferably one, ring heteroatoms, independently selected from the groups consisting of —N=, —NR$^2$—, —O—, and —S—, preferably selected from the group consisting of —O—, and —S—;

wherein said (5- to 6-membered)-heterocyclyl is optionally substituted by one to three substituents, preferably no substituents, independently selected from the group consisting of halo, such as chloro, or ($C_1$-$C_6$)alkyl, such as methyl;

wherein each of said R$^6$ (g) ($C_1$-$C_6$)alkyl group wherever they occur may optionally be substituted with one to three substituents independently selected from the group consisting of halo, hydroxy, ($C_2$-$C_6$)alkenyl, ($C_2$-$C_6$)alkynyl, ($C_3$-$C_7$)carbocyclyl, ($C_1$-$C_6$)alkoxy, carbonyl, formyl, formamidyl, ($C_1$-$C_6$)alkylcarbonyl, cyano, mercapto, nitro, hydroxycarbonyl, ($C_1$-$C_6$)alkoxycarbonyl, amino, N—($C_1$-C6)alkylamino, N,N—[($C_1$-$C_6$)alkyl]$_2$amino, N—($C_3$-$C_7$)carbocyclylamino, N—($C_6$-$C_{10}$)arylamino, N—($C_1$-$C_6$)alkyl-N—($C_6$-$C_{10}$)arylamino, N—($C_2$-$C_9$)heteroarylamino, amido, N—($C_1$-$C_6$)alkylamido, N,N—[($C_1$-$C_6$)alkyl]$_2$amido, N—($C_6$-$C_{10}$)arylamido, N—($C_1$-$C_6$)alkyl-N—($C_6$-$C_{10}$)arylamido, ($C_1$-$C_6$)alkoxyamido, ($C_6$-$C_{10}$)aryl, ($C_6$-$C_{10}$)aryloxy, ($C_2$-$C_9$)heteroaryl, ($C_2$-$C_9$)heteroaryloxy, ($C_2$-$C_9$)heteroarylcarbonyl, ($C_1$-$C_6$)alkylthio, ($C_1$-$C_6$)alkyl-S(=O)—, ($C_1$-$C_6$)alkyl-SO$_2$—, ($C_1$-$C_6$)alkylcarbonyl-N(R$^2$)—, and ($C_1$-$C_6$)alkylcarbonyloxy.

Another embodiment of the R$^6$ (g) group of compounds includes compounds of formula I wherein R$^6$ is aromatic (5- to 6-membered)-heterocyclyl containing one to two, preferably one, ring heteroatoms independently selected from the groups consisting of —N=, —NR$^2$—, —O—, and —S—; preferably selected from the group consisting of —O—, and —S—;

wherein said (5- to 6-membered)-heterocyclyl is substituted by one to three, preferably one, halo, preferably chloro, or one to three, preferably one, ($C_1$-$C_6$)alkyl, preferably methyl.

Other preferred embodiment of the R$^6$ (g) group of compounds includes compounds of formula I wherein R$^6$ is unsubstituted aromatic (5- to 6-membered)-, more preferably (5-membered)-heterocyclyl, such as thienyl, most preferably 2-thienyl, or furanyl, most preferably 2-furanyl.

An embodiment of the present invention includes compounds of formula I, referred to as the $R^6$ (h) group of compounds, wherein $R^6$ is (h) saturated, partially saturated or aromatic (5- to 6-membered)-heterocyclyl containing one to two ring heteroatoms independently selected from the group consisting of —N=, —NR$^2$—, —S— and —O—;

wherein said saturated, partially saturated or aromatic (5- to 6-membered)-heterocyclyl is fused to a saturated, partially saturated or aromatic (5- to 7-membered)-carbocyclic ring;

wherein either of said saturated, partially saturated or aromatic (5- to 6-membered)-heterocyclyl ring or said fused saturated, partially saturated or aromatic (5- to 7-membered)-carbocyclic ring is optionally substituted by one to two substituents per ring;

wherein said substituents are independently selected from the group consisting of halo, hydroxy, cyano, mercapto, hydroxycarbonyl, nitro, $(C_1-C_6)$alkyl, $(C_2-C_6)$alkenyl, $(C_2-C_6)$alkynyl, $(C_3-C_7)$carbocyclyl, $(C_1-C_6)$alkoxy, —OCF$_3$, $(C_1-C_6)$alkylthio, $(C_1-C_6)$alkyl-S(=O)—, $(C_1-C_6)$alkyl-SO$_2$—, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N—$(C_6-C_{10})$arylamido, N—$(C_1-C_6)$alkoxyamido, $(C_1-C_6)$alkylcarbonyloxy, $(C_1-C_6)$alkylcarbonyl-N(R$^2$)—, formyl, $(C_1-C_6)$alkylcarbonyl, $(C_1-C_6)$alkoxycarbonyl, $(C_6-C_{10})$aryl and $(C_2-C_9)$heterocyclyl;

wherein each of $R^6$ (h) $(C_1-C_6)$alkyl group wherever they occur may optionally be substituted with one to three substituents independently selected from the group consisting of halo, hydroxy, $(C_2-C_6)$alkenyl, $(C_2-C_6)$alkynyl, $(C_3-C_7)$carbocyclyl, $(C_1-C_6)$alkoxy, carbonyl, formyl, formamidyl, $(C_1-C_6)$alkylcarbonyl, cyano, mercapto, nitro, hydroxycarbonyl, $(C_1-C_6)$alkoxycarbonyl, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N—$(C_6-C_{10})$arylamido, $(C_1-C_6)$alkoxyamido, $(C_6-C_{10})$aryl, $(C_6-C_{10})$aryloxy, $(C_2-C_9)$heteroaryl, $(C_2-C_9)$heteroaryoxy, $(C_2-C_9)$heteroarylcarbonyl, $(C_1-C_6)$alkylthio, $(C_1-C_6)$alkyl-S(=O)—, $(C_1-C_6)$alkyl-SO$_2$—, $(C_1-C_6)$alkylcarbonyl-N(R$^2$)—, and $(C_1-C_6)$alkylcarbonyloxy.

An embodiment of the present invention includes compounds of formula I, referred to as the $R^6$ (i) group of compounds, wherein $R^6$ is (i) saturated, partially saturated or aromatic (5- to 6-membered)-heterocyclyl containing one to two ring heteroatoms independently selected from the group consisting of —N=, —NR$^2$—, —S—, and —O—;

wherein said saturated, partially saturated or aromatic (5- to 6-membered)-heterocyclyl is fused to a saturated, partially saturated or aromatic (5- to 6-membered)-heterocyclyl containing one to two ring heteroatoms independently selected from the group consisting of —N=, —NR$^2$—, —S— and —O—;

wherein either of said saturated, partially saturated or aromatic (5- to 6-membered)-heterocyclyl or said fused saturated, partially saturated or aromatic (5- to 6-membered)-heterocyclyl is optionally substituted with one to twosubstituents per ring;

wherein said substituents are independently selected from the group consisting of halo, hydroxy, cyano, mercapto, hydroxycarbonyl, nitro, $(C_1-C_6)$alkyl, $(C_2-C_6)$alkenyl, $(C_2-C_6)$alkynyl, $(C_3-C_7)$carbocyclyl, $(C_1-C_6)$alkoxy, —OCF$_3$, $(C_1-C_6)$alkylthio, $(C_1-C_6)$alkyl-S(=O)—, $(C_1-C_6)$alkyl-SO$_2$—, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N—$(C_6-C_{10})$arylamido, N—$(C_1-C_6)$alkoxyamido, $(C_1-C_6)$alkylcarbonyloxy, $(C_1-C_6)$alkylcarbonyl-N(R$^2$)—, formyl, $(C_1-C_6)$alkylcarbonyl, $(C_1-C_6)$alkoxycarbonyl, $(C_6-C_{10})$aryl and $(C_2-C_9)$heterocyclyl;

wherein each of said $R^6$ (i) $(C_1-C_6)$alkyl group wherever they occur may optionally be substituted with one to three substituents independently selected from the group consisting of halo, hydroxy, $(C_2-C_6)$alkenyl, $(C_2-C_6)$alkynyl, $(C_3-C_7)$carbocyclyl, $(C_1-C_6)$alkoxy, carbonyl, formyl, formamidyl, $(C_1-C_6)$alkylcarbonyl, cyano, mercapto, nitro, hydroxycarbonyl, $(C_1-C_6)$alkoxycarbonyl, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N—$(C_6-C_{10})$arylamido, $(C_1-C_6)$alkoxyamido, $(C_6-C_{10})$aryl, $(C_6-C_{10})$aryloxy, $(C_2-C_9)$heteroaryl, $(C_2-C_9)$heteroaryloxy, $(C_2-C_9)$heteroarylcarbonyl, $(C_1-C_6)$alkylthio, $(C_1-C_6)$alkyl-S(=O)—, $(C_1-C_6)$alkyl-SO$_2$—, $(C_1-C_6)$alkylcarbonyl-N(R$^2$)—, and $(C_1-C_6)$alkylcarbonyloxy.

Subgeneric embodiments of the present invention of the "A" (i.e. A1, A2, A3, A4, A5, and A6) and $R^6$ (i.e. $R^6$(a), $R^6$(b), $R^6$(c), $R^6$ (d), $R^6$(e), $R^6$(f), $R^6$(g), $R^6$(h), $R^6$(i)) groups of compounds are expressly contemplated by the present invention. Such subgeneric embodiments within the A1 group of compounds include the A1 group in combination with each of the $R^6$ groups (i.e. A1-$R^6$(a), A1-$R^6$(b), A1-$R^6$(c), A1-$R^6$(d), A1-$R^6$(e), A1-$R^6$(f), A1-$R^6$(g), A1-$R^6$(h) and A1-$R^6$(i)). Such subgeneric embodiments within the A2 group of compounds include the A2 group in combination with each of the $R^6$ groups (i.e. A2-$R^6$(a), A2-$R^6$(b), A2-$R^6$(c), A2-$R^6$(d), A2-$R^6$(e), A2-$R^6$(f), A2-$R^6$(g), A2-$R^6$(i)). Such subgeneric embodiments within the A3 group of compounds include the A3 group in combination with each of the $R^6$ groups (i.e. A3-$R^6$(a), A3-$R^6$(b), A3-$R^6$(c), A3-$R^6$(d), A3-$R^6$(e), A3-$R^6$(f), A3-$R^6$(g), A3-$R^6$(h) and A3-$R^6$(i)). Such subgeneric embodiments within the A4 group of compounds include the A4 group in combination with each of the $R^6$ groups (i.e. A4-$R^6$(a), A4-$R^6$(b), A4-$R^6$(c), A4-$R^6$(d), A4-$R^6$(e), A4-$R^6$(f), A4-$R^6$(g), A4-$R^6$(h) and A4-$R^6$(i)). Such subgeneric embodiments within the A5 group of compounds include the A5 group in combination with each of the $R^6$ groups (i.e. A5-$R^6$(a), A5-$R^6$(b), A5-$R^6$(c), A5-$R^6$(d), A5-$R^6$(e), A5-$R^6$(f), A5-$R^6$(g), A5-$R^6$(h) and A5-$R^6$(i)). Such subgeneric embodiments within the A6 group of compounds include the A6 group in combination with each of the $R^6$ groups (i.e. A6-$R^6$(a), A6-$R^6$(b), A6-$R^6$(c), A6-$R^6$(d), A6-$R^6$(e), A6-$R^6$(f), A6-$R^6$(h) and A6-$R^6$(i)).

Preferred compounds of formula I are those compounds wherein the "A" ring is optionally substituted pyridin-2-yl or pyridin-3-yl; more preferably wherein m is 2.

Other compounds of this invention are those of the formula I wherein $R^5$ is hydrogen, halo(such as fluoro), hydroxy, mercapto, $(C_1-C_6)$alkyl, $(C_1-C_6)$alkoxy optionally substituted with one to three halogen atoms, $(C_2-C_6)$alkenyl, $(C_2-C_6)$alkynyl, $(C_3-C_7)$carbocyclyl, cyano, formyl, $(C_1-C_6)$alkylcarbonyl, $(C_1-C_6)$alkylcarbonyloxy, hydroxycarbonyl, $(C_1-C_6)$alkoxycarbonyl, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N—$(C_6-C_{10})$arylamido, N—$(C_1-C_6)$alkoxyamido, or $(C_1-C_6)$alkylthio;

wherein each of said $R^5$ $(C_1-C_6)$alkyl group wherever they occur may optionally be substituted with one to three substituents independently selected from the group consisting of halo, hydroxy, $(C_2-C_6)$alkenyl, $(C_2-C_6)$alkynyl, $(C_3-C_7)$carbocyclyl, $(C_1-C_6)$alkoxy, carbonyl, formyl, formamidyl, $(C_1-C_6)$alkylcarbonyl, cyano, mercapto, nitro, hydroxycarbonyl, $(C_1-C_6)$alkoxycarbonyl, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N—$(C_6-C_{10})$arylamido, $(C_1-C_6)$alkoxyamido, $(C_6-C_{10})$aryl, $(C_6-C_{10})$aryloxy, $(C_2-C_9)$heteroaryl, $(C_2-C_9)$heteroaryloxy, $(C_2-C_9)$heteroarylcarbonyl, $(C_1-C_6)$alkylthio, $(C_1-C_6)$alkyl-S(=O)—, $(C_1-C_6)$alkyl-SO$_2$—, $(C_1-C_6)$alkylcarbonyl-N($R^2$)—, and $(C_1-C_6)$alkylcarbonyloxy.

Other preferred compounds of this invention are those of the formula I wherein $R^5$ is hydrogen.

Other compounds of this invention are those of the formula I wherein $R^4$ is $(C_1-C_6)$alkyl, more preferably methyl, optionally substituted by one to three halo atoms, such as fluoro atoms.

Other preferred compounds of this invention are those of the formula I wherein $R^4$ is $(C_1-C_6)$alkyl, more preferably methyl.

Other compounds of this invention are those of the formula I wherein $R^3$ is $(C_1-C_6)$alkylthio (such as methylthio), $(C_3-C_7)$carbocyclylthio (such as cyclohexylthio), $C_6-C_{10})$arylthio, $(C_2-C_9)$heteroarylthio, $(C_1-C_6)$alkyl-S(=O), $(C_6-C_{10})$aryl-S(=O), $(C_2-C_9)$heteroaryl-S(=O), $(C_1-C_6)$alkyl-SO$_2$—, $(C_6-C_{10})$aryl-SO$_2$—, $(C_2-C_9)$heteroaryl-SO$_2$—, $(C_1-C_6)$alkyl-SO$_2$-amino, $(C_3-C_7)$carbocyclyl-SO$_2$-amino, $(C_6-C_{10})$aryl-SO$_2$-amino, $(C_2-C_9)$heteroaryl-SO$_2$-amino, amino-SO$_2$—, N—$(C_1-C_6)$alkylamino-SO$_2$—, N,N—[$(C_1-C_6)$alkyl]$_2$amino-SO$_2$—, N—$(C_3-C_7)$carbocyclylamino-SO$_2$—, N—$(C_6-C_{10})$arylamino-SO$_2$—, N—$(C_1-C_6)$alkyl-N—$(C_6-C_{10})$arylamino-SO$_2$—, N—$(C_2-C_9)$heteroarylamino-SO$_2$—, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, or N—$(C_2-C_9)$heteroarylamino;

wherein each of said $(C_1-C_6)$alkyl group wherever they occur may optionally be substituted with one to three substituents independently selected from the group consisting of halo, hydroxy, $(C_2-C_6)$alkenyl, $(C_2-C_6)$alkynyl, $(C_3-C_7)$carbocyclyl, $(C_1-C_6)$alkoxy, carbonyl, formyl, formamidyl, $(C_1-C_6)$alkylcarbonyl, cyano, mercapto, nitro, hydroxycarbonyl, $(C_1-C_6)$alkoxycarbonyl, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N—$(C_6-C_{10})$arylamido, $(C_1-C_6)$alkoxyamido, $(C_6-C_{10})$aryl, $(C_6-C_{10})$aryloxy, $(C_2-C_9)$heteroaryl, $(C_2-C_9)$heteroaryloxy, $(C_2-C_9)$heteroarylcarbonyl, $(C_1-C_6)$alkylthio, $(C_1-C_6)$alkyl-S(=O)—, $(C_1-C_6)$alkyl-SO$_2$—, $(C_1-C_6)$alkylcarbonyl-N($R^2$)—, and $(C_1-C_6)$alkylcarbonyloxy.

Other preferred compounds of this invention are those of the formula I wherein $R^3$ is $(C_1-C_6)$alkylthio (such as methylthio), $(C_3-C_7)$carbocyclylthio (such as cyclohexylthio), $(C_2-C_{10})$arylthio, $(C_2-C_9)$heteroarylthio, $(C_1-C_6)$alkyl-S(=O), $(C_6-C_{10})$aryl-S(=O), $(C_2-C_9)$heteroaryl-S(=O), $(C_1-C_6)$alkyl-SO$_2$—, $(C_6-C_{10})$aryl-SO$_2$—, $(C_2-C_9)$heteroaryl-SO$_2$—, $(C_1-C_6)$alkyl-SO$_2$-amino, $(C_3-C_7)$carbocyclyl-SO$_2$-amino, $(C_6-C_{10})$aryl-SO$_2$-amino, $(C_2-C_9)$heteroaryl-SO$_2$-amino, amino-SO$_2$—, N—$(C_1-C_6)$alkylamino-SO$_2$—, N,N—[$(C_1-C_6)$alkyl]$_2$amino-SO$_2$—, N—$(C_3-C_7)$carbocyclylamino-SO$_2$—, N—$(C_6-C_{10})$arylamino-SO$_2$—, N—$(C_1-C_6)$alkyl-N—$(C_6-C_{10})$arylamino-SO$_2$—, N—$(C_2-C_9)$heteroarylamino-SO$_2$—, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, or N—$(C_2-C_9)$heteroarylamino.

Other preferred compounds of this invention are those of the formula I wherein $R^3$ is $(C_1-C_6)$alkylthio (such as methylthio), $(C_3-C_7)$carbocyclylthio (such as cyclohexylthio), $(C_6-C_{10})$arylthio, $(C_2-C_9)$heteroarylthio, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, or N—$(C_2-C_9)$heteroarylamino.

Other preferred compounds of this invention are those of the formula I wherein $R^3$ is $(C_1-C_6)$alkylthio, more preferably methylthio, wherein each of said $(C_1-C_8)$alkyl group may optionally be substituted with one to three substituents independently selected from hydroxycarbonyl or $(C_1-C_6)$alkoxycarbonyl, such as methoxycarbonyl or ethoxycarbonyl.

Other preferred compounds of this invention are those of the formula I wherein $R^3$ is $(C_1-C_6)$alkylthio (more preferably methylthio), amino, alkylsulfonylamino, sulfamylamino, alkylamino and alkylcarbonylamino; more preferably wherein $R^3$ is $(C_1-C_6)$alkylthio or amino.

Other compounds of this invention are those of the formula I wherein $R^2$ is hydrogen, or $(C_1-C_6)$alkyl, such as methyl.

Other compounds of this invention are those of the formula I wherein $R^1$ is hydrogen, cyano, halo, $(C_1-C_6)$alkyl (such as methyl) optionally substituted with one to three halo (such as fluoro) atoms, $(C_1-C_6)$alkylcarbonyl, or formyl.

Other preferred compounds of this invention are those of the formula I wherein $R^1$ is hydrogen, halo, cyano, or $(C_1-C_6)$alkylcarbonyl, such as methylcarbonyl.

Most preferred compounds of this invention are those of the formula I wherein $R^1$ is cyano.

Other most preferred compounds of this invention are those of the formula I wherein the "A" ring is optionally substituted pyridin-2-yl or pyridin-3-yl; more preferably wherein m is 2; $R^1$ is cyano; $R^3$ is methylthio; $R^4$ is methyl; $R^5$ is hydrogen; and $R^6$ is phenyl optionally substituted by one to three, preferably one, substituents independently selected from the group consisting of halo, most preferably chloro, or $(C_1-C_6)$alkyl, most preferably methyl.

Other most preferred compounds of this invention are those of the formula I wherein the "A" ring is optionally substituted pyridin-2-yl or pyridin-3-yl; more preferably wherein m is 2; $R^1$ is cyano; $R^3$ is methylthio; $R^4$ is methyl; $R^5$ is hydrogen; and $R^6$ is phenyl optionally substituted with one to three, preferably one, halo, preferably chloro, or one to three, preferably one, $(C_1-C_6)$alkyl, preferably methyl.

Other most preferred compounds of this invention are those of the formula I wherein the "A" ring is optionally substituted pyridin-2-yl or pyridin-3-yl; more preferably wherein m is 2; $R^1$ is cyano; $R^3$ is methylthio; $R^4$ is methyl; $R^5$ is hydrogen; and $R^6$ is unsubstituted phenyl.

Other most preferred compounds of this invention are those of the formula I wherein the "A" ring is optionally substituted pyridin-2-yl or pyridin-3-yl; more preferably wherein m is 2; $R^1$ is cyano; $R^3$ is methylthio; $R^4$ is methyl; $R^5$ is hydrogen; and $R^6$ is unsubstituted aromatic (5- to 6-membered)-, more preferably (5-membered)-heterocyclyl, such as thienyl, most preferably 2-thienyl, or furanyl, most preferably 2-furanyl.

Examples of specific preferred compounds of the formula I are the following:

1-(5-Methanesulfonyl-pyridin-2-yl)-3-methylsulfanyl-5-phenyl-1H-pyrazole-4-carbonitrile;
5-(4-Chloro-phenyl)-1-(5-methanesulfonyl-pyridin-2-yl)-3-methylsulfanyl-1H-pyrazole-4-carbonitrile;
1-(5-Methanesulfonyl-pyridin-2-yl)-3-methylsulfanyl-5-p-tolyl-1H-pyrazole-4-carbonitrile;
1-(5-Methanesulfonyl-pyridin-2-yl)-3-methylsulfanyl-5-thiophen-2-yl-1H-pyrazole-4-carbonitrile;
1-(5-Methanesulfonyl-pyridin-2-yl)-3-methylsulfanyl-5-m-tolyl-1H-pyrazole-4-carbonitrile;
5-(3-Chloro-phenyl)-1-(5-methanesulfonyl-pyridin-2-yl)-3-methylsulfanyl-1H-pyrazole-4-carbonitrile;
3-Methanesulfonyl-1-(5-methanesulfonyl-pyridin-2-yl)-5-phenyl-1H-pyrazole-4-carbonitrile;
3-Azido-1-(5-methanesulfonyl-pyridin-2-yl)-5-phenyl-1H-pyrazole-4-carbonitrile;
3-Amino-1-(5-methanesulfonyl-pyridin-2-yl)-5-phenyl-1H-pyrazole-4-carbonitrile;
N-[4-Cyano-1-(5-methanesulfonyl-pyridin-2-yl)-5-phenyl-1H-pyrazol-3-yl]-methanesulfonamide;
[4-Cyano-1-(5-methanesulfonyl-pyridin-2-yl)-5-phenyl-1H-pyrazol-3-ylamino]-acetic acid;
[4-Cyano-1-(5-methanesulfonyl-pyridin-2-yl)-5-phenyl-1H-pyrazol-3-ylamino]-acetic acid methyl ester;
1-(6-Methanesulfonyl-pyridin-3-yl)-3-methylsulfanyl-5-phenyl-1H-pyrazole-4-carbonitrile;
3-Methanesulfonyl-1-(6-methanesulfonyl-pyridin-3-yl)-5-phenyl-1H-pyrazole-4-carbonitrile;
3-Methanesulfonyl-1-(6-methanesulfonyl-pyridin-3-yl)-5-phenyl-1H-pyrazole-4-carbonitrile; and the pharmaceutically acceptable salts thereof.

The present invention also relates to a pharmaceutical composition for the treatment of a condition selected from the group consisting of arthritis (including osteoarthritis, degenerative joint disease, spondyloarthropathies, gouty arthritis, systemic lupus erythematosus, juvenile arthritis and rheumatoid arthritis), fever (including rheumatic fever and fever associated with influenza and other viral infections), common cold, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer; hematopoietic malignancies including leukemias and lymphomas; Hodgkin's disease; aplastic anemia, skin cancer and familiar adenomatous polyposis), tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), periarteritis nodosa, congestive heart failure, myocardial infarction, stroke, cerebral ischemia, head trauma, spinal cord injury, neuralgia, neuro-degenerative disorders (acute and chronic), autoimmune disorders, Huntington's disease, Parkinson's disease, migraine, depression, peripheral neuropathy, pain (including low back and neck pain, headache and toothache), gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders (such as psoriasis, eczema, scleroderma and dermatitis), myasthenia gravis, polymyositis, myositis, bursitis, burns, diabetes (including types I and II diabetes, diabetic retinopathy, neuropathy and nephropathy), tumor invasion, tumor growth, tumor metastasis, corneal scarring, scleritis, immunodeficiency diseases (such as AIDS in humans and FLV, FIV in cats), sepsis, premature labor, hypoprothrombinemia, hemophilia, thyroiditis, sarcoidosis, Behcet's syndrome, hypersensitivity, kidney disease, Rickettsial infections (such as Lyme disease, Erlichiosis), Protozoan diseases (such as malaria, giardia, coccidia), reproductive disorders (preferably in livestock), and septic shock in a mammal, preferably a human, cat livestock or a dog, comprising an amount of a compound of formula I or a pharmaceutically acceptable salt thereof effective in such treatment and a pharmaceutically acceptable carrier.

The present invention also relates to a pharmaceutical composition for the treatment of a condition that can be treated by selectively inhibiting COX-2 in a mammal, preferably a human, cat, livestock or dog, comprising a COX-2 selective inhibiting effective amount of a compound of formula I or a pharmaceutically acceptable salt thereof and a pharmaceutically acceptable carrier.

The present invention also relates to a pharmaceutical composition for the treatment of a condition selected from the group consisting of inflammatory diseases such as arthritis (including osteoarthritis, degenerative joint disease, spondyloarthropathies, gouty arthritis, systemic lupus erythematosus, juvenile arthritis and rheumatoid arthritis), or fever (including rheumatic fever and fever associated with influenza).

The present invention also relates to a method for treating a condition selected from the group consisting of arthritis (including osteoarthritis, degenerative joint disease, spondyloarthropathies, gouty arthritis, systemic lupus erythematosus, juvenile arthritis and rheumatoid arthritis), fever (including rheumatic fever and fever associated with influenza and other viral infections), common cold, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer; hematopoietic malignancies including leukemias and lymphomas; Hodgkin's disease; aplastic anemia, skin cancer and familiar adenomatous polyposis), tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), periarteritis nodosa, congestive heart failure, myocardial infarction, stroke, cerebral ischemia, head trauma, spinal cord injury, neuralgia, neuro-degenerative disorders (acute and chronic), autoimmune disorders, Huntington's disease, Parkinson's disease, migraine, depression, peripheral neuropathy, pain (including low back and neck pain, headache and toothache), gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders (such as psoriasis, eczema, scleroderma and dermatitis), myasthenia gravis, polymyositis, myositis, bursitis, burns, diabetes (including types I and II diabetes, diabetic retinopathy, neuropathy and nephropathy), tumor invasion, tumor growth, tumor metastasis, corneal scarring, scleritis, immunodeficiency diseases (such as AIDS in humans and FLV, FIV in cats), sepsis, premature labor, hypoprothrombinemia, hemophilia, thyroiditis, sarcoidosis, Behcet's syndrome, hypersensitivity, kidney disease, Rickettsial infections (such as Lyme disease, Erlichiosis), Protozoan diseases (such as malaria, giardia, coccidia), reproductive disorders (preferably in livestock) and septic shock in a mammal, preferably a human, cat livestock or a dog, comprising administering to said mammal an amount of a compound of formula I or a pharmaceutically acceptable salt thereof effective in treating such a condition.

The present invention also relates to a method for treating a disorder or condition that can be treated by selectively inhibiting COX-2 in a mammal, preferably a human, cat livestock or a dog, comprising administering to a mammal requiring such treatment a COX-2 selective inhibiting effective amount of a compound of formula I or a pharmaceutically acceptable salt thereof.

The present invention also relates to a method for treating a condition selected from the group consisting of inflammatory diseases such as arthritis (including osteoarthritis, degenerative joint disease, spondyloarthropathies, gouty arthritis, systemic lupus erythematosus, juvenile arthritis and rheumatoid arthritis), or fever (including rheumatic fever and fever associated with influenza).

This invention also relates to a method of or a pharmaceutical composition for treating inflammatory processes and diseases comprising administering a compound of formula I of this invention or its salt to a mammal including a human, cat, livestock or dog, wherein said inflammatory processes and diseases are defined as above, and said inhibitory compound is used in combination with one or more other therapeutically active agents under the following conditions:

A.) where a joint has become seriously inflamed as well as infected at the same time by bacteria, fungi, protozoa, and/or virus, said inhibitory compound is administered in combination with one or more antibiotic, antifungal, antiprotozoal, and/or antiviral therapeutic agents;

B.) where a multi-fold treatment of pain and inflammation is desired, said inhibitory compound is administered in combination with inhibitors of other mediators of inflammation, comprising one or more members independently selected from the group consisting essentially of:
(1) NSAIDs;
(2) $H_1$-receptor antagonists;
(3) kinin-$B_1$- and $B_2$-receptor antagonists;
(4) prostaglandin inhibitors selected from the group consisting of PGD-, PGF-$PGI_2$-, and PGE-receptor antagonists;
(5) thromboxane $A_2$ ($TXA_2$-) inhibitors;
(6) 5-, 12- and 15-lipoxygenase inhibitors;
(7) leukotriene $LTC_4$-, $LTD_4/LTE_4$-, and $LTB_4$-inhibitors;
(8) PAF-receptor antagonists;
(9) gold in the form of an aurothio group together with one or more hydrophilic groups;
(10) immunosuppressive agents selected from the group consisting of cyclosporine, azathioprine, and methotrexate;
(11) anti-inflammatory glucocorticoids;
(12) penicillamine;
(13) hydroxychloroquine;
(14) anti-gout agents including colchicine; xanthine oxidase inhibitors including allopurinol; and uricosuric agents selected from probenecid, sulfinpyrazone, and benzbromarone;

C.) where older mammals are being treated for disease conditions, syndromes and symptoms found in geriatric mammals, said inhibitory compound is administered in combination with one or more members independently selected from the group consisting essentially of:
(1) cognitive therapeutics to counteract memory loss and impairment;
(2) anti-hypertensives and other cardiovascular drugs intended to offset the consequences of atherosclerosis, hypertension, myocardial ischemia, angina, congestive heart failure, and myocardial infarction, selected from the group consisting of:
a. diuretics;
b. vasodilators;
c. β-adrenergic receptor antagonists;
d. angiotensin-II converting enzyme inhibitors (ACE-inhibitors), alone or optionally together with neutral endopeptidase inhibitors;
e. angiotensin II receptor antagonists;
f. renin inhibitors;
g. calcium channel blockers;
h. sympatholytic agents;
i. $\alpha_2$-adrenergic agonists;
j. α-adrenergic receptor antagonists; and
k. HMG-CoA-reductase inhibitors (anti-hypercholesterolemics);
(3) antineoplastic agents selected from:
a. antimitotic drugs selected from:
i. vinca alkaloids selected from:
[1] vinblastine, and
[2] vincristine;
(4) growth hormone secretagogues;
(5) strong analgesics;
(6) local and systemic anesthetics; and
(7) $H_2$-receptor antagonists, proton pump inhibitors, and other gastroprotective agents.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "livestock animals" as used herein refers to domesticated quadrupeds, which includes those being raised for meat and various byproducts, e.g., a bovine animal including cattle and other members of the genus *Bos*, a porcine animal including domestic swine and other members of the genus *Sus*, an ovine animal including sheep and other members of the genus *Ovis*, domestic goats and other members of the genus *Capra;* domesticated quadrupeds being raised for specialized tasks such as use as a beast of burden, e.g., an equine animal including domestic horses and other members of the family Equidae, genus *Equus*, or for searching and sentinel duty, e.g., a canine animal including domestic dogs and other members of the genus *Canis*; and domesticated quadrupeds being raised primarily for recreational purposes, e.g., members of *Equus* and *Canis*, as well as a feline animal including domestic cats and other members of the family Felidae, genus *Felis*.

"Companion animals" as used herein refers to cats, dogs and horses. As used herein, the term "dog(s)" denotes any member of the species *Canis familiaris*, of which there are a large number of different breeds. While laboratory determinations of biological activity may have been carried out using a particular breed, it is contemplated that the inhibitory compounds of the present invention will be found to be useful for treating pain and inflammation in any of these numerous breeds. Dogs represent a particularly preferred class of patients in that they are well known as being very susceptible to chronic inflammatory processes such as osteoarthritis and degenerative joint disease, which in dogs often results from a variety of developmental diseases, e.g., hip dysplasia and osteochondrosis, as well as from traumatic injuries to joints. Conventional NSAIDs, if used in canine therapy, have the potential for serious adverse gastrointestinal reactions and other adverse reactions including kidney and liver toxicity. Gastrointestinal effects such as single or multiple ulcerations, including perforation and hemorrhage of the esophagus, stomach, duodenum or small and large intestine, are usually debilitating, but can often be severe or even fatal.

The term "treating reproductive disorders (preferably in livestock)" as used herein refers to the use of the COX-2 inhibitors of the invention in mammals, preferably livestock animals (cattle, pigs, sheep, goats or horses), during the estrus cycle to control the time of onset of estrus by blocking the uterine signal for lysis of the corpus luteum, i.e. F-series prostaglandins, then removing the inhibition when the onset of estrus is desired. There are settings where it is useful to control or synchronize the time of estrus, especially when artificial insemination or embryo transfer are to be performed. Such use also includes enhancing the rate of embryo survival in pregnant livestock animals. Blocking F-series prostaglandin release can have several beneficial actions including reducing uterine contractions, enhancing uteroplacental bloodflow, supporting recognition of pregnancy, and postponing lysis of the corpus luteum at the time when estrus would have occurred had the animal not become pregnant (around Day 21 of pregnancy). Such treatment also abrogates the effects of stress on reproduction. For example reductions in fertility caused by excessive heat, negative energy balance and other stresses which have a COX-2 mediated component, as does abortion induced by stress such as heat, transportation, co-mingling, palpation, infection, etc. Such treatment is also useful to control the time of parturition, which is accompanied by release of F-series prostaglandins that lead to lysis of the corpus luteum. Inhibition of COX-2 would block the onset of premature labor in livestock animals, allowing the offspring time to mature before birth. Also there are settings where controlling the time of parturition is a useful tool for management of pregnant animals.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine,. such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, ie., $^2$H, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing prodrugs of compounds of the formula I. This invention also encompasses methods of treating disorders that can be treated by the selective inhibition of COX-2 comprising administering prodrugs of compounds of the formula I. Compounds of formula I having free amino, amido, hydroxy, carboxylic acid ester, sulfonamide or carboxylic groups (especially alkyl-S— and alkyl-(S=O)—) can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters are covalently bonded to the above substituents of formula I through the carbonyl carbon prodrug sidechain. Prodrugs also include metabolically labile groups such as ethers, acetates, mercaptans and sulfoxides.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies and TNF receptor immunoglobulin molecules (such as Enbrel®), low dose methotrexate, lefunimide, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc.

The active ingredient of the present invention may be administered in combination with inhibitors of other mediators of inflammation, comprising one or more members selected from the group consisting essentially of the classes of such inhibitors and examples thereof which include, matrix metalloproteinase inhibitors, aggrecanase inhibitors, TACE inhibitors, leucotriene receptor antagonists, IL-1 processing and release inhibitors, ILra, $H_1$-receptor antagonists; kinin-$B_1$- and $B_2$-receptor antagonists; prostaglandin inhibitors such as PGD-, PGF-PGI$_2$-, and PGE-receptor antagonists; thromboxane $A_2$ (TXA2-) inhibitors; 5- and 12-lipoxygenase inhibitors; leukotriene LTC$_4$-, LTD$_4$/LTE$_4$-, and LTB$_4$-inhibitors; PAF-receptor antagonists; gold in the form of an aurothio group together with various hydrophilic groups; immunosuppressive agents, e.g., cyclosporine, azathioprine, and methotrexate; anti-inflammatory glucocorticoids; penicillamine; hydroxychloroquine; anti-gout agents, e.g., coichicine, xanthine oxidase inhibitors, e.g., allopurinol, and uricosuric agents, e.g., probenecid, sulfinpyrazone, and benzbromarone.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, and antimetabolites such as methotrexate.

The compounds of the present invention may also be used in combination with anti-hypertensives and other cardiovascular drugs intended to offset the consequences of atherosclerosis, including hypertension, myocardial ischemia including angina, congestive heart failure, and myocardial infarction, selected from vasodilators such as hydralazine, β-adrenergic receptor antagonists such as propranolol, calcium channel blockers such as nifedipine, α$_2$-adrenergic agonists such as clonidine, α-adrenergic receptor antagonists such as prazosin, and HMG-CoA-reductase inhibitors (anti-hypercholesterolemics) such as lovastatin or atorvastatin.

The active ingredient of the present invention may also be administered in combination with one or more antibiotic, antifungal, antiprotozoal, antiviral or similar therapeutic agents.

The compounds of the present invention may also be used in combination with CNS agents such as antidepressants (such as sertraline), anti-Parkinsonian drugs (such as L-dopa, requip, mirapex, MAOB inhibitors such as selegine and rasagiline, comP inhibitors such as Tasmar, A-2 inhibitors, dopamine reuptake inhibitors, NMDA antagonists, nicotine agonists, dopamine agonists and inhibitors of neuronal nitric oxide synthase), and anti-Alzheimer's drugs such as donepezil, tacrine, COX-2 inhibitors, propentofylline or metryfonate.

The compounds of the present invention may also be used in combination with osteoporosis agents such as roloxifene, lasofoxifene, droloxifene or fosomax and immunosuppressant agents such as FK-506 and rapamycin.

The present invention also relates to the formulation of the active agents of the present invention alone or with one or more other therapeutic agents which are to form the intended combination, including wherein said different drugs have varying half-lives, by creating controlled-release forms of said drugs with different release times which achieves relatively uniform dosing; or, in the case of non-human patients, a medicated feed dosage form in which said drugs used in the combination are present together in admixture in said feed composition. There is further provided in accordance with the present invention co-administration in which the combination of drugs is achieved by the simultaneous administration of said drugs to be given in combination; including co-administration by means of different dosage forms and routes of administration; the use of combinations in accordance with different but regular and continuous dosing schedules whereby desired plasma levels of said drugs involved are maintained in the patient being treated, even though the individual drugs making up said combination are not being administered to said patient simultaneously.

DETAILED DESCRIPTION OF THE INVENTION

The following reaction Schemes illustrate the preparation of the compounds of the present invention. Unless otherwise indicated, $R^1$ through $R^7$, A, X and m in the reaction schemes and discussion that follow are as defined above.

SCHEME 1

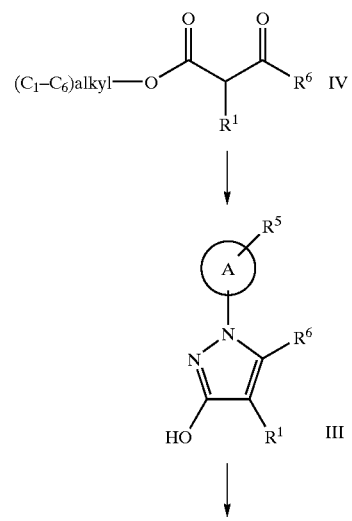

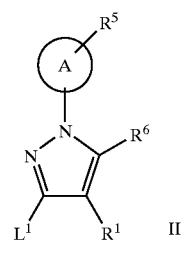
II
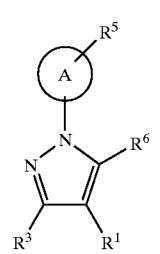
I
SCHEME 2
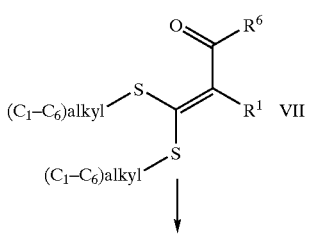
VII
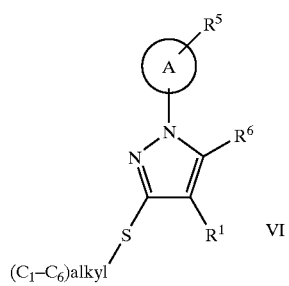
VI
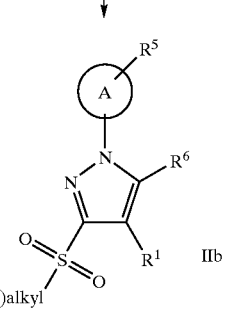
IIb
SCHEME 3
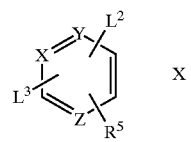
X
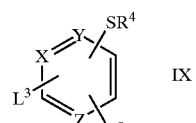
IX
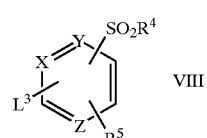
VIII
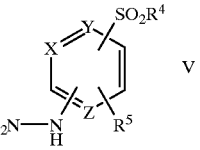
V
SCHEME 4
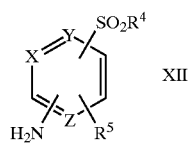
XII
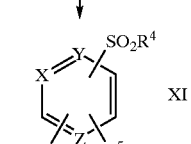
XI
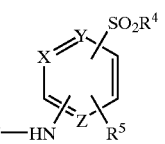
V
Scheme 1 illustrates methods of synthesizing compounds of the formula I. Referring to Scheme 1, a compound of the formula I, wherein the heterocyclic

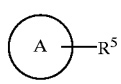

has a general formula

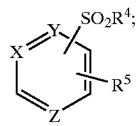

wherein each of X, Y, or Z can independently be $CR^7$ or N and at least one of X, Y, or Z must be N (ie., compounds of general formulae A1 (wherein X is $CR^7$ or N, Y is CH, and Z is N), A2 (wherein X is $CR^7$ or N, Y is CH, and Z is N), A3 (wherein X is CH, Y is N, and Z is N), A4 (wherein X is N, Y is N, and Z is N), A5 (wherein X is N, Y is N, and Z is N), and A6 (wherein X is N, Y is N, and Z is CH)). Specifically, the compounds of formula I (ie., a compound of the formulae IA1–IA6, respectively):

IA1

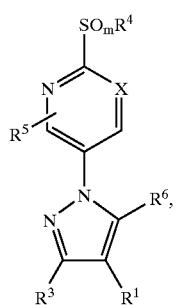

IA2

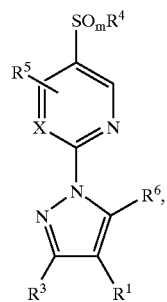

IA3

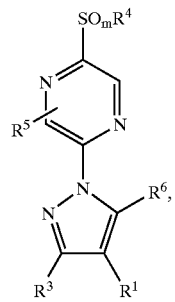

IA4

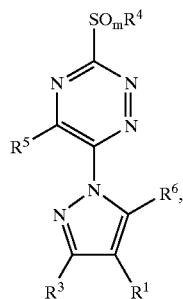

IA5

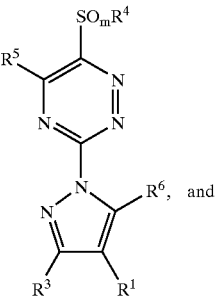

and

IA6

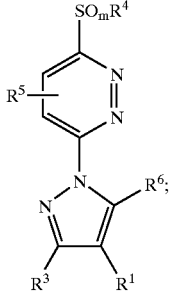

can be prepared by reacting a compound of formula II, wherein $L^1$ is a leaving group, with a a compound of formula $M-R^3$, wherein M is a cation such as sodium, in a solvent. In the aforesaid reaction, said $L^1$ is displaced with said $R^3$. Suitable leaving group $L^1$ includes halo, such as bromo or chloro, or $(C_1-C_6)$alkylsulfonate, such as methylsulfonate. The aforesaid reaction can be performed in neutral or basic conditions by methods familiar to those in the art. Suitable solvents include alcohol (such as methanol or ethanol), $di(C_1-C_6)$alkylethers (such as diethylether), halogenated solvents (such as methylene chloride), or dimethylformamide (DMF). This reaction can be carried out at a temperature of from about −20° C. to about 120° C., preferably from about 25° C. to about 50° C. This reaction can be carried out for a period of from about 1 hour to about 72 hours, preferably for about 24 hours.

The compound of formula II, wherein $L^1$ is a leaving group including halo (compound IIa) or sulfonate (compound IIb) can be prepared by reacting a compound of formula III, with an appropriate reagent, optionally in the presence of a solvent and a base. Suitable halo $L^1$ leaving groups include bromo or chloro. Suitable sulfonate $L^1$ leaving groups include $(C_1-C_6)$alkylsulfonate (such as methylsulfonate), trihalo$(C_1-C_6)$alkylsulfonate (such as trifluoromethylsulfonate), or $(C_6-C_{10})$arylsulfonate (such as para-toluenesulfonate). When $L^1$ is halo, a suitable appropriate reagent is phosphoryloxychloride or phosphoryloxybromide. When $L^1$ is a sulfonate, a suitable appropriate reagent is triflic anhydride, mesyl chloride or tosyl chloride.

Suitable solvents include methylene chloride, DMF or tetrahydrofuran (THF). Suitable bases include triethylamine, sodium hydride, potassiumcarbonate, or sodiumhydroxide. This reaction can be carried out at a temperature of from about 0° C. to about 100° C., preferably about 80° C. in the preparation of the compound of formula IIa; or about 25° C. in the preparation of the compound of formula IIb. This reaction can be carried out for a period of from about 1 hour to about 72 hours, preferably for about 24 hours.

The compound of formula III can be prepared by reacting a compound of formula IV with a compound of formula V:

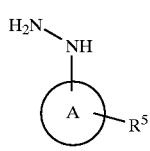
V or an acidic salt thereof, such as a hydrochloric salt thereof, wherein the heterocyclic

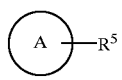

as a general formula

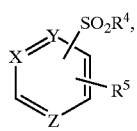

wherein each of X, Y, or Z can be $CR^7$ or N and at least one of X, Y, or Z must be N as defined above. Specifically, the compounds of formula V (i.e., a compound of the formulae VA1–VA6, respectively):

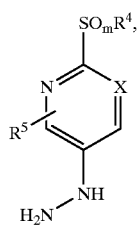
VA1

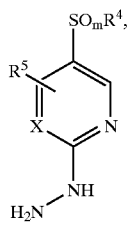
VA2

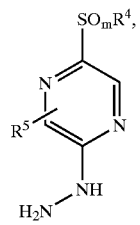
VA3

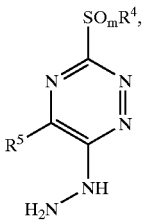
VA4

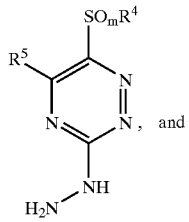
VA5 and

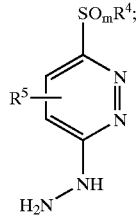
VA6 can be reacted with a compound of formula IV under acidic, neutral or basic conditions, preferably in the presence of an acid or an acid salt of the compound of formula V in a solvent. Suitable acids include hydrochloric acid, acetic acid, trifluoroaceticacid, para-toluenesulfonic acid or sulfuric acid, preferably hydrochloric acid. Suitable acid salts include sodium acetate. Suitable bases include sodium hydroxide or potassium hydroxide. Suitable solvents include alcohol, such as ethanol, trifluoroethanol, methanol, propanol, isopropanol or butanol; dimethyl sulfoxide (DMSO), DMF, N,N-dimethylacetamide (DMA), N-methyl-2-pyrrolidinone (NMP), benzene, toluene, chloroform or mixtures thereof, preferably alcohol, most preferably ethanol or isopropanol. This reaction can be carried out at a temperature from about 0° C. to about 140° C., preferably at about 80° C. to about 100° C., or at reflux temperature of the solvent used. This reaction can be carried out for a period of from about 1 hour to about 72 hours, preferably for about 24 hours.

The compound of formula IV can be purchased or can be prepared according to methods described in the literature, e.g., Advanced Organic Chemistry, $4^{th}$ ed.,1992; *J. Med. Chem.* 1997, 40, 1347–1365; and references cited therein.

Scheme 2 illustrates alternative methods of synthesizing compounds of the formula IIb, as defined above. Referring to Scheme 2, a compound of the formula IIb can be prepared by reacting a compound of formula VI with an oxidizing agent in a solvent optionally in the presence of a base. Suitable oxidizing agents include meta-chloroperbenzoic acid, hydrogen peroxide, OXONE®, nitric acid or barium permangate. Suitable solvents include alcohol-water (such as methanol-water or ethanol-water), dioxane-water, tetrahydrofuran-water, methylene chloride, chloroform, di($C_1$–$C_6$)alkylethers (such as diethylether), halogenated solvents (such as methylene chloride), or DMF, preferably methanol-water. Suitable bases include sodium hydroxide. This reaction can be carried out at a temperature of from about 0° C. to about 25° C., preferably from about 20° C. to about 25° C. This reaction can be carried out for a period of from about 0.5 hours to about 24 hours, preferably for about 3 hours.

The compound of formula VI can be prepared by reacting a compound of formula VII with a compound of formula V (i.e., a compound of the formulae VA1–VA6, respectively, as defined above), or an acidic salt thereof, such as a hydrochloric salt thereof, under acidic, neutral or basic conditions, preferably in the presence of an acid or an acid salt of the compound of the formula V in a solvent. Suitable acids include hydrochloric acid, acetic acid, trifluoroaceticacid, para-toluenesulfonic acid or sulfuric acid, preferably hydrochloric acid. Suitable acid salts include sodium acetate. Suitable bases include sodium hydroxide or potassium hydroxide. Suitable solvents include alcohol (such as ethanol, trifluoroethanol, methanol, propanol, isopropanol or butanol), alcohol-water, DMSO, DMF, DMA, NMP, benzene, toluene, chloroform or mixtures thereof, preferably alcohol, most preferably ethanol or isopropanol. This reaction can be carried out at a temperature from about 60° C. to about 100° C. This reaction can be carried out for a period of from about 1 hour to about 24 hours.

The compound of formula VII can be purchased or can be prepared according to methods described in the literature, e.g., Advanced Organic Chemistry, 4$^{th}$ ed., 1992.

Scheme 3 refers to the preparation of compounds of the formula V (i.e., a compound of the formulae VA1–VA6, respectively, as defined above) in a multi-step process from a compound of formula X, wherein each of $L^2$ and $L^3$, individually, are leaving groups. Referring to Scheme 3, a compound of the formula V can be prepared by reacting a compound of the formula VIII (i.e., a compound of the formulae VIIIA1–VIIIA6, respectively):

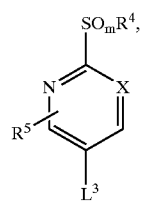

VIIIA1

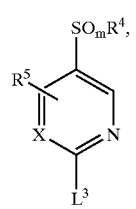

VIIIA2

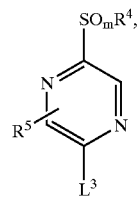

VIIIA3

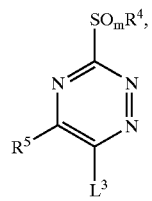

VIIIA4

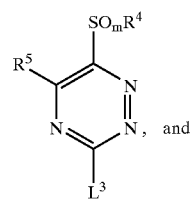

VIIIA5 and

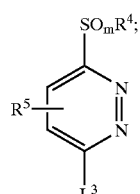

VIIIA6 wherein $L^3$ is a leaving group, with hydrazine (preferably anhydrous hydrazine) in the presence of a solvent. Suitable $L^3$ leaving groups include halo, preferably chloro or bromo. Suitable solvents include alcohol (such as ethanol, methanol, propanol or butanol), DMSO, DMF, DMA, or NMP, preferably alcohol, most preferably ethanol. This reaction can be carried out at a temperature from about 0° C. to about 140° C., preferably from about 80° C. to about 100° C., or at about the reflux temperature of the solvent used in this reaction. This reaction can be carried out for a period of from about 1 hour to about 72 hours, preferably from about 1 hour to about 24 hours. Preferably the product is isolated as a salt, such as a hydrobromide or hydrochloride salt, preferably hydrochloride salt.

The compound of formula VIII (i.e., a compound of the formulae VIIIA1–VIIIA6, respectively, as defined above) can be prepared by reacting a compound of the formula IX (i.e., a compound of the formulae IXA1–IXA6, respectively):

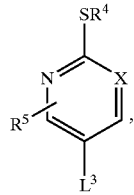

IXA1

-continued

IXA2
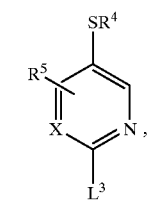

IXA3
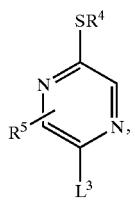

IXA4
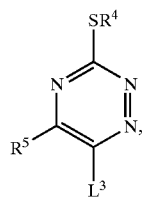

IXA5
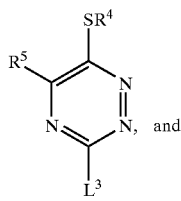, and

IXA6
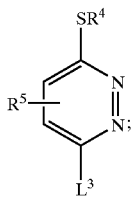

wherein $L^3$ is a leaving group, with an oxidizing reagent in the presence of a solvent. Suitable leaving groups include halo, sulfonate, or sulfone, preferably halo such as chloro or bromo. Suitable oxidizing agents include meta-chloroperbenzoic acid, hydrogen peroxide, sodium perborate, or OXONE® Suitable solvents or solvent mixtures include methanol-water, dioxane-water, tetrahydrofuran-water, methylene chloride, or chloroform, preferably methanol-water. This reaction can be carried out at a temperature from about 0° C. to about 60° C., preferably the temperature may range from about 20° C. to about 25° C. (i.e. room temperature). This reaction can be carried out for a period of from about 0.5 hours to about 24 hours, preferably about 16 hours.

The compounds of the, formula IX (i.e., a compound of the formulae IXA1–IXA6, respectively, as defined above) can be prepared by reacting a compound of formula X (i.e., a compound of the formulae XA1–XA6, respectively):

XA1
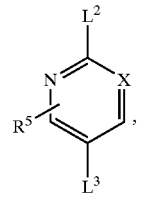

XA2
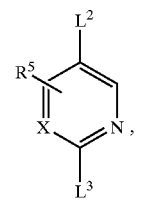

XA3
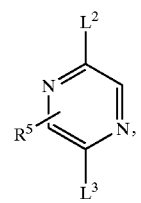

XA4
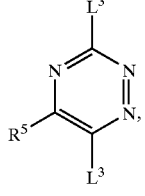

XA5
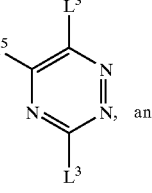, and

XA6
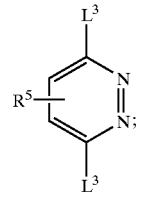

wherein each of $L^2$ and $L^3$ independently is a leaving group, with a sulfur nucleophilic reagent optionally in the presence of a base in a solvent. Suitable leaving groups $L^2$ include halo (such as chloro or bromo), sulfonate, or sulfone, preferably chloro or bromo. Suitable leaving groups $L^3$ include halo (such as chloro or bromo), sulfonate, or sulfone, preferably chloro or bromo. Suitable sulfur nucleophilic reagents include alkylthiol, dialkyldisulfide, alkylsulfonate, sodium thioalkoxide or potassium thioalkoxide. Suitable bases include sodium hydroxide, triethylamine, alkyllithium (such as n-butyllithium, sec-butyllithium, or tert-butyllithium), or lithium diisopropylamide. Suitable solvents include di($C_1$–$C_6$)alkylether (such as dimethylether), alcohol (such as methanol, ethanol or tert-butanol), THF, benzene, toluene, xylene, DMF, DMSO, dioxane, 1,2-dimethoxyethane, and a mixture of alcohol and water. This reaction can be carried out at a temperature from about −78°

C. to about 200° C., preferably from about 0° C. to about 100° C. This reaction can be carried out for a period of from about 1 minute to 1 day, preferably about 30 minutes.

Scheme 4 refers to an alternative preparation of compounds of the formula V (i.e., a compound of the formulae VA1–VA6, respectively, as defined above) by multi step reactions, i.e., a nitrosation reaction followed by reduction. Referring to Scheme 4, a compound of the formula V can be prepared by reacting a compound of formula XI (i.e., a compound of the formulae XIA1–XIA6, respectively):

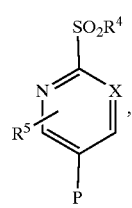

XIA1

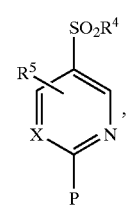

XIA2

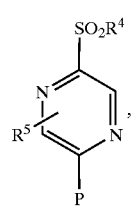

XIA3

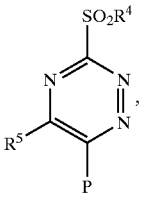

XIA4

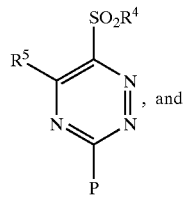

XIA5, and

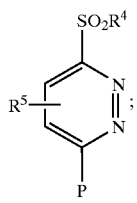

XIA6 wherein P is —NH—NO or —N≡N$^+$, with a reducing agent or a catalytic hydrogenating agent in an inert solvent. Suitable reducing agents include metal halides such as TiCl$_3$, SnCl$_2$, zinc powder-acetic acid, sodium-ethanol, sodium-aqueous ammonia, lithium aluminum hydride and the like. Suitable catalytic hydrogenating agents include hydrogen gas at a pressure from about 1 atmosphere to about 5 atmospheres and a temperature of from about 10° C. to about 60° C., in the presence of a catalyst such as palladium on carbon (Pd/C), palladium on barium sulfate (Pd/BaSO$_4$), platinum on carbon (Pt/C), or tris(triphenylphosphine) rhodium chloride (Wilkinson's catalyst). Preferably the catalytic hydrogenating agent is Pd/C at 25° C. and 50 psi of hydrogen gas pressure in methanol solvent. Suitable solvents include alcohol (such as methanol or ethanol), THF, dioxane, or ethyl acetate. This method also provides for introduction of hydrogen isotopes (i.e., deuterium or tritium) by replacing $^1$H$_2$ with $^2$H$_2$ or $^3$H$_2$ in the above procedure.

A compound of the formula XI (i.e., a compound of the formulae XIA1–XIA6, respectively, as defined above) can be prepared by reaction of a compound of the formula XII (i.e., a compound of the formulae XIIA1–XIIA6, respectively):

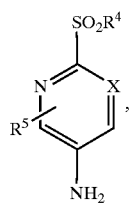

XIIA1

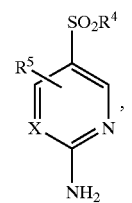

XIIA2

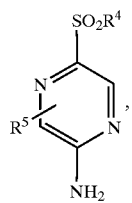

XIIA3

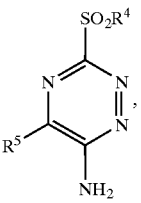

XIIA4

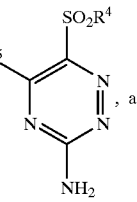

XIIA5, and

-continued

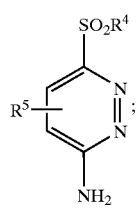

XIIA6 with a suitable reagent. Suitable reagents include sodium nitrite in an aqueous medium (such as hydrochloric acid in water), nitrosyl chloride, nitrogen oxides and nitrile ethers. This reaction can be carried out at a temperature from about −78° C. to about 200° C., preferably from about −10° C. to about 0° C. This reaction can be carried out for a period of about 1 minute to about 10 hours.

Compounds of formula XII (i.e., a compound of the formulae XIIA1–XIIA6, respectively, as defined above) are commercially available or can be prepared by methods well known to those of ordinary skill in the art (see F. Walker et al., *J. Chem. Soc.* 1939, 1948).

Compounds of the formula V (i.e., a compound of the formulae VA1–VA6, respectively, as defined above) may be prepared by methods well known to those of ordinary skill in the art (see *Collection Czechoslov. Chem. Commun.* Vol. 37, p. 1721, 1972 by J. Vafrina et. al.; European Patent Publications EP 1104759 and EP 1104760).

Other methods of preparing the compounds of Formula I are well known to those skilled in the art such as those described in *Heterocycles*, 31,1041 (1990). The compounds of formula I can also be synthesized by using the method of Kharash, Negishi, Stille, or Suzuki et. al., which are well known in the art. In general, heteroaryl compounds are synthesized by a number of catalytic cross-coupling reactions from heteroaryl halides or triflates and heteroaryl metal reagents (such as Grignard reagent (the so-called Kharasch reaction), heteroaryl zinc reagent (the so-called Negishi reaction), heteroaryl tin reagent (the so-called Stille reaction), heteroaryl silyl reagent, etc. (see for example S. P. Stanforth, *Tetrahedron*, 1998, 54, 263–303)).

Unless indicated otherwise, the pressure of each of the above reactions is not critical. Generally, the reactions will be conducted at a pressure of about one to about three atmospheres, preferably at ambient pressure (about one atmosphere).

Those skilled in the art will appreciate that the above schemes describe general methods for preparing the compounds of the invention. Specific compounds of formula I may possess sensitive functional groups that require protecting groups when prepared with the intermediates described. Examples of suitable protecting groups may be found in T. W. Greene and P. Wuts, Protecting Groups in Organic Synthesis, John Wiley & Sons, 2nd Edition, New York, 1991.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, e.g., wherein A or any of $R^1$, $R^3$, $R^4$, $R^5$ or $R^6$ include a hydroxycarbonyl, tetrazole, or other acidic moiety, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Method for Assessing Biological Activities

The activity of the compounds of the formula I of the present invention was demonstrated by the following assays.

Human In Vitro Assays

Human Cell-Based COX-1 Assay

Human peripheral blood obtained from healthy volunteers was diluted to 1/10 volume with 3.8% sodium citrate solution. The platelet-rich plasma immediately obtained was washed with 0.14 M sodium chloride containing 12 mM Tris-HCl (pH 7.4) and 1.2 mM EDTA. Platelets were then washed with platelet buffer (Hanks buffer (Ca free) containing 0.2% BSA and 20 mM Hepes). Finally, the human washed platelets (HWP) were suspended in platelet buffer at the concentration of $2.85 \times 10^8$ cells/ml and stored at room temperature until use. The HWP suspension (70 μl aliquots, final $2.0 \times 10^7$ cells/ml) was placed in a 96-well U bottom plate and 10 μl aliquots of 12.6 mM calcium chloride added. Platelets were incubated with A23187 (final 10 μM, Sigma) with test compound (0.1–100 μM) dissolved in DMSO (final concentration; less than 0.01%) at 37° C. for 15 minutes. The reaction was stopped by addition of EDTA (final 7.7 mM) and TxB2 in the supernatant quantitated by using a radioimmunoassay kit (Amersham) according to the manufacturer's procedure.

Human Cell-Based COX-2 Assay

The human cell based COX-2 assay was carried out as previously described (Moore et al., *Inflam. Res.*, 45, 54, 1996). Confluent human umbilical vein endothelial cells (HUVECs, Morinaga) in a 96-well flat bottom plate were washed with 80 ml of RPMI1640 containing 2% FBS and incubated with hIL-1β (final concentration 300 U/ml, R & D Systems) at 37° C. for 24 hours. After washing, the activated HUVECs were incubateed with test compound (final concentration; 0.1 nM–1 µM) dissolved in DMSO (final concentration; less than 0.01%) at 37° C. for 20 minutes and stimulated with A23187 (final concentration 30 mM) in Hanks buffer containing 0.2% BSA, 20 mM Hepes at 37° C. for 15 minutes. 6-Keto-$PGF_{1\alpha}$, stable metabolite of PGI2, in the supernatant was quantitated by using a radioimmunoassay method (antibody; Preseptive Diagnostics, SPA; Amersham).

Canine In Vitro Assays

The following canine cell based COX 1 and COX-2 assays have been reported in Ricketts et al., *Evaluation of Selective Inhibition of Canine Cyclooxyenase 1 and 2 by Carprofen and Other Nonsteroidal Anti-inflammatory Drugs*, American Journal of Veterinary Research, 59 (11), 1441–1446.

Protocol for Evaluation of Canine COX-1 Activity

Test drug compounds were solubilized and diluted the day before the assay was to be conducted with 0.1 mL of DMSO/9.9 mL of Hank's balanced salts solution (HBSS), and stored overnight at 4° C. On the day that the assay was carried out, citrated blood was drawn from a donor dog, centrifuged at 190×g for 25 minutes at room temperature, and the resulting platelet-rich plasma was then transferred to a new tube for further procedures. The platelets were washed by centrifuging at 1500×g for 10 minutes at room temperature. The platelets were washed with platelet buffer comprising Hank's buffer (Ca free) with 0.2% bovine serum albumin (BSA) and 20 mM HEPES. The platelet samples were then adjusted to $1.5\times10^7$/mL, after which 50 µl of calcium ionophore (A23187) together with a calcium chloride solution were added to 50 µl of test drug compound dilution in plates to produce final concentrations of 1.7 µM A23187 and 1.26 mM Ca. Then, 100 µl of canine washed platelets were added and the samples were incubated at 37° C. for 15 minutes, after which the reaction was stopped by adding 20 µl of 77 mM EDTA. The plates were then centrifuged at 2000×g for 10 minutes at 4° C., after which 50 µl of supernatant was assayed for thromboxane $B_2$ ($TXB_2$) by enzyme-immunoassay (EIA). The pg/mL of $TXB_2$ was calculated from the standard line included on each plate, from which it was possible to calculate the percent inhibition of COX-1 and the $IC_{50}$ values for the test drug compounds.

Protocol for Evaluation of Canine COX-2 Activity

A canine histocytoma (macrophage-like) cell line from the American Type Culture Collection designated as DH82, was used in setting up the protocol for evaluating the COX-2 inhibition activity of various test drug compounds. There was added to flasks of these cells 10 µg/mL of LPS, after which the flask cultures were incubated overnight. The same test drug compound dilutions as described above for the COX-1 protocol were used for the COX-2 assay and were prepared the day before the assay was carried out. The cells were harvested from the culture flasks by scraping, and were then washed with minimal Eagle's media (MEM) combined with 1% fetal bovine serum, centrifuged at 1500 rpm for 2 minutes, and adjusted to a concentration of $3.2\times10^5$ cells/mL. To 50 µl of test drug dilution there was added 50 µl of arachidonic acid in MEM to give a 10 µM final concentration, and there was added as well 100 µl of cell suspension to give a final concentration of $1.6\times10^5$ cells/mL. The test sample suspensions were incubated for 1 hour and then centrifuged at 1000 rpm for 10 minutes at 4° C., after which 50 µl aliquots of each test drug sample were delivered to EIA plates. The EIA was performed for prostaglandin $E_2$ ($PGE_2$), and the pg/mL concentration of $PGE_2$ was calculated from the standard line included on each plate. From this data it was possible to calculate the percent inhibition of COX-2 and the $IC_{50}$ values for the test drug compounds. Repeated investigations of COX-1 and COX-2 inhibition were conducted over the course of several months. The results are averaged, and a single COX-1: COX-2 ratio is calculated.

Whole blood assays for COX-1 and COX-2 are known in the art such as the methods described in C. Brideau, et al., *A Human Whole Blood Assay for Clinical Evaluation of Biochemical Efficacy of Cyclooxygenase Inhibitors, Inflammation Research*, Vol. 45, pp. 68–74 (1996). These methods may be applied with feline, canine or human blood as needed.

In Vivo Assays

Carrageenan Induced Foot Edema in Rats

Male Sprague-Dawley rats (5 weeks old, Charles River Japan) were fasted overnight. A line was drawn using a marker above the ankle on the right hind paw and the paw volume (V0) was measured by water displacement using a plethysmometer (Muromachi). Animals were given orally either vehicle (0.1% methyl cellulose or 5% Tween 80) or a test compound (2.5 ml per 100 g body weight). One hour later, the animals were then injected intradermally with λ-carrageenan (0.1 ml of 1% w/v suspension in saline, Zushikagaku) into right hind paw (Winter et al., *Proc. Soc. Exp. Biol. Med.*, 111, 544, 1962; Lombardino et al.,*Arzneim. Forsch.*, 25, 1629, 1975) and three hours later, the paw volume (V3) was measured and the increase in volume (V3–V0) calculated. Since maximum inhibition attainable with classical NSAIDs is 60–70%, $ED_{30}$ values were calculated.

Gastric Ulceration in Rats

The gastric ulcerogenicity of test compound was assessed by a modification of the conventional method (Ezer et al.,*J. Pharm. Pharmacol.*, 28, 655, 1976; Cashin et al., *J. Pharm. Pharmacol.*, 29, 330–336, 1977). Male Sprague-Dawley rats (5 weeks old, Charles River Japan), fasted overnight, were given orally either vehicle (0.1% methyl cellulose or 5% Tween 80) or a test compound (1 ml per 100 g body weight). Six hours after, the animals were sacrificed by cervical dislocation. The stomachs were removed and inflated with 1% formalin solution (10 ml). Stomachs were opened by cutting along the greater curvature. From the number of rats that showed at least one gastric ulcer or haemorrhaging erosion (including ecchymosis), the incidence of ulceration was calculated. Animals did not have access to either food or water during the experiment.

Canine Whole Blood ex vivo Determinations of COX-1 and COX-2 Activity Inhibition The in vivo inhibitory potency of a test compound against COX-1 and COX-2 activity may be evaluated using an ex vivo procedure on canine whole blood. Three dogs were dosed with 5 mg/kg of the test compound administered by oral gavage in 0.5% methylcellulose vehicle and three dogs were untreated. A zero-hour blood sample was collected from all dogs in the study prior to dosing, followed by 2- and 8-hour post-dose blood sample collections. Test tubes were prepared containing 2 µL of either (A) calcium ionophore A23187 giving a 50 µM final concentration, which stimulates the production of thromboxane $B_2$ ($TXB_2$) for COX-1 activity determination; or of (B) lipopolysaccharide (LPS) to give a 10 µ/mL final concentration, which stimulates the production of prostaglandin $E_2$ ($PGE_2$) for COX-2 activity determination. Test tubes with unstimulated vehicle were used as controls. A 500 $\mu L$ sample of blood was added to each of the above-described test tubes, after which they were incubated at 37° C. for one hour in the case of the calcium ionophore-containing test tubes, and overnight in the case of the LPS-containing test tubes. After incubation, 10 $\mu L$ of EDTA was added to give a final concentration of 0.3%, in order to prevent coagulation of the plasma which sometimes occurs after thawing frozen plasma samples. The incubated samples were centrifuged at 4° C. and the resulting plasma sample of ~200 $\mu L$ was collected and stored at −20° C. in polypropylene 96-well plates. In order to determine endpoints for this study, enzyme immunoassay (EIA) kits available from Cayman were used to measure production of $TXB_2$ and $PGE_2$, utilizing the principle of competitive binding of tracer to antibody and endpoint determination by colorimetry. Plasma samples were diluted to approximate the range of standard amounts which would be supplied in a diagnostic or research tools kit, i.e., 1/500 for $TXB_2$ and 1/750 for $PGE_2$.

The data set out in Table 1 below show how the percent inhibition of COX-1 and COX-2 activity is calculated based on their zero hour values. The data is expressed as treatment group averages in pg/ml of $TXB_2$ and $PGE_2$ produced per sample. Plasma dilution was not factored in said data values.

The data in Table 1 show that, in this illustration, at the 5 mg/kg dose there was significant COX-2 inhibition at both timepoints. The data in Table 1 also show that at the 5 mg/kg dose there was no significant inhibition of COX-1 activity at the timepoints involved. Accordingly, the data in Table 1 clearly demonstrates that at the 5 mg/kg dosage concentration this compound possesses good COX-2 selectivity.

TABLE 1

| COX-1 ACTIVITY INHIBITION - Group Averages | | | | | |
| --- | --- | --- | --- | --- | --- |
| | $TXB_2$ Pg/mL/Well | | | Percent Inhibition | |
| Hour | 0-hour | 2-hour | 8-hour | 2-hour | 8-hour |
| Untreated | 46 | 45 | 140 | 2% | 0% |
| 5 mg/kg | 41 | 38 | 104 | 7% | 0% |

| COX-2 ACTIVITY INHIBITION - Group Averages | | | | | |
| --- | --- | --- | --- | --- | --- |
| | $PGE_2$ Pg/mL/Well | | | Percent Inhibition | |
| Hour | 0-hour | 2-hour | 8-hour | 2-hour | 8-hour |
| Untreated | 420 | 486 | 501 | 0% | 0% |
| 5 mg/kg | 711 | 165 | 350 | 77% | 51% |

COX inhibition is observed when the measured percent inhibition is greater than that measured for untreated controls. The percent inhibition in the above table is calculated in a straightforward manner in accordance with the following equation:

$$\% \text{ Inhibition}(2\text{-hour}) = \frac{(PGE_2 \text{ at } t = 0) - (PGE_2 \text{ at } t = 2)}{(PGE_2 \text{ at } t = 0)}$$

Data Analysis

Statistical program packages, SYSTAT (SYSTAT, INC.) and StatView (Abacus Cencepts, Inc.) for Macintosh were used. Differences between test compound treated group and control group were tested for using ANOVA. The $IC_{50}$ ($ED_{30}$) values were calculated from the equation for the log-linear regression line of concentration (dose) versus percent inhibition.

Most compounds prepared in the Working Examples as described hereinafter were tested by at least one of the methods described above, and showed $IC_{50}$ values of 0.001 $\mu M$ to 3 $\mu M$ with respect to inhibition of COX-2 in either the canine or human assays.

COX-2 selectivity can be determined by ratio in terms of $IC_{50}$ value of COX-1 inhibition to COX-2 inhibition. In general, it can be said that a compound showing a COX-2/COX-1 inhibition ratio of more than 5 has good COX-2 selectivity.

The compounds of the formula I of this invention can be administered via oral, parenteral, anal, buccal or topical routes to mammals (including humans, dogs, cats, horses and livestock).

In general, these compounds are most desirably administered to humans in doses ranging from 0.01 mg to 100 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for the treatment of abovementioned diseases.

These compounds are most desirably administered to said non-human mammals, e.g. dogs, cats, horses or livestock in an amount, expressed as mg per kg of body weight of said member per day, ranging from about 0.01 mg/kg to about 20.0 mg/kg/day, preferably from about 0.1 mg/kg to about 12.0 mg/kg/day, more preferably from about 0.5 mg/kg to about 10.0 mg/kg/day, and most preferably from about 0.5 mg/kg to about 8.0 mg/kg/day.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging from 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various combinations thereof.

A preferred composition for dogs comprises an ingestible liquid peroral dosage form selected from the group consisting of a solution, suspension, emulsion, inverse emulsion, elixir, extract, tincture, and concentrate, optionally to be added to the drinking water of the dog being treated. Any of these liquid dosage forms, when formulated in accordance with methods well known in the art, can either be administered directly to the dog being treated, or may be added to the drinking water of the dog being treated. The concentrate liquid form, on the other hand, is formulated to be added first to a given amount of water, from which an aliquot amount may be withdrawn for administration directly to the dog or addition to the drinking water of the dog.

A preferred composition provides delayed-, sustained-, and/or controlled-release of said anti-inflammatory selective COX-2 inhibitor. Such preferred compositions include all such dosage forms which produce $\geq 80\%$ inhibition of COX-2 isozyme activity and result in a plasma concentration of said inhibitor of at least 3 fold the COX-2 $IC_{50}$ for at least 4 hours; preferably for at least 8 hours; more preferably for at least 12 hours; more preferably still for at least 16 hours; even more preferably still for at least 20 hours; and most preferably for at least 24 hours. Preferably, there is included within the above-described dosage forms those which produce $\geq 80\%$ inhibition of COX-2 isozyme activity and result in a plasma concentration of said inhibitor of at least 5 fold the COX-2 $IC_{50}$ for at least 4 hours, preferably for at least 8 hours, more preferably for at least 12 hours, still more preferably for at least 20 hours, and most preferably for at least 24 hours. More preferably, there is included the above-described dosage forms which produce $\geq 90\%$ inhibition of COX-2 isozyme activity and result in a plasma concentration of said inhibitor of at least 5 fold the COX-2 $IC_{50}$ for at least 4 hours, preferably for at least 8 hours, more preferably for at least 12 hours, still more preferably for at least 20 hours, and most preferably for at least 24 hours.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The compounds of formula I may also be administered in the form of suppositories for rectal or vaginal administration of the active ingredient. These compositions can be prepared by mixing the active ingredient with a suitable non-irritating excipient which is solid at room temperature (for example, 10° C. to 32° C.) but liquid at the rectal temperature and will melt in the rectum or vagina to release the active ingredient. Such materials are polyethylene glycols, cocoa butter, suppository and wax.

For buccal administration, the composition may take the form of tablets or lozenges formulated in conventional manner.

For transdermal administration, transdermal patches prepared in accordance with well known drug delivery technology may be prepared and applied to the skin of a mammal, preferably a human or a dog, to be treated, whereafter the active agent by reason of its formulated solubility characteristics migrates across the epidermis and into the dermal layers of the skin where it is taken up as part of the general circulation, ultimately providing systemic distribution of the active ingredient over a desired, extended period of time. Also included are implants which are placed beneath the epidermal layer of the skin, i.e. between the epidermis and the dermis of the skin of the patient being treated. Such an implant will be formulated in accordance with well known principles and materials commonly used in this delivery technology, and may be prepared in such a way as to provide controlled-, sustained-, and/or delayed-release of the active ingredient into the systemic circulation of the patient. Such subepidermal (subcuticular) implants provide the same facility of installation and delivery efficiency as transdermal patches, but without the limitation of being subject to degradation, damage or accidental removal as a consequence of being exposed on the top layer of the patient's skin.

EXAMPLES

The following examples contain detailed descriptions of the methods of the preparation of compounds of formula I. These detailed descriptions fall within the scope of the invention and serve to exemplify the above described general synthetic procedures which form part of the invention. These detailed descriptions are presented for illustrative purposes only and are not intended to restrict the scope of the present invention.

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath of up to 60° C.; reactions were monitored by thin layer chromatography (TLC) and analytical column liquid chromatography, and reaction times are given for illustration only; melting points (m.p.) given are uncorrected (polymorphism may result in different melting points); structure and purity of all isolated compounds were assured by at least one of the following techniques: TLC (Merck silica gel 60 F-254 precoated plates), high performance liquid chromatograpy (HPLC), or mass spectrometry. Flash column chromatography was carried out using Merck silica gel 60 (230–400 mesh ASTM). Preparative HPLC was carried out using Hewlett Packard 1100 Liquid Chromatography/Mass Selective Detector (LC/MSD). Separation was done on a Monochrom 5$\mu$ CN column PN 0509–250*212 from MetaChem Technologies. The flow rate was 20 ml/min running a gradient of 0 to 90% of isopropanol in n-hexane. Low-resolution mass spectral data (EI) were obtained on an Automass 120 (JEOL) mass spectrometer. Liquid Chromatography data was collected on a Hewlett Packard 1100 Liquid Chromatography/Mass Selective Detector (LC/MSD). Analysis was performed on a Luna C-18 column with dimensions of 3.0×150 mm. The flow rate was 0.425 ml/minute running a gradient of 50% 0.1% aqueous formic acid and 50% acetonitrile to 100% acetonitrile in 15 minutes. The ionization type for the mass detector of the Mass Spectrophotometer was atmospheric pressure electrospray in the positive ion mode with a fragmentor voltage of 50 volts.

SYNTHETIC SCHEME

Preparation of 3-thiomethyl pyrazoles.

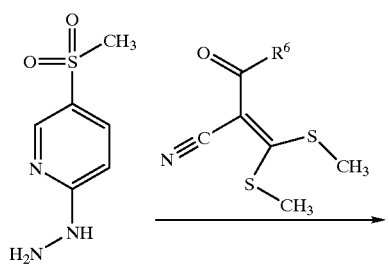

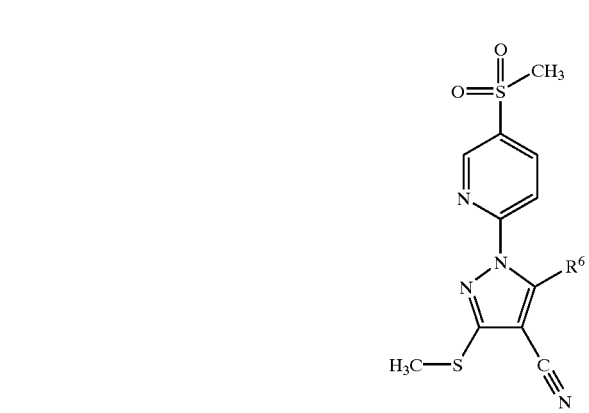

Procedure:

Example 1

1-(5-Methanesulfonyl-pyridin-2-yl)-3-methylsulfanyl-5-phenyl-1H-pyrazole-4-carbonitrile A mixture of the 2-hydrazino-5-methylsulfonyl pyridine (180 mg, 0.81 mmol) and 1-benzoyl-2,2-bis(methylthio)-1-cyano ethene (201 mg, 0.81 mmol) in anhydrous ethanol was refluxed overnight. The resulting solution was cooled to room temperature, diluted with water (25 ml) and extracted with ethyl acetate (2×25 ml). The ethyl acetate layer was dried with sodium sulfate and concentrated to give crude product. Chromatography of the mixture led to the isolation of the desired product (26 mg, 9%) in the form of a white solid.

The following examples were prepared by a procedure analogous to that of Example 1, except where indicated. LC refers to liquid chromatography elution time (minutes) and MS refers to mass spectral peaks (AMU). The particular apparatus and data acquisition parameters are as defined above.

Example 2

5-(4-Chloro-phenyl)-1-(5-methanesulfonyl-pyridin-2-yl)-3-methylsulfanyl-1H-pyrazole-4-carbonitrile The title compound was prepared as in Example 1 wherein 1-(4-chloro benzoyl)-2,2-bis(methylthio)-1-cyano ethene was used in place of wherein 1-benzoyl-2,2-bis(methylthio)-1-cyano ethene. Chromatography of the mixture led to the isolation of the desired product (45 mg, 24%) in the form of a white solid.

Example 3

1-(5-Methanesulfonyl-pyridin-2-yl)-3-methylsulfanyl-5-p-tolyl-1H-pyrazole-4-carbonitrile The title compound was prepared as in Example 1 wherein 1–4-methyl benzoyl)-2,2-bis(methylthio)-1-cyano ethene was used in place of 1-benzoyl-2,2-bis(methylthio)-1-cyano ethene. Chromatography of the mixture led to the isolation of the desired product (24 mg, 14%) in the form of a pale white solid.

Example 4

1-(5-Methanesulfonyl-pyridin-2-yl)-3-methylsulfanyl-5-thiophen-2-yl-1H-pyrazole-4-carbonitrile The title compound was prepared as in Example 1 wherein 1-(thiophene-2-carbonyl)-2,2-bis(methylthio)-1-cyano ethene was used in place of 1-benzoyl-2,2-bis(methylthio)-1-cyano ethene. Chromatography of the mixture led to the isolation of the desired product (53 mg, 30%) in the form of a white solid.

Example 5

1-(5-Methanesulfonyl-pyridin-2-yl)-3-methylsulfanyl-5-m-tolyl-1H-pyrazole-4-carbonitrile The title compound was prepared as in Example 1 wherein 1-(3-methylbenzoyl)-2,2-bis(methylthio)-1-cyano ethene was used in place of 1-benzoyl-2,2-bis(methylthio)-1-cyano ethene. Chromatography of the mixture led to the isolation of the desired product (8 mg, 4.4%) in the form of a pale white solid.

Example 6

5-(3-Chloro-phenyl)-1-(5-methanesulfonyl-pyridin-2-yl)-3-methylsulfanyl-1H-pyrazole-4-carbonitrile The title compound was prepared as in Example 1 wherein 1-(3-chlorobenzoyl)-2,2-bis(methylthio)-1-cyano ethene was used in place of 1-benzoyl-2,2-bis(methylthio)-1-cyano ethene. Chromatography of the mixture led to the isolation of the desired product (8 mg, 4.3%) in the form of a white solid.

Example 7

1-(5-methanesulfonyl-pyridin-2-yl)-3-methylsulfonyl-5-phenyl-1H-pyrazole-4-carbonitrile The title compound was prepared by reacting the compound of Example 1 with meta-chloroperbenzoic acid.

Example 8

5-furan-2-yl-1-(5-methanesulfonyl-pyridin-2-yl)-3-methylsulfanyl-1H-pyrazole-4-carbonitrile The title compound was prepared as in Example 1 wherein 1-(furan-2-oyl)-2,2-bis(methylthio)-1-cyano ethene was used in place of 1-benzoyl-2,2-bis(methylthio)-1-cyano ethene. Chromatography of the mixture led to the isolation of the desired product in the form of a white solid.

The chemical structures and molecular weights of the above Examples 1–8 are tabulated below in Table 2.

TABLE 2

| Example | Structure | MW | LC | MS |
|---|---|---|---|---|
| 1 | (5-methylsulfonyl-pyridin-2-yl)-5-phenyl-3-methylthio-pyrazole-4-carbonitrile | 370 | 10.882 | 371 |
| 2 | (5-methylsulfonyl-pyridin-2-yl)-5-(4-chlorophenyl)-3-methylthio-pyrazole-4-carbonitrile | 405 | 13.34 | 405 (M+)<br>406 (M + H) |
| 3 | (5-methylsulfonyl-pyridin-2-yl)-5-(4-methylphenyl)-3-methylthio-pyrazole-4-carbonitrile | 384 | 12.532 | 385 |
| 4 | (5-methylsulfonyl-pyridin-2-yl)-5-(thiophen-2-yl)-3-methylthio-pyrazole-4-carbonitrile | 376 | 10.71 | 377 |

TABLE 2-continued
| Example | Structure | MW | LC | MS |
|---|---|---|---|---|
| 5 | 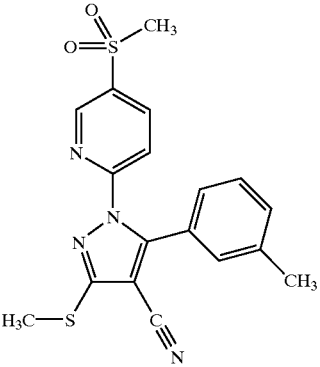 | 384 | 12.51 | 385 |
| 6 | 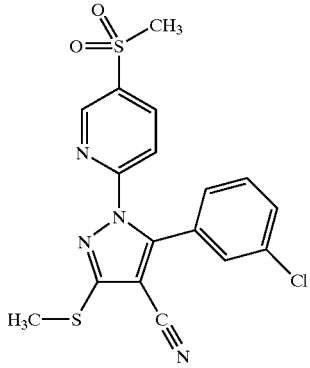 | 405 | N/A | 406 |
| 7 | 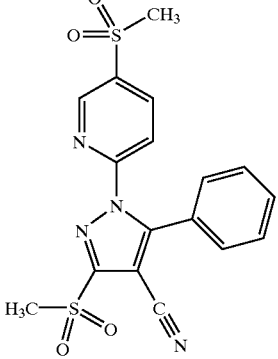 | 402 | N/A | 403 |
| 8 | 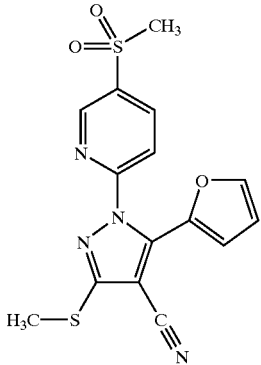 | 360 | N/A | 361 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

We claim:

1. A compound of the formula

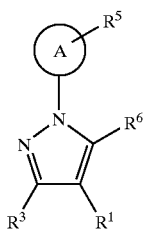

I wherein

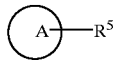

is a heterocycle selected from the group consisting of

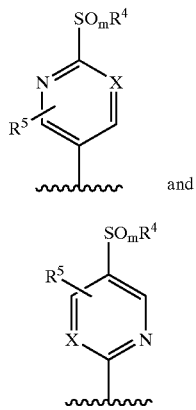

m is 0, 1 or 2;

X is $CR^7$;

$R^1$ is hydrogen, halo, $(C_1-C_6)$alkyl, $(C_2-C_6)$alkenyl, $(C_2-C_6)$alkynyl, $(C_3-C_7)$carbocyclyl, $(C_1-C_6)$alkoxy, $(C_1-C_6)$alkylcarbonyl, formyl, formamidyl, cyano, nitro, hydroxycarbonyl, $(C_1-C_6)$alkoxycarbonyl, $(C_2-C_9)$heteroarylcarbonyl, amino, N—$(C_1-C_6)$alkylamino, N,N—$[(C_1-C_6)$alkyl$]_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—$[(C_1-C_6)$alkyl$]_2$amido, N—$(C_6-C_{10})$arylamido, N—$(C_1-C_6)$alkyl-N—$(C_6-C_{10})$arylamido, N—$(C_1-C_6)$alkoxyamido, $(C_6-C_{10})$aryl, $(C_6-C_{10})$aryloxy, $(C_2-C_9)$heteroaryl, $(C_2-C_9)$heteroaryloxy, $(C_1-C_6)$alkylthio, $(C_6-C_{10})$arylthio, $(C_2-C_9)$heteroarylthio, $(C_1-C_6)$alkyl-S(=O)—, $(C_1-C_6)$alkyl-SO$_2$—, or $(C_1-C_6)$alkylcarbonyl-N($R^2$)—;

wherein each of said $R^1$ $(C_1-C_6)$alkyl group wherever they occur may optionally be substituted with one to three substituents independently selected from the group consisting of halo, hydroxy, $(C_2-C_6)$alkenyl, $(C_2-C_6)$alkynyl, $(C_3-C_7)$carbocyclyl, $(C_1-C_6)$alkoxy, carbonyl, formyl, formamidyl, $(C_1-C_6)$alkylcarbonyl, cyano, mercapto, nitro, hydroxycarbonyl, $(C_1-C_6)$alkoxycarbonyl, amino, N—$(C_1-C_6)$alkylamino, N,N—$[(C_1-C_6)$alkyl$]_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—$[(C_1-C_6)$alkyl$]_2$amido, N—$(C_6-C_{10})$arylamido, N—$(C_1-C_6)$alkyl-N—$(C_6-C_{10})$arylamido, $(C_1-C_6)$alkoxyamido, $(C_6-C_{10})$aryl, $(C_6-C_{10})$aryloxy, $(C_2-C_9)$heteroaryl, $(C_2-C_9)$heteroaryloxy, $(C_2-C_9)$heteroarylcarbonyl, $(C_1-C_6)$alkylthio, $(C_1-C_6)$alkyl-S(=O)—, $(C_1-C_6)$alkyl-SO$_2$—, $(C_1-C_6)$alkylcarbonyl-N($R^2$)—, and $(C_1-C_6)$alkylcarbonyloxy;

$R^2$ is hydrogen or $(C_1-C_6)$alkyl;

$R^3$ is $(C_1-C_6)$alkylthio, $(C_3-C_7)$carbocyclylthio, $C_6-C_{10}$ arylthio, $(C_2-C_9)$heteroarylthio, $(C_1-C_6)$alkyl-S(=O), $(C_6-C_{10})$aryl-S(=O), $(C_2-C_9)$heteroaryl-S(=O), $(C_1-C_6)$alkyl-SO$_2$—, $(C_6-C_{10})$aryl-SO$_2$—, $(C_2-C_9)$heteroaryl-SO$_2$—, $(C_1-C_6)$alkyl-SO$_2$-amino, $(C_3-C_7)$carbocyclyl-SO$_2$—amino, $(C_6-C_{10})$aryl-SO$_2$-amino, $(C_2-C_9)$heteroaryl-SO$_2$-amino, amino-SO$_2$—, N—$(C_1-C_6)$alkylamino-SO$_2$—, N,N—$[(C_1-C_6)$alkyl$]_2$amino-SO$_2$—, N—$(C_3-C_7)$carbocyclylamino-SO$_2$—, N—$(C_6-C_{10})$arylamino-SO$_2$—, N—$(C_1-C_6)$alkyl-N—$(C_6-C_{10})$arylamino-SO$_2$—, N—$(C_2-C_9)$heteroarylamino-SO$_2$—, amino, N—$(C_1-C_6)$alkylamino, N,N—$[(C_1-C_6)$alkyl$]_2$amino, N—$(C_3-C_7)$carbocyclylamino, N—$(C_6-C_{10})$arylamino, N—$(C_1-C_6)$alkyl-N—$(C_6-C_{10})$arylamino or N—$(C_2-C_9)$heteroarylamino;

wherein each of said $R^3$ $(C_1-C_6)$alkyl group wherever they occur may optionally be substituted with one to three substituents independently selected from the group consisting of halo, hydroxy, $(C_2-C_6)$alkenyl, $(C_2-C_6)$alkynyl, $(C_3-C_7)$carbocyclyl, $(C_1-C_6)$alkoxy, carbonyl, formyl, formamidyl, $(C_1-C_6)$alkylcarbonyl, cyano, mercapto, nitro, hydroxycarbonyl, $(C_1-C_6)$alkoxycarbonyl, amino, N—$(C_1-C_6)$alkylamino, N,N—$[(C_1-C_6)$alkyl$]_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—$[(C_1-C_6)$alkyl$]_2$amido, N—$(C_6-C_{10})$arylamido, N—$(C_1-C_6)$alkyl-N—$(C_6-C_{10})$arylamido, $(C_1-C_6)$alkoxyamido, $(C_6-C_{10})$aryl, $(C_6-C_{10})$aryloxy, $(C_2-C_9)$heteroaryl, $(C_2-C_9)$heteroaryloxy, $(C_2-C_9)$heteroarylcarbonyl, $(C_1-C_6)$alkylthio, $(C_1-C_6)$alkyl-S(=O)—, $(C_1-C_6)$alkyl-SO$_2$—, $(C_1-C_6)$alkylcarbonyl-N($R^2$)—, and $(C_1-C_6)$alkylcarbonyloxy;

$R^4$ is $(C_1-C_6)$alkyl optionally substituted by hydroxy or by one to three halo atoms;

$R^5$ is hydrogen, halo, hydroxy, mercapto, $(C_1-C_6)$alkyl, $(C_1-C_6)$alkoxy optionally substituted with one to three halogen atoms, $(C_2-C_6)$alkenyl, $(C_2-C_6)$alkynyl, $(C_3-C_7)$carbocyclyl, cyano, formyl, $(C_1-C_6)$alkylcarbonyl, $(C_1-C_6)$alkylcarbonyloxy, hydroxycarbonyl, $(C_1-C_6)$alkoxycarbonyl, amino, N—$(C_1-C_6)$alkylamino, N,N—$[(C_1-C_6)$alkyl$]_2$amino, N—($C_3$–$C_7$)carbocyclylamino N—($C_6$–$C_{10}$)arylamino N—($C_1$–$C_6$)alkyl-N—($C_6$–$C_{10}$)arylamino N—($C_2$–$C_9$) heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, N—($C_1$–$C_6$)alkoxyamido, or ($C_2$–$C_6$)alkylthio;

wherein each of said $R^5$ ($C_1$–$C_6$)alkyl group wberever they occur may optionally be substituted with one to three substituonts independently selected from the group consisting of halo, hydroxy, ($C_2$–$C_6$)alkenyl, ($C_2$–$C_6$)alkynyl, ($C_3$–$C_7$)carbocyclyl, ($C_1$–$C_6$)alkoxy, carbonyl, formyl, formamidyl, ($C_1$–$C_6$)alkylcarbonyl, cyano, mercapto, nitro, hydroxycarbonyl, ($C_1$–$C_6$)alkoxycarbonyl, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido ($C_1$–$C_6$)alkoxyamido, ($C_6$–$C_{10}$)aryl, ($C_6$–$C_{10}$)aryloxy, ($C_2$–$C_9$)heteroaryl, ($C_2$–$C_9$)heteroaryloxy, ($C_2$–$C_9$)heteroarylcarbonyl, ($C_1$–$C_6$)alkylthio, ($C_1$–$C_6$)alkyl-S(=O)—, ($C_1$–$C_6$)alkyl-SO$_2$—, ($C_1$–$C_6$)alkylcarbonyl-N($R^2$)—, and ($C_1$–$C_6$)alkylcarbonyloxy;

$R^6$ is selected from the group consisting of:

(a) phenyl optionally substituted by one to three substituents independently selected from the group consisting of halo, hydroxy, cyano, mercapto, hydroxycarbonyl, nitro, ($C_1$-$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —OCF$_3$, ($C_1$–$C_6$)alkylthio, ($C_1$–$C_6$)alkyl-S(=O)—, ($C_1$–$C_6$)alkyl-SO$_2$—, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, N—($C_1$–$C_6$)alkoxyamido, ($C_1$–$C_6$)alkylcarbonyloxy, ($C_1$–$C_6$)alkylcarbonyl-N($R^2$)—, formyl, ($C_1$–$C_6$)alkylcarbonyl, ($C_1$–$C_6$)alkoxycarbonyl, ($C_6$–$C_{10}$)aryl and ($C_2$–$C_9$)heterocyclyl;

(b) phenyl fused to a saturated, partially saturated or aromatic (5- to 7-membered)-carbocyclic ring;

wherein either of said phenyl or said fused saturated, partially saturated or aromatic (5- to 7-membered)-carbocyclic ring is optionally substituted by one to two substituents per ring, wherein said substituents are independently selected from the group consisting of halo, hydroxy, cyano, mercapto, hydroxycarbonyl, nitro, ($C_1$–$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —OCF$_3$, ($C_1$–$C_6$)alkylthio, ($C_1$–$C_6$)alkyl-S(=O)—, ($C_1$–$C_6$)alkyl-SO$_2$—, amino, N—($C_2$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, N—($C_1$–$C_6$)alkoxyamido, ($C_1$–$C_6$)alkylcarbonyloxy, ($C_1$–$C_6$)alkylcarbonyl-N($R^2$)—, formyl, ($C_1$–$C_6$)alkylcarbonyl, ($C_1$–$C_6$)alkoxycarbonyl, ($C_6$–$C_{10}$)aryl and ($C_2$–$C_9$)hcterocyclyl;

(c) phenyl fused to a saturated, partially saturated or aromatic (5- to 6-membered)-heterocyclyl containing one to two ring heteroatoms independently selected from the group consisting of —N=, —NR$^2$—, —S— and —O—;

wherein either of said phenyl or said fused saturated, partially saturated or aromatic (5- to 6-membered)-heterocyclyl is optionally substituted with one to two substituents per ring;

wherein said substituents are independently selected from tbe group consisting of halo, hydroxy, cyano, mercapto, hydroxycarbonyl, nitro, ($C_1$–$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —OCF$_3$, ($C_1$–$C_6$)alkylthio, ($C_1$–$C_6$)alkyl-S(=O)—, ($C_1$–$C_6$)alkyl-SO$_2$—, amino, N—($C_1$–$C_6$)alkylamino, N,N-[($C_1$–$C_6$)alkyl]$_2$amino, N—($C_3$–$C_7$)carbacyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, N—($C_1$–$C_6$)alkoxyamido, ($C_1$–$C_6$)alkylcarbonyloxy, ($C_1$–$C_6$)alkylcarbonyl-N($R^2$)—, formyl, ($C_1$–$C_6$)alkylcarbonyl, ($C_1$–$C_6$)alkoxycarbonyl, ($C_6$–$C_{10}$)aryl and ($C_2$–$C_9$)heterocyclyl;

(d) (3- to 7-membered)-carbocyclic optionally containing one or two double bonds;

wherein said (3- to 7-membered)-carbocyclic may also be optionally substituted by one to three substituents independently selected from the group consisting of halo, hydroxy, cyano, mercapto, hydroxycarbonyl, nitro, ($C_1$–$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —OCF$_3$, ($C_1$–$C_6$)alkylthio, ($C_1$–$C_6$)alkyl-S(=O)—, ($C_1$–$C_6$)alkyl-SO$_2$—, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, N—($C_1$–$C_6$)alkoxyamido, ($C_1$–$C_6$)alkylcarbonyloxy, ($C_1$–$C_6$)alkylcarbonyl-N($R^2$)—, formyl, ($C_1$–$C_6$)alkylcarbonyl, ($C_1$–$C_6$)alkoxycarbonyl, ($C_6$–$C_{10}$)aryl and ($C_2$–$C_9$)heterocyclyl;

(e) (5- to 7-membered)-carbocyclic fused to a saturated, partially saturated or aromatic (5- to 7-membered)-carbocyclic ring;

wherein said (5- to 7-membered)-carbocyclic may optionally contain one or two double bonds;

wherein either of said (5- to 7-membered)-carbocyclic or said fused saturated, partially saturated or aromatic (5- to 7-membered)-carbocyclic ring is optionally substituted by one to two substituents per ring, wherein said substituents are independently selected from the group consisting of halo, hydroxy, cyano, mercapto, hydroxycarbonyl, nitro, ($C_1$–$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —OCF$_3$, ($C_1$–$C_6$)alkylthio, ($C_1$–$C_6$)alkyl-S(=O)—, ($C_1$–$C_6$)alkyl-SO$_2$—, amino, N—($C_1$–$C_6$)alkylamino, N,N—[($C_1$–$C_6$)alkyl]$_2$amino, N—($C_3$–$C_7$)calbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, N—($C_1$–$C_6$)alkoxyamido, ($C_1$–$C_6$)alkylcarbonyloxy, ($C_1$–$C_6$)alkylcarbonyl-N($R^2$)—, formyl, ($C_1$–$C_6$)alkylcarborlyl, ($C_1$–$C_6$)alkoxycarbonyl, ($C_6$–$C_{10}$)aryl and ($C_2$–$C_9$) heterocyclyl;

(f) (5- to 7-membered)-carbocyclic fused to a saturated, partially saturated or aromatic (5- to 6-membered)-heterocyclyl containing one to two ring heteroatoms independently selected from the group consisting of —N=, —$NR^2$—, —S— and —O—;

wherein said (5- to 7-membered)-carbocyclic may optionally contain one or two double bonds;

wherein either of said (5- to 7-membered)-carbocyclic or said fused saturated, partially saturated or aromatic (5- to 6-membered)-heterocyclyl is optionally substituted with one to two substituents per ring;

wherein said substituents are independently selected from the group consisting of halo, hydroxy, cyano, mercapto, hydroxycarbonyl, nitro, ($C_1$–$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —$OCF_3$, ($C_1$–$C_6$)alkylthio, ($C_1$–$C_6$)alkyl-S(=O)—, ($C_1$–$C_6$)alkyl-$SO_2$—, amino, N—($C_1$–$C_6$)alkylamino, N,N—[($C_1$–$C_6$)alkyl]$_2$amino, N—($C_3$–$C_7$)carbocyclylamino N—($C_6$–$C_{10}$)arylamino N—($C_1$–$C_6$)alkyl-N—($C_6$–$C_{10}$)arylamino, N—($C_2$–$C_9$)heteroarylamino amido, N—($C_1$–$C_6$)alkylamido N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, N—($C_1$–$C_6$)alkoxyamido, ($C_1$–$C_6$)alkylcarbonyloxy, ($C_1$–$C_6$)alkylcarbonyl-N($R^2$)—, formyl, ($C_1$–$C_6$)alkylcarbonyl, ($C_1$–$C_6$)alkoxycarbonyl, ($C_6$–$C_{10}$)aryl and ($C_2$–$C_9$) heterocyclyl;

(g) saturated, partially saturated or aromatic (5- to 6-membered)-heterocyclyl containing one to four ring heteroatoms independently selected from the groups consisting of —N=, —$NR^2$—, —O—, and —S—;

wherein said (5- to 6-membered)-heterocyclyl is optionally substituted by one to three substituents independently selected from the group consisting of halo, hydroxy, cyano, mercapto, hydroxycarbonyl, nitro, ($C_1$–$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —$OCF_3$, ($C_1$–$C_6$)alkylthio, ($C_1$–$C_6$)alkyl-S(=O)—, ($C_1$–$C_6$)alkyl-$SO_2$—, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, N—($C_1$–$C_6$)alkoxyamido, ($C_1$–$C_6$)alkylcarbonyloxy, ($C_1$–$C_6$)alkylcarbonyl-N($R^2$)—, formyl, ($C_1$–$C_6$)alkylcarbonyl, ($C_1$–$C_6$)alkoxycarbonyl, ($C_6$–$C_{10}$)aryl and ($C_2$–$C_9$) heterocyclyl;

(h) saturated, partially saturated or aromatic (5- to 6-membered)-heterocyclyl containing one to two ring heteroatoms independently selected from the group consisting of —N=, —$NR^2$—, —S— and —O—;

wherein said saturated, partially saturated or aromatic (5- to 6-membered)-heterocyclyl is fused to a saturated, partially saturated or aromatic (5- to 7-membered)-carbocyclic ring;

wherein either of said saturated, partially saturated or aromatic (5- to 6-membered)-heterocyclyl ring or said fused saturated, partially saturated or aromatic (5- to 7-membered)-carbocyclic ring is optionally substituted by one to two substituents per ring;

wherein said substituents are independently selected from the group consisting of halo, hydroxy, cyano, mercapto, hydroxycarbonyl, nitro, ($C_1$–$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —$OCF_3$, ($C_1$–$C_6$)alkylthio, ($C_1$–$C_6$)alkyl-S(=O)—, ($C_1$–$C_6$)alkyl-$SO_2$—, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, N—($C_1$–$C_6$)alkoxyamido, ($C_1$–$C_6$)alkylcarbonyloxy, ($C_1$–$C_6$)alkylcarbonyl-N($R^2$)—, formyl, ($C_1$–$C_6$)alkylcarbonyl, ($C_1$–$C_6$)alkoxycarbonyl, ($C_6$–$C_{10}$)aryl and ($C_2$–$C_9$) heterocyclyl; and (i) saturated, partially saturated or aromatic (5- to 6-membered)-heterocyclyl containing one to two ring heteroatoms independently selected from the group consisting of —N=, —$NR^2$—, —S—, and —O—;

wherein said saturated, partially saturated or aromatic (5- to 6-membered)-heterocyclyl is fused to a saturated, partially saturated or aromatic (5- to 6-membered)-heterocyclyl containing one to two ring heteroatoms independently selected from the group consisting of —N=, —$NR^2$—, —S— and —O—;

wherein either of said saturated, partially saturated or aromatic (5- to 6-membered)-heterocyclyl or said fused saturated, partially saturated or aromatic (5- to 6-membered)-heterocyclyl is optionally substituted with one to two substituents per ring;

wherein said substituents are independently selected from the group consisting of halo, hydroxy, cyano, mercapto, hydroxycarbonyl, nitro, ($C_1$–$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —$OCF_3$, ($C_1$–$C_6$)alkylthio, ($C_1$–$C_6$)alkyl-S(=O)—, ($C_1$–$C_6$)alkyl-$SO_2$—, amino, N—($C_1$–$C_6$)alkylanuno, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, N—($C_1$–$C_6$)alkoxyamido, ($C_1$–$C_6$)alkylcarbonyloxy, ($C_1$–$C_6$)alkylcarbonyl-N($R^2$)—, formyl, ($C_1$–$C_6$)alkylcarbonyl, ($C_1$–$C_6$)alkoxycarbonyl, ($C_6$–$C_{10}$)aryl and ($C_2$–$C_9$) heterocyclyl;

wherein each of said $R^1$ (a), (b), (c), (d), (e), (f), (g), (h), or (i) ($C_1$–$C_6$)alkyl group wherever they occur may optionally be substituted with one to three substituents independently selected from the group consisting of halo, hydroxy, ($C_2$–$C_6$)alkenyl, ($C_2$–$C_6$)alkynyl, ($C_3$–$C_7$)carbocyclyl, ($C_1$–$C_6$)alkoxy, carbonyl, formyl, formamidyl, ($C_1$–$C_6$)alkylcarbonyl, cyano, mercapto, nitro, hydroxycarbonyl, ($C_1$–$C_6$)alkoxycarbonyl, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)hcteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—

($C_6$–$C_{10}$)arylamido, ($C_1$–$C_6$)alkoxyamido, ($C_6$–$C_{10}$)aryl, ($C_6$–$C_{10}$)aryloxy, ($C_2$–$C_9$)heteroaryl, ($C_2$–$C_9$)heteroaryloxy, ($C_2$–$C_9$)heteroarylcarbonyl, ($C_1$–$C_9$)alkylthio, ($C_1$–$C_6$)alkyl-S(=O)—, ($C_1$–$C_6$)alkyl-$SO_2$—, ($C_1$–$C_6$)alkylcarbonyl-N($R^2$)—, and ($C_1$–$C_6$)alkylcarbonyloxy;

$R^7$ is hydrogen, halo, hydroxy, mercapto, ($C_1$–$C_6$)alkyl, ($C_1$–$C_6$)alkoxy optionally substituted with one to three halogen atoms, ($C_2$–$C_6$)alkenyl, ($C_2$–$C_6$)alkynyl, ($C_3$–$C_7$)carbocyclyl, cyano, formyl, ($C_1$–$C_6$)alkylcarbonyl, ($C_1$–$C_6$)alkylcarbonyloxy, hydroxycarbonyl, ($C_1$–$C_6$)alkoxycarbonyl, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, N—($C_1$–$C_6$)alkoxyamido, nitro, or ($C_1$–$C_6$)alkylthio;

wherein each of said $R^7$ ($C_1$–$C_6$)alkyl group wherever they occur may optionally be substituted with one to three substituents independently selected from the group consisting of halo, hydroxy, ($C_2$–$C_6$)alkenyl, ($C_2$–$C_6$)alkynyl, ($C_3$–$C_7$)carbocyclyl, ($C_1$–$C_6$)alkoxy, carbonyl, formyl, formamidyl, ($C_1$–$C_6$)alkylcarbonyl, cyano, mexcapto, nitro, hydroxycarbonyl, ($C_1$–$C_6$)alkoxycaxbonyl, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, ($C_1$–$C_6$)alkoxyamido, ($C_6$–$C_{10}$)aryl, ($C_6$–$C_{10}$)aryloxy, ($C_2$–$C_9$)heteroalyl, ($C_2$–$C_9$)heteroaryloxy, ($C_2$–$C_9$)heteroarylcarbonyl, ($C_1$–$C_6$)alkylthio, ($C_1$–$C_6$)alkyl-S(=O)—, ($C_1$–$C_6$)alkyl-$SO_2$—, ($C_1$–$C_6$)alkylcarbonyl-N($R^2$)—, and ($C_1$–$C_6$)alkylcarbonyloxy;

or a pharmaceutically acceptAble salt thereof.

2. A compound according to claim 1 wherein said compound has the formula

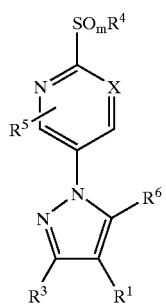

IA1 wherein X is $CR^7$; and m is 2.

3. A compound according to claim 1 wherein said compound has the formula

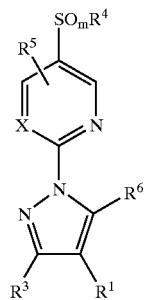

IA2 wherein X is $CR^7$; and m is 2.

4. A compound according to claim 1 wherein $R^6$ is
(a) phenyl optionally substituted by one to three substituents independently selected from the group consisting of halo, hydroxy, cyano, mercapto, hydroxycarbonyl, nitro, ($C_1$–$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —$OCF_3$, ($C_1$–$C_6$)alkylthio, ($C_1$–$C_6$)alkyl-S(=O)—, ($C_1$–$C_6$)alkyl-$SO_2$amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, N—($C_1$–$C_6$)alkoxyamido, ($C_1$–$C_6$)alkylcarbonyloxy, ($C_1$–$C_6$)alkylcarbonyl-N($R^2$)—, formyl, ($C_1$–$C_6$)alkylcarbonyl, ($C_1$–$C_6$)alkoxycarbonyl, ($C_6$–$C_{10}$)aryl and ($C_2$–$C_9$)heterocyclyl;

wherein each of said $R^6$ (a) ($C_1$–$C_6$)alkyl group wherever they occur may optionally be substituted with one to three substituents independently selected from the group consisting of halo, hydroxy, ($C_2$–$C_6$)alkenyl, ($C_2$–$C_6$)alkynyl, ($C_3$–$C_7$)carbocyclyl, ($C_1$–$C_6$)alkoxy, carbonyl, formyl, fonnamidyl, ($C_1$–$C_6$)alkylcarbonyl, cyano, mercapto, nitro, hydroxycarbonyl, ($C_1$–$C_6$)allcoxycarbonyl, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, ($C_1$–$C_6$)alkoxyamido, ($C_6$–$C_{10}$)aryl, ($C_6$–$C_{10}$)aryloxy, ($C_2$–$C_9$)heteroaryl, ($C_2$–$C_9$)heteroaryloxy, ($C_2$–$C_9$)heteroarylcarbonyl, ($C_1$–$C_6$)alkylthio, ($C_1$–$C_6$)alkyl-S(=O)—, ($C_1$–$C_6$)alkyl-$SO_2$—, ($C_1$–$C_6$)alkylcarbonyl-N($R^2$)—, and ($C_1$–$C_6$)alkylcarbonyloxy.

5. A compound according to claim 1 wherein $R^6$ is
(b) phenyl fused to a saturated, partially saturated or aromatic (5- to 7-membered)-carbocyclic ring;
wherein either of said phenyl or said fused saturated, partially saturated or aromatic (5- to 7-membered)-carbocyclic ring is optionally substituted by one to two substituents per ring, wherein said substituents are independently selected from the group consisting of halo, hydroxy, cyano, mercapto, hydroxycarbonyl, nitro, ($C_1$–$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —$OCF_3$, ($C_1$–$C_6$)alkylthio, ($C_1$–$C_6$)alkyl-S(=O)—, ($C_1$–$C_6$)alkyl-$SO_2$—, amino, N—($C_1$–$C_6$)alkylamino, N,N—

[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, N—($C_1$–$C_6$)alkoxyamido, ($C_1$–$C_6$)alkylcarbonyloxy, ($C_1$–$C_6$)alkylcarbonyl-N($R^2$)—, formyl, ($C_1$–$C_6$)alkylcarbonyl, ($C_1$–$C_6$)alkoxycarbonyl, ($C_6$–$C_{10}$)aryl and ($C_2$–$C_9$)heterocyclyl;

wherein each of said $R^6$ (b) ($C_1$–$C_6$)alkyl group wherever they occur may optionally be substituted with one to three substituents independently selected from the group consisting of halo, hydroxy, ($C_2$–$C_6$)alkenyl, ($C_2$–$C_6$)alkynyl, ($C_3$–$C_7$)carbocyclyl, ($C_1$–$C_6$)alkoxy, carbonyl, formyl, formamidyl, ($C_1$–$C_6$)alkylcarbonyl, cyano, mercapto, nitro, hydroxycaxbonyl, ($C_1$–$C_6$)alkoxycarbonyl, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, ($C_1$–$C_6$)alkoxyamido, ($C_6$–$C_{10}$)aryl, ($C_6$–$C_{10}$)aryloxy, ($C_2$–$C_9$)heteroaryl, ($C_2$–$C_9$)heteroaryloxy, ($C_2$–$C_9$)heteroarylcarbonyl, ($C_1$–$C_6$)alkylthio, ($C_1$–$C_6$)alkyl-S(=O)—, ($C_1$–$C_6$)alkyl-SO$_2$—, ($C_1$–$C_6$)alkylcarbonyl-N($R^2$)—, and ($C_1$–$C_6$)alkylcarbonyloxy.

6. A compound according to claim 1 wherein $R^6$ is (c) phenyl fused to a saturated, partially saturated or aromatic (5- to 6-membered)-heterocyclyl containing one to two ring heteroatoms independently selected from the group consisting of —N=, —N$R^2$—, —S— and —O—;

wherein either of said phenyl or said fused saturated, partially saturated or aromatic (5- to 6-membered)-heterocyclyl is optionally substituted with one to two substituents per ring;

wherein said substituents are independently selected from the group consisting of halo, hydroxy, cyano, mercapto, hydroxycarbonyl, nitro, ($C_1$–$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —OCF$_3$, ($C_1$–$C_6$)alkylthio, ($C_1$–$C_6$)alkyl-S(=O)—, ($C_1$–$C_6$)alkyl-SO$_2$—, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, N—($C_1$–$C_6$)alkoxyamido, ($C_1$–$C_6$)alkylcarbonyloxy, ($C_1$–$C_6$)alkylcarbonyl-N($R^2$)—, formyl, ($C_1$–$C_6$)alkylcarbonyl, ($C_1$–$C_6$)alkoxycarbonyl, ($C_6$–$C_{10}$)aryl and ($C_2$–$C_9$)heterocyclyl;

wherein each of said $R^6$ (c) ($C_1$–$C_6$)alkyl group wherever they occur may optionally be substituted with one to three substituents independently selected from the group consisting of halo, hydroxy, ($C_2$–$C_6$)alkenyl, ($C_2$–$C_6$)alkynyl, ($C_3$–$C_7$)carbocyctyl, ($C_1$–$C_6$)alkoxy, carbonyl, formyl, formamidyl, ($C_1$–$C_6$)alkylcarbonyl, cyano, mercapto, nitro, hydroxycarbonyl, ($C_1$–$C_6$)alkoxycarbonyl, amino, N—($C_1$–$C_6$)alkylamino, N,N—[($C_1$–$C_6$)alkyl]$_2$amino, N—($C_3$–$C_7$)carbocyclyl amino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, ($C_1$–$C_6$)alkoxyamido, ($C_6$–$C_{10}$)aryl, ($C_6$–$C_{10}$)aryloxy, ($C_2$–$C_9$)heteroaryl, ($C_2$–$C_9$)heteroaryloxy, ($C_2$–$C_9$)heteroarylcarbonyl, ($C_1$–$C_6$)alkylthio, ($C_1$–$C_6$)alkyl-S(=O)—, ($C_1$–$C_6$)alkyl-SO$_2$—, ($C_1$–$C_6$)alkylcarbonyl-N($R^2$)—, and ($C_1$–$C_6$)alkylcarbonyloxy.

7. A compound according to claim 1 wherein $R^6$ is (d) (3- to 7-membered)-carbocycuc optionally containing one or two double bonds;

wherein said, (3- to 7-membered)-carbocyclic may also be optionally substituted by one to three substituents independently selected from the group consisting of halo, hydroxy, cyano, mereapto, hydroxycarbonyl, nitro, ($C_1$–$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —OCF$_3$, ($C_1$–$C_6$)alkylthio, ($C_1$–$C_6$)alkyl-S(=O)—, ($C_1$–$C_6$)alkyl-SO$_2$—, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido N—($C_1$–$C_6$)alkoxyamido, ($C_1$–$C_6$)alkylcarbonyloxy, ($C_1$–$C_6$)alkylcarbonyl-N($R^2$)—, formyl, ($C_1$–$C_6$)alkylcarbonyl, ($C_1$–$C_6$)alkoxycarbonyl, ($C_6$–$C_{10}$)aryl and ($C_2$–$C_9$)hetcrocyclyl;

wherein each of said $R^6$ (d) ($C_1$–$C_6$)alkyl group wherever they occur may optionally be substituted with one to three substituents independently selected from the group consisting of halo, hydroxy, ($C_2$–$C_6$)alkenyl, ($C_2$–$C_6$)alkynyl, ($C_3$–$C_7$)carbocyclyl, ($C_1$–$C_6$)alkoxy, carbonyl, formyl, formamidyl, ($C_1$–$C_6$)alkylcarbonyl, cyano, mercapto, nitro, hydroxycarbonyl, ($C_1$–$C_6$)alkoxycarbonyl, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alky]$_2$amido, N—($C_6$–$C_{10}$)arylamido, N—($C_1$–$C_6$)alkyl-N—($C_6$–$C_{10}$)arylamido, ($C_1$–$C_6$)alkoxyamido, ($C_6$–$C_{10}$)aryl, ($C_6$–$C_{10}$)aryolxy, ($C_2$–$C_9$)heteroaryl, ($C_2$–$C_9$)heteroaryloxy, ($C_2$–$C_9$)heteroarylcarbonyl, ($C_1$–$C_6$)alkythio, ($C_1$–$C_6$)alkyl-S(=O)—, ($C_1$–$C_6$)alkyl-S(=O)—, ($C_1$–$C_6$)alkylcarbonyl-N($R^2$)—, and ($C_1$–$C_6$)alkylcarbonyloxy.

8. A compound according to claim 1 wherein $R^6$ is (e) (5- to 7-membered)-carbocyclic fused to a saturated, partially saturated or aromatic (5- to 7-membered)-carbocyclic ring;

wherein said (5- to 7-membered)-carbocyclic may optionally contain one or two double bonds;

wherein either of said (5- to 7-membered)-carbocyclic or said fused saturated, partially saturated or aromatic (5- to 7-membered)-carbocyclic ring is optionally substituted by one to two substituents per ring, wherein said substituents are independently selected from the group consisting of halo, hydroxy, cyano, mercapto, hydroxycarbonyl, nitro, ($C_1$–$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —OCF$_3$, ($C_1$–$C_6$)alkylthio, ($C_1$–$C_6$)alkyl-S(=O)—, ($C_1$–$C_6$)alkyl-$SO_2$—, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylammo, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido N—($C_1$–$C_6$)alkoxyamido, ($C_1$–$C_6$)alkylcarbonyloxy, ($C_1$–$C_6$)alkylcarbonyl-N($R^2$)—, formyl, ($C_1$–$C_6$)alkylcarbonyl, ($C_1$–$C_6$)alkoxycarbonyl, ($C_6$–$C_{10}$)aryl and ($C_2$–$C_9$)heterocyclyl;

- wherein each of said $R^6$ (e) ($C_1$–$C_6$)alkyl group wherever they occur may optionally be substituted with one to three substituents independently selected from the group consisting of halo, hydroxy, ($C_2$–$C_6$)alkenyl, ($C_2$–$C_6$)alkynyl, ($C_3$–$C_7$)carbocyclyl, ($C_1$–$C_6$)alkoxy, carbonyl, formyl, formamidyl, ($C_1$–$C_6$)alkylcarbonyl, cyano, mercapto, nitro, hydroxycarbonyl, ($C_1$–$C_6$)alkoxycarbonyl, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, ($C_1$–$C_6$)alkoxyamido, ($C_6$–$C_{10}$)aryl, ($C_6$–$C_{10}$)aryloxy, ($C_2$–$C_9$)heteroaryl, ($C_2$–$C_9$)heteroaryloxy, ($C_2$–$C_9$)heceroarylcarbonyl, ($C_1$–$C_6$)alkylthio, ($C_1$–$C_6$)alkyl-S(=O)—, ($C_1$–$C_6$)alkyl-$SO_2$—, ($C_1$–$C_6$)alkylcarbonyl-N($R^2$)—, and ($C_1$–$C_6$)alkylcarbonyloxy.

9. A compound according to claim 1 wherein $R^6$ is
- (f) (5- to 7-membered)-carbocyclic fused to a saturated, partially saturated or aromatic (5- to 6-membered)-heterocyclyl containing one to two ring heteroatoms independently selected from the group consisting of —N=, —$NR^2$—, —S— and —O—;
- wherein said (5- to 7-membered)-carbocyclic may optionally contain one or two double bonds;
- wherein either of said (5- to 7-membered)-carbocyclic or said fused saturated, partially saturated or aromatic (5- to 6-membered)-heterocyclyl is optionally substituted with one to two substituents per ring;
- wherein said substituents are independently selected from the group consisting of halo, hydroxy, cyano, mercapto, hydroxycarbonyl, nitro, ($C_1$–$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —$OCF_3$, ($C_1$–$C_6$)alkylthio, ($C_1$–$C_6$)alkyl-S(=O)—, ($C_1$–$C_6$)alkyl-$SO_2$—, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido N—($C_1$–$C_6$)alkoxyamido, ($C_1$–$C_6$)alkylcarbonyloxy, ($C_1$–$C_6$)alkylcarbonyl-N($R^2$)—, formyl, ($C_1$–$C_6$)alkylcarbonyl, ($C_1$–$C_6$)alkoxycarbonyl, ($C_6$–$C_{10}$)aryl and ($C_2$–$C_9$)heterocyclyl;
- wherein each of said $R^6$ (f) ($C_1$–$C_6$)alkyl group wherever they occur may optionally be substituted with one to three substituents independently selected from the group consisting of halo, hydroxy, ($C_2$–$C_6$)alkenyl, ($C_2$–$C_6$)alkynyl, ($C_3$–$C_7$)carbocyclyl, ($C_1$–$C_6$)alkoxy, carbonyl, formyl, formamidyl, ($C_1$–$C_6$)alkylcaxbonyl, cyano, mercapto, nitro, hydroxycarbonyl, ($C_1$–$C_6$)alkoxycarbonyl, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamido N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, ($C_1$–$C_6$)alkoxyamido, ($C_6$–$C_{10}$)aryl, ($C_6$–$C_{10}$)aryloxy, ($C_2$–$C_9$)heteroaryl, ($C_2$–$C_9$)heteroaryloxy, ($C_2$–$C_9$)heteroarylcarbonyl, ($C_1$–$C_6$)alkylthio, ($C_1$–$C_6$)alkyl-S(=O)—, ($C_1$–$C_6$)alkyl-$SO_2$—, ($C_1$–$C_6$)alkylcarbonyl-N($R^2$)—, and ($C_1$–$C_6$)alkylcarbonyloxy.

10. A compound according to claim 1 wherein $R^6$ is
- (g) saturated, partially saturated or aromatic (5- to 6-membered)-heterocyclyl containing one to four ring heteroatoms independently selected from the groups consisting of —N=, —$NR^2$—, —O—, and —S—;
- wherein said (5- to 6-membered)-heterocyclyl is optionally substituted by one to three substituents independently selected from the group consisting of halo, hydroxy, cyano, mercapto, hydroxycarbonyl, nitro, ($C_1$–$C_6$)alkyl, ($C_2$–$C_6$)alkenyl, ($C_2$–$C_6$)alkynyl, ($C_3$–$C_7$)carbocyclyl, ($C_1$–$C_6$)alkoxy, —$OCF_3$, ($C_1$–$C_6$)alkylthio, ($C_1$–$C_6$)alkyl-S(=O)—, ($C_1$–$C_6$)alkyl-$SO_2$—, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamido N—($C_2$–$C_9$)heteroarylamino, amido, N—($C_1$–$C_6$)alkylamino, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, N—($C_1$–$C_6$)alkoxyamido, ($C_1$–$C_6$)alkylcarbonyloxy, ($C_1$–$C_6$)alkylcarbonyl-N($R^2$)—, formyl, ($C_1$–$C_6$)alkylcarbonyl, ($C_1$–$C_6$)alkoxycarbonyl, ($C_6$–$C_{10}$)aryl and ($C_2$–$C_9$)heterocyclyl;
- wherein each of said $R^6$ (g) ($C_1$–$C_6$)alkyl group wherever they occur may optionally be substituted with one to three substituents independently selected from the group consisting of halo, hydroxy, ($C_2$–$C_6$)alkenyl, ($C_2$–$C_6$)alkynyl, ($C_3$–$C_7$)carbocyclyl, ($C_1$–$C_6$)alkoxy, carbonyl, formyl, formamidyl, ($C_1$–$C_6$)alkylcarbonyl, cyano, mercapto, nitro, hydroxycarbonyl, ($C_1$–$C_6$)alkoxycarbonyl, amino, N—($C_1$–$C_6$)alkylamino, N,N—[($C_1$–$C_6$)alkyl]$_2$amino, N—($C_3$–$C_7$)carbocyclylamino, N—($C_6$–$C_{10}$)arylamino, N—($C_1$–$C_6$)alkyl-N—($C_6$–$C_{10}$)arylamino, N—($C_2$–$C_9$)heteroarylamino, amido, N—($C_1$–$C_6$)alkylamido, N,N—[($C_1$–$C_6$)alkyl]$_2$amido, N—($C_6$–$C_{10}$)arylamido, N—($C_1$–$C_6$)alkyl-N—($C_6$–$C_{10}$)arylamido, ($C_1$–$C_6$)alkoxyamido, ($C_6$–$C_{10}$)aryl, ($C_6$–$C_{10}$)aryloxy, ($C_2$–$C_9$)heteroaryl, ($C_2$–$C_9$)heteroaryloxy, ($C_2$–$C_9$)heteroarylcarbonyl, ($C_1$–$C_6$)alkylthio, ($C_1$–$C_6$)alkyl-S(=O)—, ($C_1$–$C_6$)alkyl-$SO_2$—, ($C_1$–$C_6$)alkylcarbonyl-N($R^2$)—, and ($C_1$–$C_6$)alkylcarbonyloxy.

11. A compound according to claim 1 wherein $R^6$ is
- (h) saturated, partially saturated or aromatic (5- to 6-membered)-heterocyclyl containing one to two ring heteroatoms independently selected from the group consisting of —N=, —$NR^2$—, —S— and —O—;
- wherein said saturated, partially saturated or aromatic (5- to 6-membered)-heterocyclyl is fused to a saturated, partially saturated or aromatic (5- to 7-membered)-carbocyclic ring;

wherein either of said saturated, partially saturated or aromatic (5- to 6-membered)-heterocyclyl ring or said fused saturated, partially saturated or aromatic (5- to 7-membered)-carbocyclic ring is optionally substituted by one to two substituents per ring;

wherein said substituents are independently selected from the group consisting of halo, hydroxy, cyano, mercapto, hydroxycarbonyl, nitro, $(C_1-C_6)$alkyl, $(C_2-C_6)$alkenyl, $(C_2-C_6)$alkynyl, $(C_3-C_7)$carbocyclyl, $(C_1-C_6)$alkoxy, —OCF$_3$, $(C_1-C_6)$alkylthio, $(C_1-C_6)$alkyl-S(=O)—, $(C_1-C_6)$alkyl-SO$_2$—, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N—$(C_6-C_{10})$arylamido, N—$(C_1-C_6)$alkoxyamido, $(C_1-C_6)$alkylcarbonyloxy $(C_1-C_6)$alkylcarbonyl-N$(R^2)$—, formyl, $(C_1-C_6)$alkylcarbonyl, $(C_1-C_6)$alkoxycarbonyl, $(C_6-C_{10})$aryl and $(C_2-C_9)$heterocyclyl;

wherein each of R$^6$ (h) $(C_1-C_6)$alkyl group wherever they occur may optionally be substituted with one to three substituents Independently selected from the group consisting of halo, hydroxy, $(C_2-C_6)$alkenyl, $(C_2-C_6)$alkynyl, $(C_3-C_7)$carbocyclyl, $(C_1-C_6)$alkoxy, carbonyl, formyl, formamidyl, $(C_1-C_6)$alkylcarbonyl, cyano, mercapto, nitro, hydroxycarbonyl, $(C_1-C_6)$alkoxycarbonyl, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N—$(C_6-C_{10})$arylamido, $(C_1-C_6)$alkoxyamido, $(C_6-C_{10})$aryl, $(C_6-C_{10})$aryloxy, $(C_2-C_9)$heteroaryl, $(C_2-C_9)$heteroaryloxy, $(C_2-C_9)$heteroarylcarbonyl, $(C_1-C_6)$alkylthio, $(C_1-C_6)$alkyl-S(=O)—, $(C_1-C_6)$alkyl-SO$_2$—, $(C_1-C_6)$alkylcarbonyl-N$(R^2)$—, and $(C_1-C_6)$alkylcarbonyloxy.

12. A compound according to claim 1 wherein R$^6$ is (i) saturated, partially saturated or aromatic (5- to 6-membered)-heterocyclyl containing one to two ring heteroatoms independently selected from the group consisting of —N=, —NR$^2$—, —S—, and —O—;

wherein said saturated, partially saturated or aromatic (5- to 6-membered)-heterocyclyl is fused to a saturated, partially saturated or aromatic (5- to 6-membered)-heterocyclyl containing one to two ring heteroatoms independently selected from the group consisting of —N=, —NR$^2$—, —S— and —O—;

wherein either of said saturated, partially saturated or aromatic (5- to 6-membered)-heterocyclyl or said fused saturated, partially saturated or aromatic (5- to 6-membered)-heterocyclyl is optionally substituted with one to two substituents per ring;

wherein said substituents are independently selected from the group consisting of halo, hydroxy, cyano, mercapto, hydroxycarbonyl, nitro, $(C_1-C_6)$alkyl, $(C_2-C_6)$alkenyl, $(C_2-C_6)$alkynyl, $(C_3-C_7)$carbocyclyl, $(C_1-C_6)$alkoxy, —OCF$_3$, $(C_1-C_6)$alkylthio, $(C_1-C_6)$alkyl-S(=O)—, $(C_1-C_6)$alkyl-SO$_2$—, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N-$(C_6-C_{10})$arylamido, N—$(C_1-C_6)$alkoxyamido, $(C_1-C_6)$alkylcarbonyloxy, $(C_1-C_6)$alkylcarbonyl-N$(R^2)$—, formyl, $(C_1-C_6)$alkylcarbonyl, $(C_1-C_6)$alkoxycarbonyl, $(C_6-C_{10})$aryl and $(C_2-C_9)$heterocyclyl;

wherein each of said R$^6$ (i) $(C_1-C_6)$alkyl group wherever they occur may optionally be substituted with one to three substituents independently selected from the group consisting of halo, hydroxy, $(C_2-C_6)$alkenyl, $(C_2-C_6)$alkynyl, $(C_3-C_7)$carbocyclyl, $(C_1-C_6)$alkoxy, carbonyl, formyl, formamidyl, $(C_1-C_6)$alkylcarbonyl, cyano, mercapto, nitro, hydroxycarbonyl, $(C_1-C_6)$alkoxycarbonyl, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, N—$(C_2-C_9)$heteroarylamino, amido, N—$(C_1-C_6)$alkylamido, N,N—[$(C_1-C_6)$alkyl]$_2$amido, N—$(C_6-C_{10})$arylamido, N—$(C_1-C_6)$alkyl-N—$(C_6-C_{10})$arylamido, $(C_1-C_6)$alkoxyamido, $(C_6-C_{10})$aryl, $(C_6-C_{10})$aryolxy, $(C_2-C_9)$heteroaryl, $(C_2-C_9)$heteroaryloxy, $(C_2-C_9)$heteroarylcarbonyl, $(C_1-C_6)$alkylthio, $(C_1-C_6)$alkyl-S(=O)—, $(C_1-C_6)$alkyl-SO$_2$—, $(C_1-C_6)$alkylcarbonyl-N$(R^2)$—, and $(C_1-C_6)$alkylcarbonyloxy.

13. A compound according to claim 1 wherein R$^6$ is phenyl optionally substituted with one to three halo or one to three $(C_1-C_6)$alkyl.

14. A compound according to claim 1 wherein R$^6$ is aromatic (5- to 6-membered)-heterocyclyl containing one to two ring heteroatoms independently selected from the groups consisting of —N=, —NR$^2$—, —O—, and —S—; wherein said (5- to 6-membered)-heterocyclyl is optionally substituted by one to three halo or one to three $(C_1-C_6)$alkyl.

15. A compound according to claim 1 wherein R$^1$ is hydrogen, halo, cyano, or $(C_1-C_6)$alkylcarbonyl.

16. A compound according to claim 1 wherein R$^1$ is cyano.

17. A compound according to claim 1 wherein R$^3$ is $(C_1-C_6)$alkylthio, $(C_3-C_7)$carbocyclylthio, $C_6-C_{10})$arylthio, $(C_2-C_9)$heteroarylthio, $(C_1-C_6)$alkyl-S(=O), $(C_6-C_{10})$aryl-S(=O), $(C_2-C_9)$heteroaryl-S(=O), $(C_1-C_6)$alkyl-SO$_2$—, $(C_6-C_{10})$aryl-SO$_2$—, $(C_2-C_9)$heteroaryl-SO$_2$—, $(C_1-C_6)$alkyl-SO$_2$-amino, $(C_3-C_7)$carbocyclyl-SO$_2$-amino, $(C_6-C_{10})$aryl-SO$_2$-amino, $(C_2-C_9)$heteroaryl-SO$_2$-amino, amino-SO$_2$—, N—$(C_1-C_6)$alkylamino-SO$_2$, N,N—[$(C_1-C_6)$alkyl]$_2$amino-SO$_2$—, N—$(C_3-C_7)$carbocyclylamino-SO$_2$—, N—$(C_6-C_{10})$arylamino-SO$_2$—, N—$(C_1-C_6)$alkyl-N—$(C_6-C_{10})$arylamino-SO$_2$—, N—$(C_2-C_9)$heteroarylamino-SO$_2$—, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, or N—$(C_2-C_9)$heteroarylamino.

18. A compound according to claim 1 wherein R$^3$ is $C_1-C_6$)alkylthio, $(C_3-C_7)$carbocyclylthio, $C_6-C_{10}$)arylthio, $(C_2-C_9)$heteroarylthio, amino, N—$(C_1-C_6)$alkylamino, N,N—[$(C_1-C_6)$alkyl]$_2$amino, N—$(C_3-C_7)$carbocyclylamino, N—$(C_6-C_{10})$arylamino, N—$(C_1-C_6)$alkyl-N—$(C_6-C_{10})$arylamino, or N—$(C_2-C_9)$heteroarylamino.

19. A compound according to claim 1 wherein R$^3$ is $(C_1-C_6)$alkylthio or amino.

20. A compound according to claim 1 wherein $R^4$ is $(C_1-C_6)$alkyl optionally substituted by one to three halo atoms.

21. A compound according to claim 1 wherein $R^4$ is methyl.

22. A compound according to claim 1 wherein said compound is selected from the group consisting of:

1-(5-Methanesulfonyl-pyridin-2-yl)-3-methylsulfanyl-5-phenyl-1H-pyrazole-4-carbonitrile;

5-(4-Chloro-phenyl)-1-(5-methanesulfonyl-pyridin-2-yl)-3-methylsulfanyl-1H-pyrazole-4-carbonitrile;

1-(5-Methanesulfonyl-pyridin-2-yl)-3-methylsulfanyl-5-p-tolyl-1H-pyrazole-4-carbonitrile;

1-(5-Methanesulfonyl-pyridin-2-yl)-3-methylsulfanyl-5-thiophen-2-yl-1H-pyrazole-4-carbonitrile;

1-(5-Methanesulfonyl-pyridin-2-yl)-3-methylsulfanyl-5-m-tolyl-1H-pyrazole-4-carbonitrile;

5-(3-Chloro-phenyl)-1-(5-methanesulfonyl-pyridin-2-yl)-3-methylsulfanyl-1H-pyrazole-4-carbonitrile;

3-Methanesulfonyl-1-(5-methanesulfonyl-pyridin-2-yl)-5-phenyl-1H-pyrazole-4-carbonitrile;

3-Azido-1-(5-methanesulfonyl-pyridin-2-yl)-5-phenyl-1H-pyrazole-4-carbonitrile;

3-Amino-1-(5-methanesulfonyl-pyridin-2-yl)-5-phenyl-1H-pyrazole-4-carbonitrile;

N-[4-Cyano-1-(5-methanesulfonyl-pyridin-2-yl)-5-phenyl-1H-pyrazol-3-yl]-methanesulfonamide;

[4-Cyano-1-(5-methanesulfonyl-pyridin-2-yl)-5-phenyl-1H-pyrazol-3-ylamino]-acetic acid;

[4-Cyano-1-(5-methanesulfonyl-pyridin-2-yl)-5-phenyl-1H-pyrazol-3-ylamino]-acetic acid methyl ester;

1-(6-Methanesulfonyl-pyridin-3-yl)-3-methylsulfonyl-5-phenyl-1H-pyrazole-4-carbonitrile;

3-Methanesulfonyl-1-(6-methanesulfonyl-pyridin-3-yl)-5-phenyl-1H-pyrazole-4-carbonitrile;

3-Methanesulfonyl-1-(6-methanesulfonyl-pyridin-3-yl)-5-phenyl-1H-pyrazole-4-carbonitrile;

or a pharmaceutically acceptable salt thereof.

23. A pharmaceutical composition for the treatment of a condition selected from the group consisting of arthritis, fever, menstrual cramps, inflammatory bowel disease, Crohn's disease, asthma, bronchitis, chronic obstructive pulmonary disease, tissue ulceration, peptic ulcers, gastritis, regional enteritis, ulcerative colitis, recurrent gastrointestinal lesion, gastrointestinal bleeding, ocular angiogenesis, corneal injury, macular degeneration, conjunctivitis, abnormal wound healing, skin disorders, myasthenia gravis, polymyositis, myositis, bursitis, burns, and premature labor in a mammal, comprising an amount of a compound of claim 1 or a pharmaceutically acceptable salt thereof effective in such treatments and a pharmaceutically acceptable carrier.

24. A method for treating a condition selected from the group consisting of arthritis, fever, menstrual cramps, inflammatory bowel disease, Crohe's disease, asthma, bronchitis, chronic obstructive pulmonary disease, tissue ulceration, peptic ulcers, gastritis, regional enteritis, ulcerative colitis, recurrent gastrointestinal lesion, gastrointestinal bleeding, ocular angiogenesis, corneal injury, macular degeneration, conjunctivitis, abnormal wound healing, skin disorders, myasthenia gravis, polymyositis, myositis, bursitis, burns, corneal scarring, and premature labor in a mammal, comprising administering to said mammal an amount of a compound according to claim 1 or a pharmaceutically acceptable salt thereof effective in treating such a condition.

* * * * *